(12) United States Patent
Sugibayashi et al.

(10) Patent No.: US 12,296,014 B2
(45) Date of Patent: May 13, 2025

(54) EXTERNAL PREPARATION COMPRISING NON-LAMELLAR LIQUID CRYSTAL-FORMING LIPID

(71) Applicant: FARNEX INCORPORATED, Tokyo (JP)

(72) Inventors: Kenji Sugibayashi, Saitama (JP); Hiroaki Todo, Saitama (JP); Ichiro Hijikuro, Kanagawa (JP); Masahisa Tanomura, Kanagawa (JP); Sayaka Mori, Kanagawa (JP)

(73) Assignee: FARNEX INCORPORATED, Tokyo (JP)

( * ) Notice: Subject to any disclaimer, the term of this patent is extended or adjusted under 35 U.S.C. 154(b) by 712 days.

(21) Appl. No.: 17/273,973

(22) PCT Filed: Sep. 9, 2019

(86) PCT No.: PCT/JP2019/035419
§ 371 (c)(1),
(2) Date: Mar. 5, 2021

(87) PCT Pub. No.: WO2020/050423
PCT Pub. Date: Mar. 12, 2020

(65) Prior Publication Data
US 2021/0330794 A1   Oct. 28, 2021

(30) Foreign Application Priority Data
Sep. 7, 2018   (JP) ................................. 2018-168365

(51) Int. Cl.
| | | |
|---|---|---|
| *A61K 47/14* | (2017.01) | |
| *A61K 9/70* | (2006.01) | |
| *A61K 31/4174* | (2006.01) | |
| *A61K 31/485* | (2006.01) | |
| *A61K 31/5517* | (2006.01) | |
| *A61K 31/573* | (2006.01) | |

(52) U.S. Cl.
CPC ............ *A61K 47/14* (2013.01); *A61K 9/7015* (2013.01); *A61K 9/7061* (2013.01); *A61K 31/4174* (2013.01); *A61K 31/485* (2013.01); *A61K 31/5517* (2013.01); *A61K 31/573* (2013.01)

(58) Field of Classification Search
CPC .... A61K 47/14; A61K 9/7015; A61K 9/7061; A61K 31/4174; A61K 31/485; A61K 31/5517; A61K 31/573; A61K 8/0208; A61K 8/0295; A61K 8/046; A61K 8/375; A61K 9/1274; A61K 8/60; A61K 9/1075; A61K 9/12; A61P 17/00; A61Q 19/00
See application file for complete search history.

(56) References Cited

U.S. PATENT DOCUMENTS

| | | |
|---|---|---|
| 2008/0113923 A1 | 5/2008 | Hatoh et al. |
| 2012/0264923 A1 | 10/2012 | Ikeda et al. |
| 2019/0117777 A1 | 4/2019 | Kawamura et al. |

FOREIGN PATENT DOCUMENTS

| | | | |
|---|---|---|---|
| EP | 3391906 A1 | 10/2018 | |
| JP | 11-513393 | 11/1999 | |
| JP | 2012-017318 A | 1/2012 | |
| WO | WO 97/13528 | 4/1997 | |
| WO | WO-9713528 A1 * | 4/1997 | ............. A61K 47/14 |
| WO | WO 2006/043705 A1 | 4/2006 | |
| WO | WO 2011/078383 A1 | 6/2011 | |
| WO | WO 2016/121962 A1 | 8/2016 | |
| WO | WO 2017/104840 A1 | 6/2017 | |
| WO | WO 2018/043731 A1 | 3/2018 | |

OTHER PUBLICATIONS

Todo et al., "Transmucosal absorption promotion of drugs using non-lamellar liquid crystals", including English translation, Programs and Abstracts of the 30th Annual Meeting of the Japan Society of Drug Delivery System, DDS, 2014, p. 171 (1-F-16), published Jul. 1, 2014, 5 pages.
Aoki et al., "1-E-16, Skin Permeability of Water-Soluble Substance Model From Skin-Applicable Tape Formulation Containing Self-Assembling Lipid", Programs and Abstracts of the 34th Annual Meeting of the Japan Society of Drug Delivery System, 2018, p. 160, published May 28, 2018, 4 pages.
Extended European Search Report in Europe Application No. 19858114.2, dated May 6, 2022, 6 pages.
Kadhum Wesam R. et al., "A Novel Chemical Enhancer Approach for Transdermal Drug Delivery with $C_{17}$-Monoglycerol Ester Liquid Crystal-forming Lipid", vol. 66, No. 5, Jan. 1, 2017, pp. 443-454, XP55915010.
Lu, G., "New Drug Dosage Forms and New Techniques", *People's Medical Publishing House*, (Chinese and English translation) Beijing, China, Apr. 1998 (5 pages).
Office Action in Japanese Application No. 2020-541328 (and English translation) dated Jan. 9, 2024 (7 pages).
Kokame, et al., "Post-translational modification of proteins by fatty acids and isoprenoids", *Vitamin*, Mar. 1992; 66(3); (Japanese Reference and English translation) (8 pages).
Lu, G., "New Drug Dosage Forms and New Technologies" *People's Medical Publishing House*, 2nd Edition, Beijing, Jul. 2005 (Chinese Reference and English translation) (5 pages).
Bourganis, Vassillis, et al., Recent advances in carrier mediated nose-to-brain delivery of pharmaceutics, May 4, 2018, pp. 337-62, European Journal of Pharmaceutics and Biopharmaceutics (26 pages).

\* cited by examiner

*Primary Examiner* — Snigdha Maewall
(74) *Attorney, Agent, or Firm* — Crowell & Moring LLP

(57) ABSTRACT

The present invention relates to an external preparation that is well retained on a living body surface and is capable of increasing drug permeability, in particular, an external preparation comprising a non-lamellar liquid crystal-forming lipid and a drug.

11 Claims, 18 Drawing Sheets

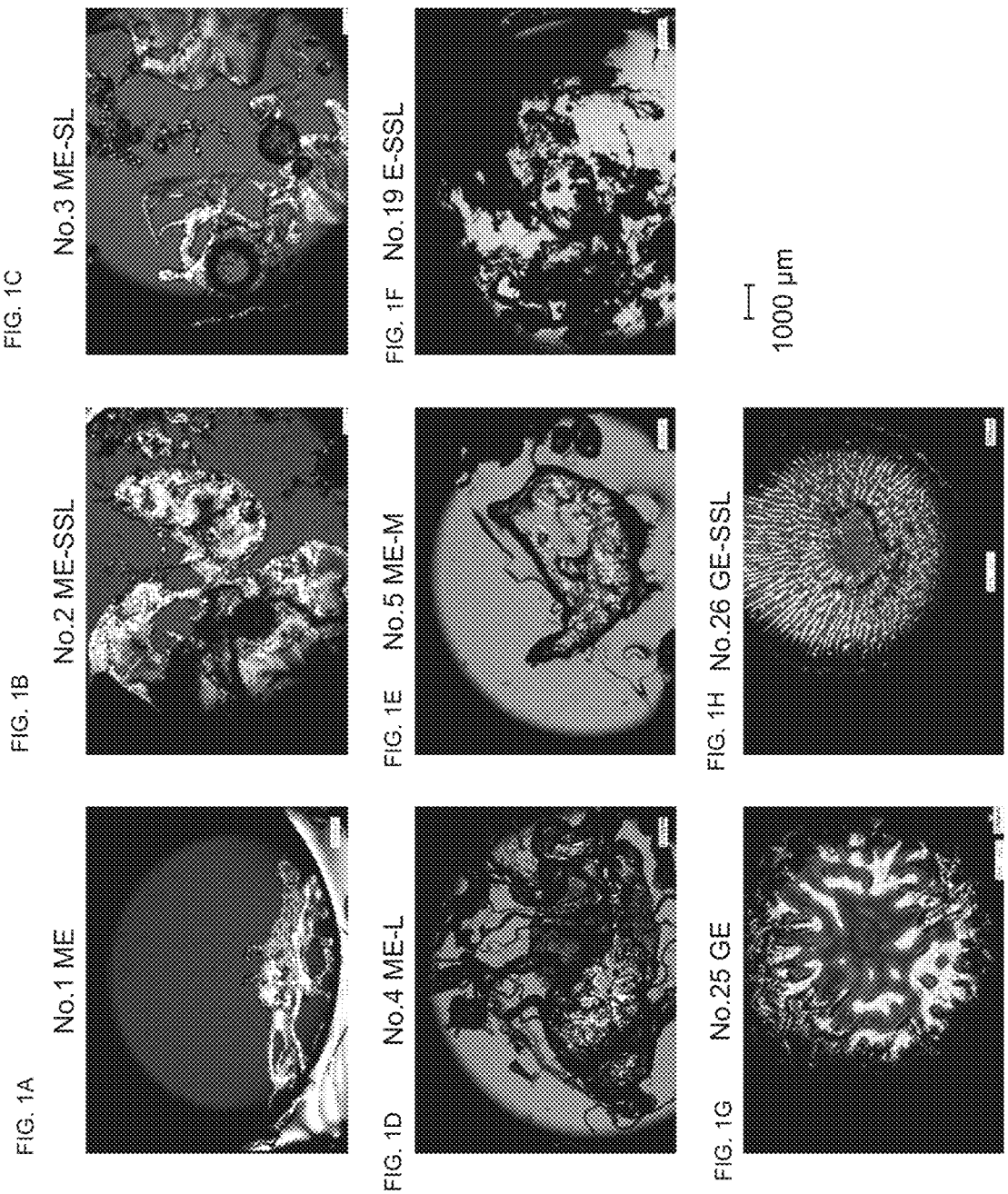

EXTERNAL PREPARATION COMPRISING NON-LAMELLAR LIQUID CRYSTAL-FORMING LIPID

RELATED APPLICATIONS

This application is a 371 application of PCT/JP2019/035419 having an international filing date of Sep. 9, 2019, which claims priority to JP 2018-168365 filed Sep. 7, 2018, the entire content of each of which is incorporated herein by reference.

TECHNICAL FIELD

The present invention relates to an external preparation comprising a non-lamellar liquid crystal-forming lipid.

BACKGROUND ART

Transdermal absorption formulations which are applied to the skin for use have advantages such as convenient administration and sustained release, and are increasingly used not only for local administration but systemic administration of various drugs. However, the transdermal absorption formulations are known to have basically low drug absorbability because the skin has a function of restricting substance permeation as a biological barrier. Accordingly, various transdermal absorption promoters are used in the transdermal absorption formulations in order to promote drug permeation through the skin. Nonetheless, the resulting transdermal absorption promoting effect is not always sufficient.

Many reports have mentioned the usefulness of lyotropic liquid crystals such as liposomes as biomimetic drug delivery system (DDS) carriers since the DDS concept was proposed. In recent years, non-lamellar liquid crystals (NLLCs), one type of the lyotropic liquid crystals, have been reported to have advantages such as high drug content percentages, easy preparability, and high stability in macromolecule medicaments, as compared with conventional DDS carriers.

Various liquid crystal-forming compounds are used for various applications in the fields of cosmetics, pharmaceutical products, and the like. In recent years, lipid compounds capable of forming cubic liquid crystals that exhibit high stability even at low temperatures (lower than 6° C.) have been developed, and use of the liquid crystals in sustained release formulations has also been reported (Patent Literature 1). However, such lipid compounds have high viscosities and thus do not allow the compounds to pass through a thin injection needle (e.g., 30 gauge), and their use has difficulty in injections. Accordingly, lipid compounds capable of stably forming non-lamellar liquid crystals and having lower viscosities have been developed as bases for injections (Patent Literature 2). Patent Literature 3 discloses a skin external preparation comprising liquid crystals formed by such a lipid compound having a low viscosity. However, its main dosage form is a lotion or an emulsion and does not have a high retaining property on the skin. Patent Literature 3 does not describe the application of the external preparation to tissues other than the skin.

CITATION LIST

Patent Literature

Patent Literature 1: International Patent Publication WO 2006/043705

Patent Literature 2: International Patent Publication WO 2011/078383

Patent Literature 3: Japanese Patent Publication No. 2012-17318A

SUMMARY OF INVENTION

Technical Problem

A problem underlying the present invention is to provide an external preparation that is well retained on the living body surface and is capable of increasing drug permeability.

Solution to Problem

The present inventors have conducted diligent studies to solve the problem and produced formulations such as patches such as tape formulations, aerosol formulations, and liquid crystal precursor formulations using non-lamellar liquid crystal-forming lipids. As a result, the present inventors have found that: a favorable formulation retaining property on living body surfaces and increased drug permeability can be achieved; and such formulations are suitable not only for skin application but for mucosal application, reaching the completion of the present invention.

Specifically, the present invention encompasses the following:

[1] An external preparation comprising a non-lamellar liquid crystal-forming lipid and a drug.

[2] The external preparation according to [1] above, wherein the non-lamellar liquid crystal-forming lipid is an amphipathic compound represented by the following general formula (I) or a salt thereof:

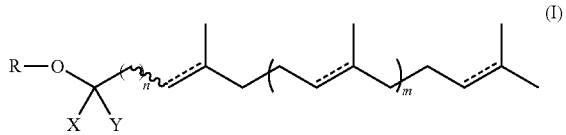

wherein X and Y each denotes a hydrogen atom or together denote an oxygen atom, n denotes an integer from 0 to 2, m denotes the integer 1 or 2, the designation:

denotes a single bond or double bond, and R denotes a hydrophilic group having two or more hydroxyl groups.

[3] The external preparation according to [2] above, wherein R in the formula denotes a hydrophilic group generated by removal of one hydroxyl group from any one selected from the group consisting of glycerol, erythritol, pentaerythritol, diglycerol, glyceric acid, triglycerol, xylose, sorbitol, ascorbic acid, glucose, galactose, mannose, dipentaerythritol, maltose, mannitol, and xylitol.

[4] The external preparation according to any of [1] to [3] above, wherein the non-lamellar liquid crystal-forming lipid is mono-O-(5,9,13,17-tetramethyloctadec-4-enoyl)glycerol, or mono-O-(5,9,13-trimethyltetradec-4-enoyl)glycerol.

[5] The external preparation according to [1] above, wherein the non-lamellar liquid crystal-forming lipid is glyceryl monooleate or phytantriol.

[6] The external preparation according to any of [1] to [5] above, wherein the external preparation is formulated in a dosage form of a patch.

[7] The external preparation according to [6] above, wherein the patch is a tape formulation.

[8] The external preparation according to [6] or [7] above, wherein the external preparation comprises 70 w/w % or more of an adhesive.

[9] The external preparation according to any of [1] to [5] above, wherein the external preparation is formulated in a dosage form of an aerosol formulation.

[10] The external preparation according to any of [1] to [9] above, wherein the non-lamellar liquid crystal-forming lipid forms no liquid crystal in the external preparation.

[11] The external preparation according to any of [1] to [10] above for use in mucosal application.

[12] The external preparation according to any of [1] to [11] above, further comprising a water soluble polymer and/or an oil.

[13] The external preparation according to [12] above, wherein the water soluble polymer is hydroxypropylcellulose.

[14] The external preparation according to any of [1] to [13] above, further comprising ethanol.

[15] The external preparation according to any of [1] to [5] above, wherein the external preparation comprises fine particles comprising the non-lamellar liquid crystal-forming lipid and the drug.

[16] The external preparation according to any of [1] to [15] above for use in drug delivery into brain.

The present application encompasses the contents disclosed in Japanese Patent Application No. 2018-168365 on which the priority of the present application is based.

Advantageous Effects of Invention

The present invention can provide an external preparation that is well retained on a living body surface and is capable of increasing drug permeability through the skin. The present invention can also provide an external preparation that can bring about high drug permeability through the mucosa when applied to the mucosa.

BRIEF DESCRIPTION OF DRAWINGS

FIGS. 1A, 1B, 1C, 1D, 1E, 1F, 1G and 1H show photographs showing images observed under a polarizing microscope. FIG. 1A: formulation No. 1, FIG. 1B: formulation No. 2, FIG. 1C: formulation No. 3, FIG. 1D: formulation No. 4, FIG. 1E: formulation No. 5, FIG. 1F: formulation No. 19, FIG. 1G: formulation No. 25, and FIG. 1H: formulation No. 26.

FIG. 2A: formulation No. 1, FIG. 2B: formulation No. 2, FIG. 2C: formulation No. 3, FIG. 2D: formulation No. 13, FIG. 2E: formulation No. 25, FIG. 2F: formulation No. 26, and FIG. 2G: formulation No. 27.

FIG. 3A: formulation No. 37, FIG. 3B: formulation No. 45.

FIG. 6A: formulation No. 52 (supplemented with water), FIG. 6B: formulation No. 53 (supplemented with water), FIG. 6C: formulation No. 56 (supplemented with water), FIG. 6D: formulation No. 57 (supplemented with water), and FIG. 6E: formulation No. 56 (non-supplemented with water).

FIG. 9A: formulation No. 73, 1 μm×1 μm observation field of view. FIG. 9B: formulation No. 63, 1 μm×1 μm observation field of view. FIG. 9C: formulation No. 73, 0.5 μm×0.5 μm observation field of view. FIG. 9D: formulation No. 63, 0.5 μm×0.5 μm observation field of view.

FIG. 13A: formulation No. 75, FIG. 13B: formulation No. 76, and FIG. 13C: formulation No. 77.

FIG. 17A: midbrain, FIG. 17B: cortex, FIG. 17C: cerebellum, and FIG. 17D: hippocampus.

FIG. 18A: spinal cord, and FIG. 18B: olfactory bulb.

DESCRIPTION OF EMBODIMENTS

Figure 2A:
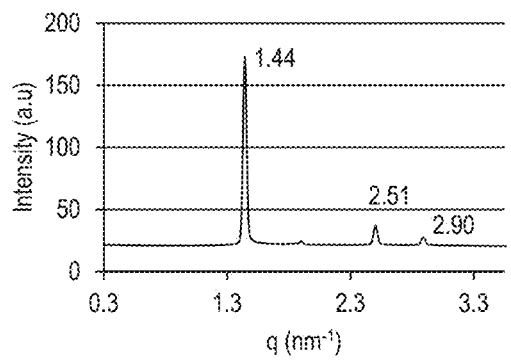
FIGS. 2A, 2B, 2C, 2D, 2E, 2F and 2G are diagrams showing results of small-angle X-ray diffraction.
Figure 2B:
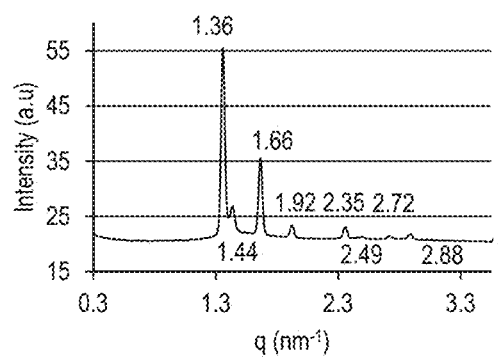
Figure 2C:
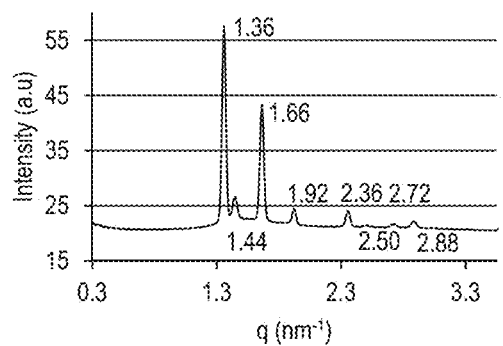
Figure 2D:
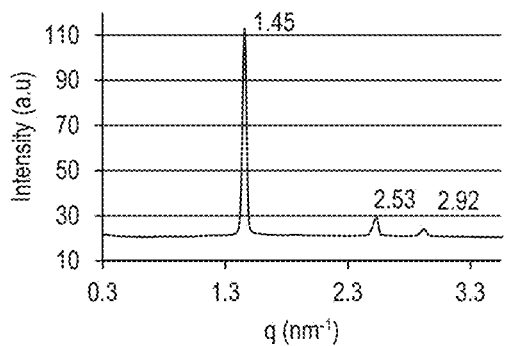
Figure 2E:
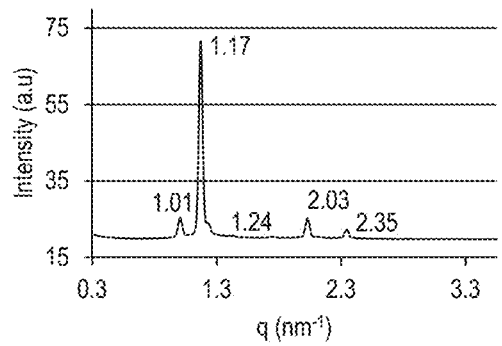
Figure 2F:
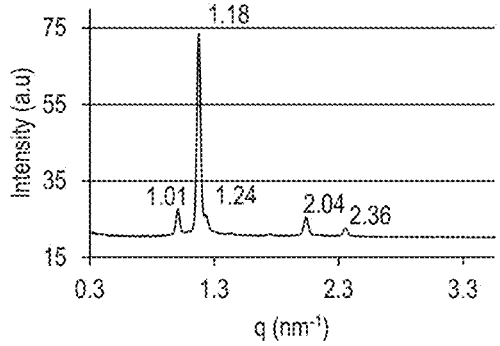
Figure 2G:
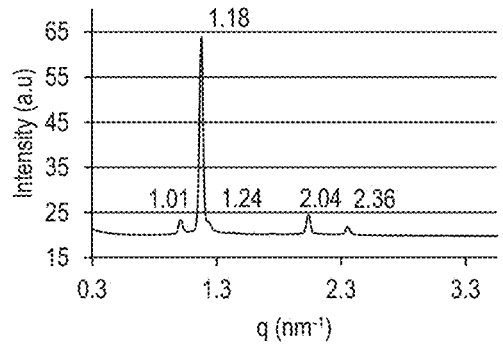
Figure 3A:
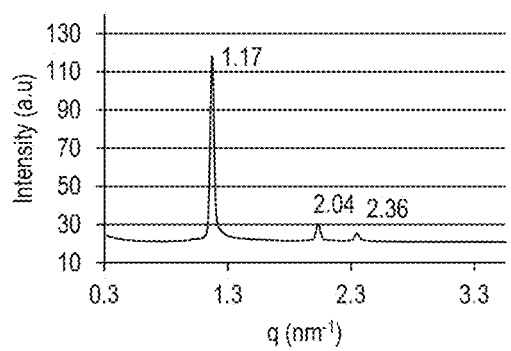
FIGS. 3A, 3B. 3C. 3D. 3E. and 3F are diagrams showing results of small-angle X-ray diffraction.
Figure 3B:
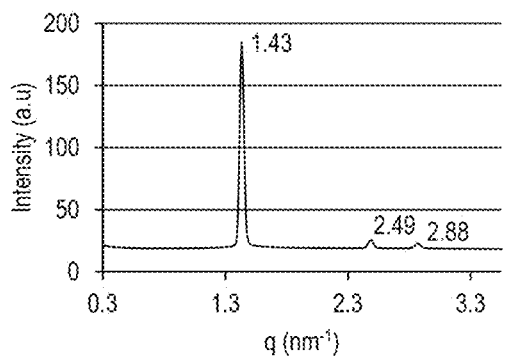
Figure 3C:
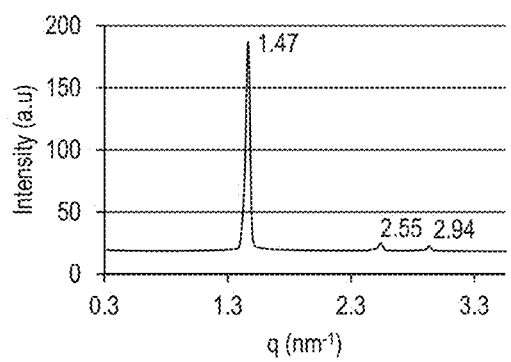
FIG. 3C: formulation No. 46.
Figure 3D:
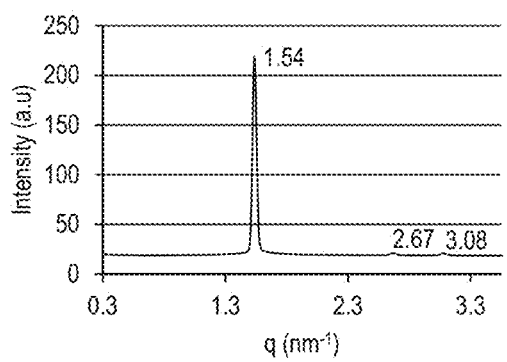
FIG. 3D: formulation No. 47.
Figure 3E:
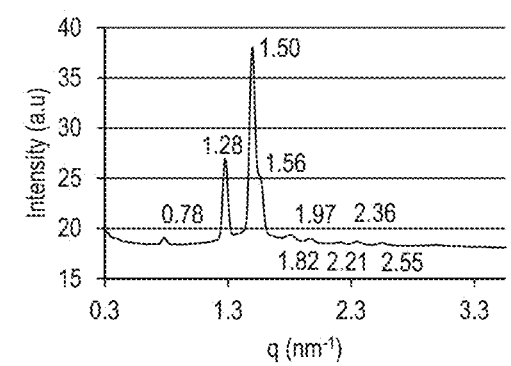
FIG. 3E: formulation No. 48.
Figure 3F:
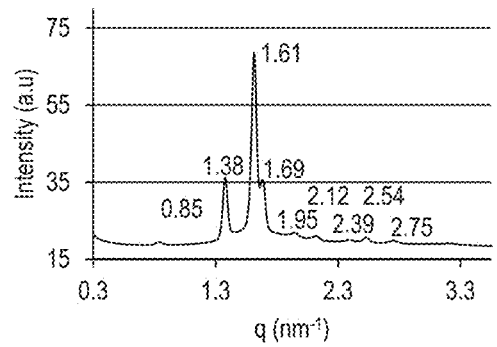
FIG. 3F: formulation No. 49.

Hereinafter, the present invention will be described in detail.

The present invention relates to an external preparation comprising a non-lamellar liquid crystal-forming lipid and a drug. In the present invention, the external preparation refers to a medicament that is to be applied to a living body surface (the skin or the mucosa, etc.) for the purpose of administering a drug. The external preparation may be a pharmaceutical composition. Preferably, the external preparation according to the present invention has a living body surface adhesive property and is stably retained on a living body surface. When the external preparation according to the present invention is applied to a living body surface, the drug is released from liquid crystals formed by the non-lamellar liquid crystal-forming lipid in the external preparation so that the drug efficiently passes through the skin, the mucosa, or the like and absorbed (administered) into the body. The external preparation according to the present invention can markedly promote the permeation of the drug through the skin, the mucosa, or the like.

1. Non-Lamellar Liquid Crystal-Forming Lipid

In the present invention, a lipid capable of forming non-lamellar liquid crystals (non-lamellar liquid crystal-forming lipid) can be used as a liquid crystal-forming lipid. The non-lamellar liquid crystal-forming lipid used in the present invention is preferably a low-molecular-weight amphipathic compound. In this context, the term "low-molecular-weight" means a molecular weight from about 20 to 10,000. The molecular weight of the non-lamellar liquid crystal-forming lipid used in the present invention is preferably 50 to 5,000, more preferably 100 to 2,500, further preferably 200 to 1,000.

In one embodiment, an amphipathic compound represented by the following general formula (I) or a salt thereof can be used as the non-lamellar liquid crystal-forming lipid:

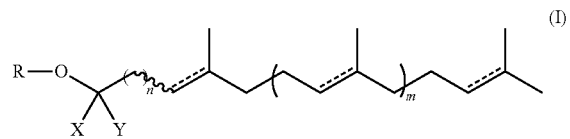

(I)

In the general formula (I), X and Y each denotes a hydrogen atom or together denote an oxygen atom. In the general formula (I), n denotes an integer from 0 to 2 (preferably 1 or 2), and m denotes the integer 1 or 2. The combination of n and m for the amphipathic compound represented by the general formula (I) may be: n=0 and m=1; n=0 and m=2; n=1 and m=1; n=1 and m=2; n=2 and m=1; or n=2 and m=2.

In the above formula, the designation:

═════ denotes a single bond or double bond.

R in the general formula (I) denotes a hydrophilic group having two or more hydroxyl groups. The hydrophilic group may be, but not limited to, for example, a hydrophilic group generated by removal of one hydroxyl group (OH) from any one selected from the group consisting of glycerol, erythritol, pentaerythritol, diglycerol, glyceric acid, triglycerol, xylose, sorbitol, ascorbic acid, glucose, galactose, mannose, dipentaerythritol, maltose, mannitol, and xylitol. R in the general formula (I) is more preferably a hydrophilic group generated by removal of one hydroxyl group (OH) from glycerol, pentaerythritol, erythritol, diglycerol, glyceric acid, or xylose, particularly preferably a hydrophilic group generated by removal of one hydroxyl group (OH) from glycerol. The hydrophilic group generated by removal of one hydroxyl group (OH) from glyceric acid may be a group generated by removal of OH (hydroxyl group) contained in a carboxyl group of glyceric acid.

In the present invention, the designation in the general formula (I):

ᵕᵕ means that the amphipathic compound is an E-(cis-) or Z-(trans-) geometric isomer, or a mixture thereof. The same holds true for this designation in the general formulas (II) and (III) mentioned later.

An example of the amphipathic compound represented by the general formula (I) is an amphipathic compound represented by the following general formula (II):

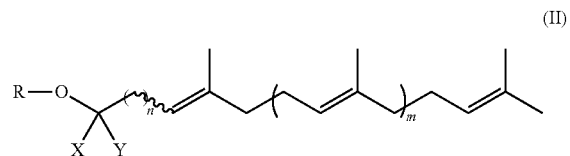

(II)

In the general formula (II), X and Y each denotes a hydrogen atom or together denote an oxygen atom, n denotes an integer from 0 to 2 (0, 1 or 2), and m denotes 1 or 2.

R in the general formula (II) denotes a hydrophilic group generated by removal of one hydroxyl group (OH) from any one selected from the group consisting of glycerol, erythritol, pentaerythritol, diglycerol, glyceric acid, triglycerol, xylose, sorbitol, ascorbic acid, glucose, galactose, mannose, dipentaerythritol, maltose, mannitol, and xylitol. A preferred example of R is a hydrophilic group generated by removal of one hydroxyl group (OH) from any one selected from the group consisting of glycerol, pentaerythritol, erythritol, diglycerol, glyceric acid, and xylose, further preferably a hydrophilic group generated by removal of one hydroxyl group (OH) from glycerol. The hydrophilic group generated by removal of one hydroxyl group (OH) from glyceric acid may be a group generated by removal of OH (hydroxyl group) contained in a carboxyl group of glyceric acid.

Another example of the amphipathic compound represented by the general formula (I) is an amphipathic compound represented by the following general formula (III):

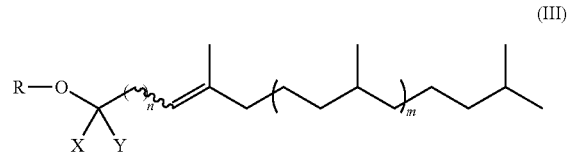

(III)

In the general formula (III), X and Y each denotes a hydrogen atom or together denote an oxygen atom, n denotes an integer from 0 to 2 (preferably 1 or 2), and m denotes 1 or 2.

R in the general formula (III) denotes a hydrophilic group having two or more hydroxyl groups. The hydrophilic group may be, but not limited to, for example, a hydrophilic group generated by removal of one hydroxyl group (OH) from any one selected from the group consisting of glycerol, erythritol, pentaerythritol, diglycerol, glyceric acid, triglycerol, xylose, sorbitol, ascorbic acid, glucose, galactose, mannose, dipentaerythritol, maltose, mannitol, and xylitol. A preferred example of R is a hydrophilic group generated by removal of one hydroxyl group (OH) from any one selected from the group consisting of glycerol, pentaerythritol, erythritol, diglycerol, glyceric acid, and xylose, further preferably a hydrophilic group generated by removal of one hydroxyl group (OH) from glycerol. The hydrophilic group generated by removal of one hydroxyl group (OH) from glyceric acid may be a group generated by removal of OH (hydroxyl group) contained in a carboxyl group of glyceric acid.

A further alternative example of the amphipathic compound represented by the general formula (I) is an amphipathic compound represented by the following general formula (IV):

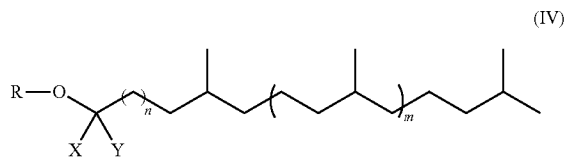

In the general formula (IV), X and Y each denotes a hydrogen atom or together denote an oxygen atom, n denotes an integer from 0 to 2 (preferably 1 or 2), and m denotes 1 or 2.

R in the general formula (IV) denotes a hydrophilic group having two or more hydroxyl groups. The hydrophilic group may be, but not limited to, for example, a hydrophilic group generated by removal of one hydroxyl group (OH) from any one selected from the group consisting of glycerol, erythritol, pentaerythritol, diglycerol, glyceric acid, triglycerol, xylose, sorbitol, ascorbic acid, glucose, galactose, mannose, dipentaerythritol, maltose, mannitol, and xylitol. A preferred example of R is a hydrophilic group generated by removal of one hydroxyl group (OH) from any one selected from the group consisting of glycerol, pentaerythritol, erythritol, diglycerol, glyceric acid, and xylose, further preferably a hydrophilic group generated by removal of one hydroxyl group (OH) from glycerol. The hydrophilic group generated by removal of one hydroxyl group (OH) from glyceric acid may be a group generated by removal of OH (hydroxyl group) contained in a carboxyl group of glyceric acid.

Preferred examples of the amphipathic compound represented by the general formula (I) include, but are not limited to, the following:

mono-O-(5,9,13-trimethyltetradec-4-enoyl)glycerol,
mono-O-(5,9,13-trimethyltetradecanoyl)glycerol,
mono-O-(5,9,13-trimethyltetradeca-4,8,12-trienoyl)glycerol,
mono-O-(5,9,13,17-tetramethyloctadec-4-enoyl)glycerol,
mono-O-(5,9,13,17-tetramethyloctadecanoyl)glycerol, and
mono-O-(5,9,13,17-tetramethyloctadeca-4,8,12,16-tetraenoyl)glycerol.

Further preferred examples thereof include mono-O-(5,9,13-trimethyltetradec-4-enoyl)glycerol, and mono-O-(5,9,13,17-tetramethyloctadec-4-enoyl)glycerol.

The amphipathic compound represented by the general formula (I) used in the present invention exhibits high stability under broad environmental conditions. For example, the amphipathic compound represented by the general formula (I) is characterized in that this amphipathic compound has an isoprenoid chain as a hydrophobic group and thus, unlike an amphipathic compound having a linear chain of fatty acid such as oleic acid as a hydrophobic group, the amphipathic compound has high resistance to hydrolysis and relatively high oxidation stability. The amphipathic compound represented by the general formula (I) has also a wide temperature range that allows liquid crystal formation and low Krafft temperature, and can stably form liquid crystals even at low temperatures (6° C. or lower, preferably 0° C. or lower).

The amphipathic compound represented by the general formula (I) used in the present invention exhibits a low viscosity in itself. Specifically, the amphipathic compound represented by the general formula (I) has a viscosity of preferably 15.0 Pa-s or less, more preferably 11.0 Pa-s or less, further preferably 6.0 Pa-s or less, by itself, as measured at 25° C. This viscosity can be measured using, for example, a viscosity and viscoelasticity measuring apparatus (Gemini II, Malvern Instruments Ltd.) at a temperature of 25° C.

The external preparation according to the present invention may comprise a salt of the amphipathic compound represented by the general formula (I). The salt of the amphipathic compound represented by the general formula (I) according to the present invention may be any type of salt, including salts of alkali metals and alkaline-earth metals such as sodium, potassium, calcium, and magnesium and preferably sodium salt or potassium salt. The salt of the amphipathic compound represented by the general formula (I) of the present invention may be a pharmaceutically acceptable salt or may be a salt acceptable for production of cosmetics.

The present invention is not limited to the external preparation containing the amphipathic compound represented by the general formula (I) or the salt thereof, and any of other non-lamellar liquid crystal-forming lipids may be used in the present invention.

The non-lamellar liquid crystal-forming lipid used in the present invention may be, for example, glycerin fatty acid monoester. The fatty acid constituting the glycerin fatty acid monoester is preferably a saturated or unsaturated fatty acid having 8 to 24 carbon atoms. Other examples of the glycerin fatty acid monoester include, but are not limited to, glyceryl monooleate (GMO; also called monoolein), glyceryl monoisostearate, and glyceryl monoeraidicate. Alternatively, glycerin monoalkyl ether may be used as the non-lamellar liquid crystal-forming lipid. Specific examples of the glycerin monoalkyl ether include, but are not limited to, glycerin monooleyl ether (also called oleyl glyceryl), glycerin monoisostearyl ether (also called isostearyl glyceryl), and glycerin monoeraidyl ether. Phytantriol (PHY) or the like may be used as another non-lamellar liquid crystal-forming lipid.

The term "non-lamellar liquid crystal-forming lipid" used in the present invention also encompasses a combination of two or more lipids that form non-lamellar liquid crystals by mixing, and a lipid that forms non-lamellar liquid crystals in combination with a component such as an oil. Such non-lamellar liquid crystal-forming lipids are known to persons skilled in the art.

The liquid crystal structure to be formed may be changed by adding one or more types of predetermined components such as an oil to the non-lamellar liquid crystal-forming lipid used in the present invention. Even when the external preparation comprises the non-lamellar liquid crystal-forming lipid and such components and changes a liquid crystal structure as compared with the case of not comprising the components, this external preparation and the non-lamellar liquid crystal-forming lipid used therein are included in the scopes of the "external preparation" and the "non-lamellar liquid crystal-forming lipid", respectively, according to the present invention as long as non-lamellar liquid crystals are also formed after change of the liquid crystal structure.

The non-lamellar liquid crystal-forming lipid used in the present invention can form non-lamellar liquid crystals in an aqueous medium (aqueous phase). In relation to the invention, the aqueous medium comprising the non-lamellar liquid crystal-forming lipid is also referred to as a "non-lamellar liquid crystal-forming lipid/water system" or an "amphipathic compound/water system".

The non-lamellar liquid crystal-forming lipid contained in the external preparation according to the present invention forms non-lamellar liquid crystals in the external preparation, or forms non-lamellar liquid crystals on a living body surface in the presence of surrounding water upon application to the living body surface, or forms non-lamellar liquid crystals on a living body surface by the volatilization of a volatile component (a solvent such as ethanol, a propellant, etc.) upon application to the living body surface. The non-lamellar liquid crystals formed by the non-lamellar liquid crystal-forming lipid contained in the external preparation according to the present invention are, but not limited to, preferably type II (water-in-oil) liquid crystals wherein hydrophobic groups are oriented outward, more preferably cubic liquid crystals, reverse hexagonal liquid crystals, or a mixture system thereof.

The liquid crystal structure formed by the non-lamellar liquid crystal-forming lipid can be analyzed by conventional methods such as observation under a polarizing microscope and small-angle X-ray scattering (SAXS) measurement.

For example, whether or not to have each liquid crystal structure may be determined by a small-angle X-ray scattering (SAXS) method, for the purpose of confirming liquid crystal formation. Usually, a non-lamellar liquid crystal-forming lipid/water system sample with a predetermined concentration can first be filled into an X-ray capillary tube made of quartz, for example, and the capillary tube is then sealed with an oxy-fuel burner, and subjected to SAXS assay.

Liquid crystal formation can be confirmed by determining whether or not to exhibit the following scattering peak ratio (peak interval) peculiar to each liquid crystal structure as a result of SAXS measurement.

Ratio of Pn3m cubic liquid crystal: $\sqrt{2}:\sqrt{3}:\sqrt{4}:\sqrt{6}:\sqrt{8}:\sqrt{9}:\sqrt{10}:\ldots$ Ratio of Ia3d cubic liquid crystal: $\sqrt{3}:\sqrt{4}:\sqrt{7}:\sqrt{8}:\sqrt{10}:\sqrt{11}:\ldots$ Ratio of Im3m cubic liquid crystal: $\sqrt{2}:\sqrt{4}:\sqrt{6}:\sqrt{8}:\sqrt{10}:\sqrt{12}:\sqrt{14}:\ldots$ Ratio of Fd3m cubic liquid crystal: $\sqrt{3}:\sqrt{8}:\sqrt{11}:\sqrt{12}:\sqrt{16}:\sqrt{19}:\sqrt{24}:\sqrt{27}:\ldots$ Ratio of reverse hexagonal liquid crystal: $1:\sqrt{3}:2:\ldots$ The space group and the lattice constant can be easily determined by calculating a peak value from SAXS data and then calculating the reciprocal ratio therefrom according to a method well known to persons skilled in the art, based thereon.

The amphipathic compound represented by the general formula (I) for use in the external preparation of the present invention can be synthesized with reference to Examples mentioned later or according to a synthesis method described in International Publication WO 2014/178256. Alternatively, the amphipathic compound represented by the general formula (III) can be synthesized according to, for example, a synthesis method described in International Publication WO 2011/078383. The amphipathic compound represented by the general formula (IV) can be synthesized according to, for example, a synthesis method described in International Publication WO 2006/043705.

It is preferably verified that the thus synthesized compounds are compounds of interest by conventional methods such as NMR measurement.

Various other non-lamellar liquid crystal-forming lipids are commercially available. Glyceryl monooleate (GMO) and phytantriol (PHY) are commercially available from Tokyo Chemical Industry Co., Ltd., Kao Corp., Riken Vitamin Co., Ltd. (all Japan), etc. Oleyl glyceryl is commercially available, for example, under a trade name of NIKKOL Selachyl Alcohol V from Nikko Chemicals Co., Ltd. (Japan). Isostearyl glyceryl is commercially available, for example, under a trade name of Penetol GE-IS from Kao Corp. (Japan).

The external preparation according to the present invention comprises the non-lamellar liquid crystal-forming lipid in an effective amount. The amount of the non-lamellar liquid crystal-forming lipid contained in the external preparation according to the present invention may be, but not limited to, usually 0.1 w/w % or more or 0.5 w/w % or more, for example, 3 w/wo or more, 5 w/w % or more, 0.5 to 99.8 w/w %, 1 to 99.5 w/w %, 5 to 99 w/w %, 10 to 99.8 w/w %, 40 to 99.8 w/w %, 60 w/w % or more, 70 w/w % or more, 60 to 99.8 w/w %, 65 to 99.8 w/w %, 68 to 99 w/w %, 70 to 99.5 w/w %, 70 to 90 w/wo, 10 to 30 w/w %, 10 to 25 w/w %, 13 to 15 w/w %, 3 to 20 w/w %, 3 to 15 w/w %, 3 to 10 w/w %, or 5 to 9 w/w %, relative to the total weight of the external preparation.

In this context, the "total weight of the external preparation" refers to the total weight of a composition (preferably a mixed or dispersed composition) comprising at least the non-lamellar liquid crystal-forming lipid and a drug for use as the external preparation, and the weights of other constituent members such as a support which places the composition thereon and a container which houses the composition are excluded from the "total weight".

2. Drug

The drug contained in the external preparation according to the present invention is released to a living body surface, permeates through (passes through) the skin, the mucosa, or the like, and absorbed into the body, by the application of the external preparation to the living body surface. The drug may be any substance (active ingredient) to be administered to a living body, provided that the drug is not the non-lamellar liquid crystal-forming lipid itself. The drug may be an organic compound or may be an inorganic compound. The drug may be a water soluble drug or may be a lipid soluble (lipophilic, water insoluble or poorly water soluble) drug. The drug may be a physiologically active substance. The drug may be, but not limited to, for example, a protein, a peptide, an amino acid, or a nucleic acid. The drug may be, but not limited to, for example, an anticancer agent, an immunosuppressant, an analgesic (e.g., non-opioid analgesic drugs and opioid analgesic drugs such as morphine), an anti-inflammatory agent, an antiallergic agent (tranilast, etc.), a steroid drug (triamcinolone acetonide, etc.), an anti-obesity drug, an antidiabetic drug, an antibiotic, an antifungal agent, an antiviral agent, a vasodilator, an anesthetic, an anti-smoking drug (nicotine, etc.), an antipsychotic drug, a hypotensive agent, a cardiotonic, a P blocker, an antianemic agent, an antihyperlipidemic agent, a bronchodilator, a therapeutic drug for dementia, a therapeutic drug for a brain or central nervous system disease such as Alzheimer's disease, Parkinson's disease, cerebrovascular disorder, or brain tumor, a therapeutic drug for chronic obstructive pulmonary disease (COPD), a therapeutic drug for glaucoma, a therapeutic drug for cataract, a therapeutic drug for age-related macular degeneration, a therapeutic drug for overactive bladder, a therapeutic drug for attention-deficit hyperactivity disorder, a hormone agent, or a vaccine.

3. Dosage Form and Composition of External Preparation

The external preparation according to the present invention may be for systemic administration or for local administration. The external preparation according to the present invention may be formulated in any dosage form. The external preparation according to the present invention may have a dosage form including, but not limited to: patches, for example, tape formulations (also referred to as plaster formulations) and cataplasms; spray formulations, for example, aerosol formulations and pump spray formulations (manual or mechanical sprays); and others such as ointments, creams, buccals, transnasal formulations, suppositories, and vaginal suppositories. The spray formulation refers to a pharmaceutical formulation in a dosage form that enables a drug to be ejected by pressure applied manually, via mechanical power, with a propellant (gas), or by any of other means. The external preparation according to the present invention may comprise fine particles (e.g., microparticles or nanoparticles) comprising the non-lamellar liquid crystal-forming lipid and the drug. The external preparation according to the present invention may be a dispersion or may comprise, for example, a dispersion liquid of the fine particles (e.g., microparticles or nanoparticles). The present invention also provides such a formulation in any dosage form comprising the external preparation according to the present invention.

The external preparation according to the present invention may be for use in application to a living body surface, preferably the skin (skin surface). Alternatively, the external preparation according to the present invention may be for use in application to the mucosa (mucosal surface). The external preparation according to the present invention can promote the permeation of the drug through the skin or the mucosa. The external preparation according to the present invention is suitable not only for skin application but for mucosal application.

The external preparation according to the present invention may comprise an aqueous medium as an additional component. The aqueous medium may be, but not limited to, for example, water such as sterile water, purified water, distilled water, ion exchanged water, or ultrapure water; an electrolyte aqueous solution such as physiological saline, an aqueous sodium chloride solution, an aqueous calcium chloride solution, an aqueous magnesium chloride solution, an aqueous sodium sulfate solution, an aqueous potassium sulfate solution, an aqueous sodium carbonate solution, or an aqueous sodium acetate solution; or a buffer solution such as a phosphate buffer and a Tris-HCl buffer. The aqueous medium is preferably physiologically acceptable water or aqueous solution. The aqueous medium may contain, for example, a component of the external preparation, such as the drug, dissolved, dispersed, or suspended therein.

The external preparation according to the present invention may comprise a water soluble polymer as an additional component. Examples of the water soluble polymer include, but are not limited to, hydroxypropylcellulose (HPC), hydroxyethylcellulose, polyvinylpyrrolidone, Carbopol, carrageenan, chitosan, chondroitin sulfate salt, xanthan gum, hyaluronic acid salt (sodium hyaluronate, etc.), alginic acid salt (sodium alginate, etc.), gelatin, and dextran. Examples of the hydroxypropylcellulose (HPC) include HPC of 5 grades: HPC-SSL (molecular weight: about 40,000, viscosity: 2 to 2.9 mpa·s), HPC-SL (molecular weight: about 100,000, viscosity: 3 to 5.9 mpa·s), HPC-L (molecular weight: about 140,000, viscosity: 6 to 10 mpa·s), HPC-M (molecular weight: about 620,000, viscosity: 150 to 400 mpa·s), and HPC-H (molecular weight: about 910,000, viscosity: 1000 to 4000 mpa·s), commercially available from Nippon Soda Co., Ltd. (Japan). In one embodiment, the hydroxypropylcellulose may have a molecular weight of 1000,000 or lower or 800,000 or lower, for example, 10,000 to 700,000 or 10,000 to 80,000.

The amount of the drug contained in the external preparation according to the present invention may be, but not limited to, typically 0.0001 w/w % or more, for example, 0.0001 to 10 w/w %, 0.0005 to 5 w/w %, 0.0005 to 1 w/w %, 0.001 to 5 w/w %, 0.001 to 1 w/w %, 0.001 to 0.1 w/w %, 0.001 to 0.05 w/w %, 0.001 to 0.01 w/w %, 0.01 to 5 w/w %, 0.01 to 1 w/w %, 0.01 to 0.1 w/w %, 0.05 to 1 w/w %, or 0.1 to 0.5 w/w %, relative to the total weight of the external preparation. The "total weight of the external preparation" is as defined above. In the present invention, w/w % means weight/weight % and is interchangeably used with mass/mass %.

The external preparation according to the present invention may comprise an oil as an additional component. Examples of the oil include, but are not limited to: fats and oils such as hydrocarbon oil, ester oil, and plant or animal oil; higher alcohols such as behenyl alcohol and stearyl alcohol; higher fatty acids such as stearic acid and palmitic acid; and lipid soluble vitamins. Specific examples of the oil include, but are not limited to, squalene, squalane, isopropyl myristate, octyl dodecyl myristate, castor oil, olive oil, tocopherol, and tocopherol acetate.

The external preparation of the present invention may comprise a surfactant as an additional component. Examples of the surfactant used in the present invention include nonionic surfactants including block copolymers of hydrophilic ethylene oxide and hydrophobic propylene oxide (polyoxyethylene polyoxypropylene glycol), polyoxyethylene alkyl ether, polyoxyethylene alkyl ester, and polyoxyethylene hydrogenated castor oil. The nonionic surfactant more preferably has a molecular weight of 1000 or higher (more preferably 5000 or higher). Examples of the block copolymer of ethylene oxide and propylene oxide include polyoxyethylene(200) polyoxypropylene(70) glycol, polyoxyethylene(196) polyoxypropylene(67) glycol, polyoxyethylene(160) polyoxypropylene(30) glycol, and polyoxyethylene(120) polyoxypropylene(40) glycol. These block copolymers of ethylene oxide and propylene oxide are commercially available under various names such as Pluronic®, Poloxamer®, Unilube®, and Pronon®. Particularly preferred examples of the surfactant include, but are not limited to, polyoxyethylene(200) polyoxypropylene(70) glycol and polyoxyethylene(196) polyoxypropylene(67) glycol (also called Pluronic® F127, Unilube 70DP-950B, and Poloxamer®407). In the present invention, the non-lamellar liquid crystal-forming lipid used in the present invention is not included in the scope of the surfactant. The external preparation of the present invention may comprise one or two or more of such surfactants.

The external preparation of the present invention may comprise typically 0.001 w/w % or more, for example, 0.01 w/w % or more, preferably 0.05 w/w % or more, more preferably 0.1 w/w % or more, for example, 0.01 to 10 w/w %, 0.1 to 5 w/w %, 0.3 w/w % or more, 0.3 to 2 w/w %, 0.3 to 1.5 w/w %, 0.3 to 1 w/w %, or 0.55 to 0.9 w/w %, of the surfactant relative to the total weight of the external preparation.

The external preparation according to the present invention may comprise ethanol (which refers to anhydrous ethanol in the present invention, unless otherwise specified) as an additional component. The ethanol (anhydrous ethanol) is not an aqueous medium.

The external preparation according to the present invention may comprise a pharmaceutically acceptable water soluble organic compound such as propylene glycol, glycerin, ethylene glycol, or butylene glycol as an additional component.

The external preparation according to the present invention may comprise other pharmaceutically acceptable additive(s) as an additional component. Examples of the additive include, but are not limited to, carriers, excipients, stabilizers, buffering agents, preservatives, coloring agents, flavoring agents, pH adjusters, and dispersants.

The non-lamellar liquid crystal-forming lipid may or may not form liquid crystals (particularly, non-lamellar liquid crystals), in the external preparation according to the present invention. When the non-lamellar liquid crystal-forming lipid forms no liquid crystal in the external preparation, this external preparation is also referred to as a liquid crystal precursor formulation. Since the non-lamellar liquid crystal-forming lipid forms no liquid crystal in the external preparation according to the present invention containing no aqueous medium or an insufficient amount of an aqueous medium, such an external preparation is a liquid crystal precursor formulation.

The drug contained in the external preparation according to the present invention can be administered to a living body by the application of the external preparation to a living body surface, preferably the skin or the mucosa. The present invention also provides a drug delivery method or a drug administration method comprising applying the external preparation according to the present invention to a living body surface, preferably the skin or the mucosa. The subject to which the external preparation according to the present invention is applied is not particularly limited and is typically an animal, preferably a mammal including primates such as humans, livestock, pet animals such as dogs, cats, and rabbits, and laboratory animals, or bird.

Hereinafter, the external preparation in a preferred dosage form will be described in more detail.

4. Patch

The external preparation according to the present invention may be formulated in a dosage form of a patch. The present invention also provides a patch comprising the external preparation according to the present invention. In the present invention, the patch refers to a pharmaceutical formulation that is attached to the skin or the mucosa for use and intended for the transdermal or transmucosal absorption of a drug. The patch may act locally or may act systemically. The patch has an adhesive layer. The adhesive layer of the patch is preferably a composition comprising an adhesive (more preferably a lipid soluble adhesive) and preferably comprises the adhesive as well as the non-lamellar liquid crystal-forming lipid and the drug. Examples of the patch include, but are not limited to, tape formulations (also referred to as plaster formulations) and cataplasms.

The tape formulation is a formulation having an adhesive layer using a pressure sensitive adhesive as a base. The adhesive layer is preferably a composition comprising the pressure sensitive adhesive, the non-lamellar liquid crystal-forming lipid and the drug. In one embodiment, the tape formulation has an adhesive layer comprising the pressure sensitive adhesive, the non-lamellar liquid crystal-forming lipid and the drug, and a support. In a preferred embodiment, the tape formulation is a so-called matrix formulation having an adhesive layer comprising the pressure sensitive adhesive, the non-lamellar liquid crystal-forming lipid and the drug, a liner (release sheet), and a support. The pressure sensitive adhesive for use in the tape formulation is preferably a lipid soluble polymer. Examples of the pressure sensitive adhesive include, but are not limited to, acrylic, urethane, rubber, and silicon adhesives. Examples of the acrylic adhesive include, but are not limited to, DURO-TAK® (Henkel AG & Co. KGaA), for example, DURO-TAK® 387-2516.

The support may have any shape that can be used in the patch, and is preferably a base material in a sheet form. For example, a support known in the art can be used as the support. The support may be, for example, any material suitable as a support for patches, and may be, for example, a film such as a polymer film, a fabric such as a nonwoven fabric or a woven fabric, or paper. The support may be constituted by, for example, polyester, polyethylene (polyethylene terephthalate, polyethylene naphthalate, polybutylene terephthalate, etc.), polyolefin (polyethylene, polypropylene, etc.), a cellulose derivative such as cellulose ester, polyurethane, or polyamide. The thickness of the support is, but not limited to, generally 5 μm to 500 μm, preferably 10 to 300 μm, for example, 10 to 200 μm, 10 to 100 μm, 25 to 100 μm, 50 μm to 300 μm, or 60 μm to 200 μm.

Any release sheet that may be used in the patch can be used. For example, a release film known in the art can be used. The release sheet may be constituted by, for example, a polymer film such as polyester (polyethylene terephthalate, polyethylene naphthalate, polybutylene terephthalate, etc.), polyolefin (polyethylene, polypropylene, etc.), polyvinyl chloride, or polyvinylidene chloride, a cellulose derivative such as cellulose ester, or paper, or a laminate film made of a plurality of materials selected therefrom, wherein a contact surface with the adhesive layer has a layer of fluorine resin, silicone resin, or the like. The thickness of the release sheet is, but not limited to, generally 5 to 500 μm, preferably 10 to 300 μm, for example, 10 to 200 μm, 25 to 100 μm, 50 μm to 300 μm, or 60 μm to 200 μm.

The thickness of the adhesive layer in the patch is, but not limited to, generally 5 μm to 1 mm, preferably 5 to 500 μm, for example, 5 to 200 μm, 10 to 100 μm, or 20 to 50 μm.

The non-lamellar liquid crystal-forming lipid and the drug are as mentioned above.

In one embodiment, the amount of the non-lamellar liquid crystal-forming lipid in the adhesive layer of the patch, for example, the tape formulation, is preferably an amount that allows liquid crystals to be formed. The non-lamellar liquid crystal-forming lipid is as mentioned above. More specifically, the amount of the non-lamellar liquid crystal-forming lipid in the adhesive layer is, but not limited to, usually 0.1 w/w % or more, preferably 5 w/w % or more, for example, 1 to 20 w/w %, 1 to 10 w/w %, 5 to 20 w/w %, 5 to 10 w/w %, 10 to 30 w/w %, 10 to 25 w/w %, or 13 to 15 w/w %, relative to the total weight of the adhesive layer.

The amount of the drug in the adhesive layer is, but not limited to, usually 0.0001 w/w % or more, preferably 0.0005 to 5 w/w %, more preferably 0.001 to 5 w/w %, for example, 0.001 to 1 w/w %, 0.01 to 1 w/w %, 0.05 to 1 w/w %, or 0.1 to 0.5 w/w %, relative to the total weight of the adhesive layer.

The amount of the adhesive (e.g., a pressure sensitive adhesive) in the adhesive layer is, but not limited to, typically 70 w/w % or more, preferably 75 w/w % or more, more preferably 75 to 90 w/w %, 75 to 85 w/w %, 80 to 95 w/w %, 85 to 95 w/wo, or 85 to 90 w/wo, for example, 80 w/w % or 90 w/w %, relative to the total weight of the adhesive layer.

In one embodiment, the amounts of the non-lamellar liquid crystal-forming lipid and the adhesive in the adhesive layer of the patch, for example, the tape formulation, may be, but not limited to, 1 to 20 w/w % and 75 to 90 w/w %, respectively, relative to the total weight of the adhesive layer. In another embodiment, the amounts of the non-lamellar liquid crystal-forming lipid and the adhesive in the adhesive layer of the patch, for example, the tape formulation, may be, but not limited to, 1 to 10 w/w % and 85 to 95 w/w %, respectively, relative to the total weight of the adhesive layer. In an alternative embodiment, the amounts of the non-lamellar liquid crystal-forming lipid and the adhesive in the adhesive layer of the patch, for example, the tape formulation, may be, but not limited to, 10 to 15 w/w % and 75 to 85 w/w %, respectively, relative to the total weight of the adhesive layer. In a further alternative embodiment, the amounts of the non-lamellar liquid crystal-forming lipid and the adhesive in the adhesive layer of the patch, for example, the tape formulation, may be, but not limited to, 13 to 15 w/w % and 75 to 85 w/w %, respectively, relative to the total weight of the adhesive layer.

The adhesive layer of the patch, for example, the tape formulation, preferably comprises an aqueous medium (e.g., water) together with the non-lamellar liquid crystal-forming lipid and the drug. By comprising the aqueous medium, the non-lamellar liquid crystal-forming lipid forms liquid crystals in the patch so that the drug is enclosed in the liquid crystals. The aqueous medium is as mentioned above. Alternatively, the patch itself may not comprise an aqueous medium. In this case, the non-lamellar liquid crystal-forming lipid may form liquid crystals on a living body surface in the presence of surrounding water upon application of the patch to the living body surface so that the drug is enclosed in the liquid crystals. In one embodiment, the aqueous medium may be contained, as a liquid comprising the drug or other components, in an adhesive layer composition. The amount of the aqueous medium in the adhesive layer is, but not limited to, usually 0.1 w/w % or more, preferably 0.5 w/w % or more, more preferably 1 w/w % or more, for example, 5 w/w % or more, 3 to 30 w/w %, 5 to 10 w/w %, 10 to 30 w/w %, 10 to 25 w/w %, or 13 to 15 w/w %, relative to the total weight of the adhesive layer. In one embodiment, the weight ratio between the non-lamellar liquid crystal-forming lipid and the aqueous medium in the adhesive layer may be preferably 1:5 to 5:1, for example, 1:1 to 10:1, 1:1 to 5:1, 1:1 to 3:1, 1.5:1 to 10:1, or 2:1 to 5:1. A preferred example thereof is a weight ratio of 2:1 to 3:1. The weight ratio between the non-lamellar liquid crystal-forming lipid and the adhesive in the adhesive layer may be, for example, 1:2 to 1:20 and is preferably 1:2 to 1:15, 1:3 to 1:10, 1:3 to 1:8, or 1:5 to 1:7.

The adhesive layer may comprise an additional component. The additional component is as mentioned above about the external preparation according to the present invention.

The patch, for example, the tape formulation, may be produced by use of a technique known to persons skilled in the art. In one embodiment, the patch, for example, the tape formulation, can be produced by homogeneously mixing the non-lamellar liquid crystal-forming lipid, the drug, and the aqueous medium, and optionally, the additional component to prepare a liquid crystal gel, then mixing the adhesive therewith to prepare an adhesive layer composition, spreading the adhesive layer composition over a liner, drying an adhesive layer, pressure-bonding the adhesive layer onto a support for fixation, and, if necessary, cutting out a given size. Alternatively, the patch, for example, the tape formulation, can be produced by mixing the adhesive with the liquid crystal gel prepared as described above to prepare an adhesive layer composition, spreading the adhesive layer composition over a support, drying an adhesive layer, then laminating the adhesive layer with a liner, and, if necessary, cutting out a given size. The patch, for example, the tape formulation may be prepared with a size and/or a shape suitable for application to an affected area, or may be prepared with a predetermined size and/or shape which is to be cut into an appropriate size and/or shape when used.

The drug in such a patch, for example, a tape formulation, is incorporated into liquid crystals formed by the non-lamellar liquid crystal-forming lipid, and functions to increase drug permeability through the skin or the mucosa when the patch is applied to a living body surface such as the skin or the mucosa.

The patch, for example, the tape formulation, according to the present invention is applied (worn) to a living body surface, preferably the skin or the mucosa, of a subject (e.g., a mammal) and can thereby transdermally or transmucosally administer the drug contained in the patch to the subject. The subject is as mentioned above. The present invention also provides such a drug administration method or drug delivery method.

5. Aerosol Formulation

The external preparation according to the present invention may be formulated in a dosage form of an aerosol formulation. The present invention also provides an aerosol formulation comprising the external preparation according to the present invention. In the present invention, the aerosol formulation refers to a pharmaceutical formulation in a dosage form that enables a drug to be ejected by pressure applied with a propellant filled together with the drug into a container. The external preparation according to the present invention formulated in a dosage form of an aerosol formulation comprises a composition comprising the non-lamellar liquid crystal-forming lipid and the drug, and a propellant. The propellant is, for example, liquefied gas and/or compressed gas. Examples of the liquefied gas include liquefied petroleum gas (LPG) and dimethyl ether (DME). Examples of the compressed gas include carbon dioxide, nitrogen, and air. In the aerosol formulation according to the present invention, the propellant is more preferably liquefied gas, further preferably LPG.

In the aerosol formulation according to the present invention, the composition comprising the non-lamellar liquid crystal-forming lipid and the drug, and the propellant are preferably filled into a container. The composition comprising the non-lamellar liquid crystal-forming lipid and the drug is preferably a liquid and is preferably in an aqueous state. In other words, the external preparation according to the present invention formulated in a dosage form of an aerosol formulation preferably comprises an aqueous medium, in addition to the non-lamellar liquid crystal-forming lipid, the drug, and the propellant. By comprising the aqueous medium, the non-lamellar liquid crystal-forming lipid forms liquid crystals so that the drug is enclosed in the liquid crystals. Alternatively, the external preparation according to the present invention formulated in a dosage form of an aerosol formulation may not comprise an aqueous medium. In this case, the non-lamellar liquid crystal-forming lipid in the external preparation forms non-lamellar liquid crystals with an aqueous medium present in an application site (e.g., water in the body, or foreign water such as added water) so that the drug is enclosed in the liquid crystals. When the aerosol formulation according to the present invention is applied to a living body surface, non-lamellar liquid crystals can be formed on the living body surface by the volatilization of a volatile component (a solvent such as ethanol, a propellant, etc.) in the aerosol formulation. In the aerosol formulation according to the present invention, the composition comprising the non-lamellar liquid crystal-forming lipid and the drug, and the propellant may be a mixture or a plurality of separate phases in a container. The non-lamellar liquid crystal-forming lipid, the drug, and the aqueous medium are as mentioned above.

In one embodiment, the amount of the non-lamellar liquid crystal-forming lipid used in the aerosol formulation is, but not limited to, usually 0.1 w/w % or more, preferably 0.5 w/w % or more, more preferably 1 w/w % or more, for example, 1 to 40 w/w %, 3 w/w % or more, 3 to 40 w/w %, 3 to 20 w/w %, 3 to 15 w/w %, 3 to 10 w/w %, 10 to 30 w/w %, or 5 to 9 w/w %, relative to the total weight of aerosol raw materials filled into a container, typically the total weight in which the weights of the composition comprising the non-lamellar liquid crystal-forming lipid and the drug, and the propellant are summated (the total weight of the external preparation; the same holds true for the description below).

In one embodiment, the amount of the drug used in the aerosol formulation is, but not limited to, usually 0.0001 w/w % or more, preferably 0.0005 to 5 w/w %, for example, 0.0005 to 1 w/w %, 0.001 to 5 w/w %, 0.001 to 10 w/w %, 0.001 to 1 w/wo, 0.001 to 0.1 w/w %, 0.001 to 0.05 w/wo, 0.001 to 0.01 w/w %, 0.01 to 0.1 w/w %, 0.1 to 3 w/w %, or 0.1 to 1 w/w %, relative to the total weight of aerosol raw materials filled into a container, typically the total weight in which the weights of the composition comprising the non-lamellar liquid crystal-forming lipid and the drug, and the propellant are summated.

In one embodiment, the amount of the propellant used in the aerosol formulation is, but not limited to, usually 40 w/w % or more, preferably 50 w/w % or more, for example, 50 to 90 w/w %, 50 to 85 w/w %, 50 to 80 w/w %, 60 to 85 w/w %, 60 to 80 w/w %, 60 to 70 w/w %, or 65 to 75 w/w %, relative to the total weight of aerosol raw materials filled into a container, typically the total weight in which the weights of the composition comprising the non-lamellar liquid crystal-forming lipid and the drug, and the propellant are summated.

In one embodiment, the amount of the aqueous medium used in the aerosol formulation is, but not limited to, usually 0.1 w/w % or more, preferably 0.5 w/w % or more, more preferably 1 w/w % or more, for example, 3 w/w % or more, 5 w/w % or more, 0.1 to 30 w/w %, 1 to 30 w/w %, 3 to 30 w/w %, 3 to 20 w/w %, 3 to 15 w/w %, 1 to 10 w/w %, 3 to 10 w/w %, 5 to 10 w/w %, or 5 to 9 w/w %, relative to the total weight of aerosol raw materials filled into a container, typically the summated weights of the composition comprising the non-lamellar liquid crystal-forming lipid and the drug, and the propellant.

In one embodiment, the weight ratio between the non-lamellar liquid crystal-forming lipid and the aqueous medium may be preferably 1:5 to 5:1, 1:2 to 2:1, or 1:1.5 to 1.5:1, for example, 1:1.3 to 1.3:1 or 1:1.1 to 1.1:1. One preferred example thereof is a weight ratio of 1:1. Alternatively, the weight ratio between the non-lamellar liquid crystal-forming lipid and the aqueous medium may be 1:1 to 10:1 or 1.5:1 to 5:1, for example, 1:1, 1.5:1, 2:1, 3:1, 4:1, or 5:1.

The external preparation according to the present invention formulated in a dosage form of an aerosol formulation may or may not further comprise a surfactant. In one embodiment, the composition comprising the non-lamellar liquid crystal-forming lipid and the drug comprises a surfactant. The surfactant is as mentioned above. A preferred example of the surfactant for use in the aerosol formulation is, but not limited to, polyoxyethylene(196) polyoxypropylene(67) glycol (also called Pluronic® F127). In one embodiment, the amount of the surfactant used in the aerosol formulation is, but not limited to, usually 0.01 w/w % or more, preferably 0.05 w/w % or more, more preferably 0.1 w/w % or more, for example, 0.05 w/w % to 15 w/w %, 0.1 to 5 w/w %, 0.3 w/w % or more, 0.3 to 10 w/w %, 0.3 to 2 w/w %, 0.3 to 1.5 w/w %, 0.3 to 1 w/w %, or 0.55 w/w % to 0.9 w/w %, relative to the total weight of aerosol raw materials filled into a container, typically the summated weights of the composition comprising the non-lamellar liquid crystal-forming lipid and the drug, and the propellant.

In one embodiment, the weight ratio between the non-lamellar liquid crystal-forming lipid and the surfactant in the aerosol formulation may be preferably 3:1 to 20:1 or 5:1 to 20:1, for example, 3:1 to 11:1, 7:1 to 17:1, or 8:1 to 15:1, 8:1 to 13:1, or 9:1 to 11:1. One preferred example thereof is a weight ratio of 10:1.

The external preparation according to the present invention formulated in a dosage form of an aerosol formulation preferably further comprises ethanol. The composition comprising the non-lamellar liquid crystal-forming lipid and the drug comprises ethanol. By containing ethanol, drug permeability through the skin is further increased.

In one embodiment, the amount of the ethanol used in the aerosol formulation may be, but not limited to, 1 w/w % or more, and is preferably 3 w/w % or more, for example, 5 w/w % or more, 7 w/w % or more, 1 to 30 w/w %, 1 to 20 w/w %, 5 to 60 w/w %, 5 to 30 w/w %, 5 to 25 w/w %, 7 to 20 w/w %, 10 to 20 w/w %, 13 to 50 w/w %, 13 to 20 w/w %, or 15 to 18 w/w %, relative to the total weight of aerosol raw materials filled into a container, typically the summated weights of the composition comprising the non-lamellar liquid crystal-forming lipid and the drug, and the propellant.

In one embodiment, the amount of the ethanol relative to the total weight of the composition comprising the non-lamellar liquid crystal-forming lipid and the drug (excluding the propellant) may be, but not limited to, for example, 20 to 60 w/w % or 30 to 50 w/w %.

In one embodiment, the external preparation according to the present invention formulated in a dosage form of an aerosol formulation may comprise the drug, the non-lamellar liquid crystal-forming lipid (e.g., an amphipathic compound represented by the general formula (I) or glycerin fatty acid monoester, preferably mono-O-(5,9,13-trimethyl-tetradec-4-enoyl)glycerol or mono-O-(5,9,13,17-tetramethyloctadec-4-enoyl)glycerol), a surfactant (preferably Pluronic® F127), ethanol, and the propellant (preferably LPG). In this case, the amount of the ethanol relative to the total weight of aerosol raw materials filled into a container, typically the summated weights of the composition comprising the non-lamellar liquid crystal-forming lipid and the drug, and the propellant may be as described above and is preferably 5 to 25 w/w %, 13 to 20 w/w %, or 15 to 18 w/w %. In this case, the amount of the propellant relative to the total weight of aerosol raw materials filled into a container, typically the summated weights of the composition comprising the non-lamellar liquid crystal-forming lipid and the drug, and the propellant is preferably 50 to 85 w/w %, 60 to 80 w/w %, or 60 to 70 w/w %. In one embodiment, the amount of the ethanol and the amount of the propellant relative to the total weight of aerosol raw materials filled into a container, typically the summated weights of the composition comprising the non-lamellar liquid crystal-forming lipid and the drug, and the propellant may be 5 to 25 w/w % and 60 to 80 w/w %, respectively. In one embodiment, the amount of the ethanol and the amount of the propellant relative to the total weight of aerosol raw materials filled into a container, typically the summated weights of the composition comprising the non-lamellar liquid crystal-forming lipid and the drug, and the propellant may be 15 to 18 w/w % and 60 to 70 w/w %, respectively.

The external preparation according to the present invention formulated in a dosage form of an aerosol formulation may further comprise an additional component. Such an additional component is basically contained in the composition comprising the non-lamellar liquid crystal-forming lipid and the drug. The additional component is as mentioned above about the external preparation according to the present invention.

The aerosol formulation can be produced by use of a technique known to persons skilled in the art. In one embodiment, the aerosol formulation can be produced by homogeneously mixing the non-lamellar liquid crystal-forming lipid, the drug, the aqueous medium, and optionally, the surfactant and the additional component, further mixing therewith optionally added ethanol to prepare a composition, placing the composition as an aerosol stock solution in a container, and subsequently filling the propellant into the container using a gas filling valve or the like. In another embodiment, the non-lamellar liquid crystal-forming lipid, the drug, and optionally, the surfactant and the additional component are homogenously mixed and further mixed with optionally added ethanol to prepare a composition, which may be used as an aerosol stock solution.

Liquid crystals enclosing the drug, stably formed and attached at an application site on a living body surface by the spraying of such an aerosol formulation bring about excellent drug permeability.

The aerosol formulation according to the present invention is applied (sprayed) to a living body surface, preferably the skin or the mucosa, of a subject (e.g., a mammal) and can thereby transdermally or transmucosally administer the drug contained in the aerosol formulation to the subject. The subject is as mentioned above. The present invention also provides such a drug administration method or drug delivery method.

6. Liquid Crystal Precursor Formulation

The external preparation according to the present invention may be an external preparation in which the non-lamellar liquid crystal-forming lipid forms no liquid crystal (non-lamellar liquid crystal). When the external preparation according to the present invention comprises no aqueous medium or comprises an aqueous medium in an amount insufficient for forming liquid crystals by the non-lamellar liquid crystal-forming lipid, the non-lamellar liquid crystal-forming lipid forms no liquid crystal in the external preparation. However, when such an external preparation is applied to a living body surface in the presence of water, the non-lamellar liquid crystal-forming lipid forms liquid crystals on the living body surface so that the liquid crystals are stably attached to the living body surface. The present invention also provides the external preparation according to the present invention in which the non-lamellar liquid crystal-forming lipid forms no liquid crystal, i.e., a liquid crystal precursor formulation.

The external preparation according to the present invention which is a liquid crystal precursor formulation is preferably a composition comprising the non-lamellar liquid crystal-forming lipid and the drug while comprising no aqueous medium or comprising an aqueous medium in an insufficient amount. The non-lamellar liquid crystal-forming lipid, the drug, and the aqueous medium are as mentioned above.

In one embodiment, the amount of the non-lamellar liquid crystal-forming lipid used in the liquid crystal precursor formulation may be, but not limited to, 10 w/w % or more, and is preferably 30 w/w % or more or 50 w/w % or more, more preferably 60 w/w % or more, for example, 70 w/w % or more, 50 to 99.8 w/w % or more, 60 to 99.8 w/w % or more, 65 to 99.8 w/w %, 65 to 99.5 w/w %, 68 to 99 w/w %, 70 to 99.5 w/w %, 50 to 90 w/w %, or 70 to 90 w/w %, relative to the total weight of the liquid crystal precursor formulation (external preparation).

In one embodiment, the amount of the drug used in the liquid crystal precursor formulation is, but not limited to, usually 0.0001 w/w % or more, preferably 0.0001 to 10 w/w %, for example, 0.0005 to 5 w/w %, 0.0005 to 1 w/w %, 0.001 to 5 w/w %, 0.001 to 1 w/w %, or 0.001 to 0.1 w/w %, relative to the total weight of the liquid crystal precursor formulation (external preparation).

The external preparation according to the present invention which is a liquid crystal precursor formulation preferably further comprises a water soluble polymer. The water soluble polymer is as mentioned above. Preferred examples of the water soluble polymer include, but are not limited to, hydroxypropylcellulose (HPC), for example, HPC-SSL, HPC-SL, HPC-L, HPC-M, and HPC-H.

In one embodiment, the amount of the water soluble polymer in the liquid crystal precursor formulation may be, but not limited to, 0.01 w/w % or more, and is preferably 0.1 w/w % or more, for example, 0.1 to 10 w/w %, 1 to 5 w/w %, or 0.5 to 2 w/w %, relative to the total weight of the liquid crystal precursor formulation (external preparation).

The external preparation according to the present invention which is a liquid crystal precursor formulation may or may not further comprise ethanol. In one embodiment, the amount of the ethanol in the liquid crystal precursor formulation may be, but not limited to, 1 w/w % or more, and is preferably 4 w/w % or more, for example, 5 to 40 w/w %, 5 to 30 w/w %, or 10 to 30 w/w %, relative to the total weight of the liquid crystal precursor formulation (external preparation).

The external preparation according to the present invention which is a liquid crystal precursor formulation may or may not further comprise an oil. The oil is as mentioned above. Preferred examples of the oil include, but are not limited to, squalene, squalane, isopropyl myristate, and tocopherol. In one embodiment, the amount of the oil in the liquid crystal precursor formulation may be, but not limited to, 0.01 w/w % or more, and is, for example, 0.01 to 60 w/w %, 0.1 to 40 w/w %, 1 to 30 w/w %, 1 to 10 w/w %, or 1 to 8 w/w %, relative to the total weight of the liquid crystal precursor formulation (external preparation).

In one embodiment, the external preparation according to the present invention which is a liquid crystal precursor formulation may comprise the drug; the non-lamellar liquid crystal-forming lipid (e.g., an amphipathic compound represented by the general formula (I) or glycerin fatty acid monoester, preferably mono-O-(5,9,13-trimethyltetradec-4-enoyl)glycerol or mono-O-(5,9,13,17-tetramethyloctadec-4-enoyl)glycerol); the water soluble polymer (preferably hydroxypropylcellulose); and ethanol.

The external preparation according to the present invention which is a liquid crystal precursor formulation may further comprise an additional component. The additional component is as mentioned above about the external preparation according to the present invention.

The liquid crystal precursor formulation may be produced by use of a technique known to persons skilled in the art. The liquid crystal precursor formulation can be produced by thoroughly mixing the raw materials described above. In one embodiment, the liquid crystal precursor formulation can be produced by thoroughly mixing the non-lamellar liquid crystal-forming lipid, the water soluble polymer, ethanol, and optionally, the oil, etc., adding the drug thereto, and thoroughly mixing these materials. Alternatively, the liquid crystal precursor formulation may be produced by thoroughly mixing the drug, ethanol, and optionally, the water soluble polymer, and the oil, etc., adding the non-lamellar liquid crystal-forming lipid thereto, and thoroughly mixing these materials. Also, the liquid crystal precursor formulation may be produced by merely thoroughly mixing the non-lamellar liquid crystal-forming lipid, the drug, the water soluble polymer, and the oil, etc.

Such a liquid crystal precursor formulation forms liquid crystals enclosing the drug in the presence of water upon application to a living body surface so that the liquid crystals are stably attached to an application site and bring about excellent drug permeability.

The liquid crystal precursor formulation according to the present invention may be applied to the skin or is preferably applied to the mucosa. When the liquid crystal precursor formulation according to the present invention is applied to the mucosa, the non-lamellar liquid crystal-forming lipid comes into contact with water derived from the living body, causing self-formation of liquid crystals (non-lamellar liquid crystals) by the non-lamellar liquid crystal-forming lipid on the mucosal surface. As a result, the liquid crystals enclosing the drug are stably attached to the mucosa and bring about excellent drug permeability through the mucosa. Thus, the present invention provides not only a skin application formulation but a mucosal application formulation. The external preparation according to the present invention which is a liquid crystal precursor formulation is particularly preferred for mucosal application.

The liquid crystal precursor formulation according to the present invention is applied (e.g., sprayed, spread, or added dropwise) to a living body surface, preferably the mucosa or the skin, of a subject (e.g., a mammal) and can thereby transmucosally or transdermally administer the drug contained in the liquid crystal precursor formulation to the subject. The liquid crystal precursor formulation according to the present invention, when applied to the skin, is preferably applied to the skin wetted with an aqueous medium in advance, or applied to the skin, followed by the addition of an aqueous medium to the formulation. The subject and the aqueous medium are as mentioned above. The present invention also provides such a drug administration method or drug delivery method.

7. External Preparation Containing Fine Particle

The present invention also provides an external preparation comprising fine particles comprising the non-lamellar liquid crystal-forming lipid and the drug. The external preparation according to the present invention may be a dispersion such as a dispersion liquid (emulsion). The external preparation according to the present invention may comprise a dispersion, for example, a dispersion liquid, of fine particles (fine particle dispersion liquid) comprising the non-lamellar liquid crystal-forming lipid and the drug. The dispersion, for example, the dispersion liquid comprises the non-lamellar liquid crystal-forming lipid and the drug in a dispersion medium, for example, an aqueous medium such as water, and preferably further comprises a dispersing agent such as a surfactant. The dispersion, for example, the dispersion liquid may optionally further comprise a solvent such as ethanol, and/or an oil.

In the present invention, the "fine particles" refer to particles having an average particle size (in diameter) of less than 1 mm. The "fine particles" according to the present invention may be microparticles or nanoparticles. In the present invention, the "microparticles" refer to particles having an average particle size of 1 µm or more and less than 1 mm. In the present invention, the "nanoparticles" refer to particles having an average particle size of 1 nm or more and less than 1 µm. In the present invention, the "dispersion" refers to any dispersion medium containing fine particles in a dispersed state. In the present invention, the "fine particle dispersion liquid" refers to a liquid medium (e.g., an aqueous medium including physiologically acceptable aqueous solutions such as water and physiological saline) containing fine particles in a dispersed state. The "microparticle dispersion liquid" and the "nanoparticle dispersion liquid" refer to a liquid medium (e.g., an aqueous medium including physiologically acceptable aqueous solutions such as water and physiological saline) containing microparticles and nanoparticles, respectively, in a dispersed state. The fine particles according to the present invention, for example, the microparticles or the nanoparticles are composed mainly of the non-lamellar liquid crystal-forming lipid and can comprise the drug within the non-lamellar liquid crystal-forming lipid. The fine particles, for example, the microparticles or the nanoparticles can be prepared by dispersing a liquid crystal phase. In one embodiment, the fine particles, for example, the microparticles or the nanoparticles can be prepared as a dispersion liquid (emulsion) obtained by dispersing a suspension liquid containing the non-lamellar liquid crystal-forming lipid, the drug, the aqueous medium, the dispersing agent such as a surfactant, and optionally, an additional component by high-pressure dispersion, ultrasonication, or the like.

The non-lamellar liquid crystal-forming lipid for use in the preparation of the fine particles may be any of the non-lamellar liquid crystal-forming lipids described above. In one embodiment, the non-lamellar liquid crystal-forming lipid may be an amphipathic compound represented by the general formula (I) and may be, for example, mono-O-(5, 9,13-trimethyltetradec-4-enoyl)glycerol. In another embodiment, the non-lamellar liquid crystal-forming lipid may be glycerin fatty acid monoester, for example, glyceryl monooleate.

The fine particles can comprise any of the drugs described above. In one embodiment, the drug may be a lipid soluble (lipophilic) drug.

The "fine particles" according to the present invention may have an average particle size of, but not limited to, preferably 1 nm or more and less than 1 mm, for example, 1 nm to 500 µm, 10 nm to 500 µm, 50 nm to 500 µm, 10 nm to 1 µm, or 50 nm to 50 µm. The nanoparticles according to the present invention may have an average particle size of, but not limited to, preferably 1 nm to 500 nm, for example, 50 nm to 500 nm, 100 nm to 400 nm, or 100 nm to 300 nm.

The fine particle dispersion, for example, the fine particle dispersion liquid such as a nanoparticle dispersion liquid, can comprise any of the additional components described above, in addition to the non-lamellar liquid crystal-forming lipid and the drug. In one embodiment, the fine particle dispersion, for example, the fine particle dispersion liquid such as a nanoparticle dispersion liquid, also preferably comprises any of the surfactants described above, for example, a block copolymer of ethylene oxide and propylene oxide such as polyoxyethylene(196) polyoxypropylene (67) glycol (also called Pluronic® F127). In one embodiment, the fine particle dispersion, for example, the fine particle dispersion liquid such as a nanoparticle dispersion liquid, may comprise a solvent such as ethanol. In one embodiment, the fine particle dispersion, for example, the fine particle dispersion liquid such as a nanoparticle dispersion liquid, may comprise a surfactant and ethanol. In one embodiment, the fine particle dispersion, for example, the fine particle dispersion liquid such as a nanoparticle dispersion liquid, may comprise the oil described above, the water soluble organic compound described above, and/or other pharmaceutically acceptable additive(s).

In one embodiment, the weight ratio between the non-lamellar liquid crystal-forming lipid and the dispersing agent in the fine particle dispersion, for example, the fine particle dispersion liquid such as a nanoparticle dispersion liquid, may be, but not limited to, preferably a ratio of non-lamellar liquid crystal-forming lipid:dispersing agent of 1:1 to 100:1, for example, 3:1 to 50:1, 3:1 to 10:1, 5:1 to 40:1, 10:1 to 30:1, 10:1 to 25:1, or 15:1 to 25:1.

In one embodiment, in the case of using a solvent such as ethanol in the fine particle dispersion, for example, the fine particle dispersion liquid such as a nanoparticle dispersion liquid, the weight ratio of the solvent such as ethanol to the non-lamellar liquid crystal-forming lipid may be, but not limited to, preferably a ratio of non-lamellar liquid crystal-forming lipid:solvent (e.g., ethanol) of 1:10 to 10:1, for example, 1:1 to 10:1, 1.5:1 to 5:1, 2:1 to 10:1, or 5:1 to 10:1.

In one embodiment, the amounts of the non-lamellar liquid crystal-forming lipid, the drug, the dispersing agent (a surfactant, etc.), and the solvent (ethanol, etc.) may be, for example, 1 to 40 w/w %, 0.001 to 10 w/w %, 0.05 to 15 w/w %, and 1 to 30 w/w %, respectively, relative to the total weight of the fine particle dispersion, for example, the fine particle dispersion liquid such as a nanoparticle dispersion liquid. In another embodiment, the amounts of the non-lamellar liquid crystal-forming lipid, the drug, the dispersing agent (a surfactant, etc.), and the solvent (ethanol, etc.) may be, 10 to 30 w/w %, 0.1 to 3 w/w %, 0.3 to 10 w/w %, and 1 to 20 w/w %, respectively, relative to the total weight of the fine particle dispersion, for example, the fine particle dispersion liquid such as a nanoparticle dispersion liquid.

In one embodiment, the amounts of the non-lamellar liquid crystal-forming lipid, the drug, and the dispersing agent (a surfactant, etc.) may be, for example, 1 to 40 w/w %, 0.001 to 10 w/w %, and 0.05 to 15 w/w %, respectively, relative to the total weight of the fine particle dispersion, for example, the fine particle dispersion liquid such as a nanoparticle dispersion liquid. In another embodiment, the amounts of the non-lamellar liquid crystal-forming lipid, the drug, and the dispersing agent (a surfactant, etc.) may be, for example, 10 to 30 w/w %, 0.1 to 3 w/w %, and 0.3 to 10 w/w %, respectively, relative to the total weight of the fine particle dispersion, for example, the fine particle dispersion liquid such as a nanoparticle dispersion liquid.

The external preparation according to the present invention comprising the fine particles or the fine particle dispersion described above may in any of the dosage forms described above. In one embodiment, the external preparation according to the present invention comprising the fine particles or the fine particle dispersion may be for application to a living body surface, preferably the skin or the mucosa, of a subject (e.g., a mammal). In one embodiment, the external preparation according to the present invention comprising the fine particles or the fine particle dispersion may be for application to the mucosa (mucosal surface) and may be, for example, a transnasal formulation. In another embodiment, the external preparation according to the present invention comprising the fine particles or the fine particle dispersion may be a spray formulation such as an aerosol formulation.

8. Delivery into Brain

The external preparation according to the present invention can be advantageously used, particularly, in drug delivery into brain. In one embodiment, the external preparation according to the present invention for use in drug delivery into brain may be an external preparation comprising the fine particles or the fine particle dispersion described above. In one embodiment, the external preparation according to the present invention for application to the mucosa (mucosal surface), for example, the external preparation according to the present invention which is a transnasal formulation, is particularly suitable for drug delivery into brain. Such an external preparation according to the present invention may be the external preparation according to the present invention comprising the fine particles or the fine particle dispersion described above, or may be the patch, the aerosol formulation, or the liquid crystal precursor formulation described above. The external preparation according to the present invention can efficiently deliver the drug into brain by transdermal administration or transmucosal administration, for example, intranasal administration. The external preparation according to the present invention can largely improve drug delivery efficiency into brain (particularly including the olfactory bulb, the cortex, the brain stem, the cerebellum, the midbrain, and/or the hippocampus).

Thus, the present invention also provides a method for delivering a drug into brain, comprising transdermally or transmucosally, for example, intranasally, administering the external preparation according to the present invention to any of the subjects described above, such as a human. The transdermal administration may be performed with, but not limited to, for example, a patch, a spray formulation (an aerosol formulation, etc.), an ointment, or a cream. The transmucosal administration may be performed with, for example, a patch, a spray formulation (an aerosol formulation, etc.), a transnasal formulation, a buccal a suppository, or a vaginal suppository.

The dose of the external preparation according to the present invention for use in drug delivery into brain can be appropriately determined by persons skilled in the art depending on the drug. For example, the single dose of the external preparation according to the present invention may be 1 ng to 10 g, for example, 10 ng to 100 mg, per kg body weight of the subject. For example, the single dose of the external preparation according to the present invention comprising the fine particle dispersion may be preferably equivalent to 1 μL to 500 μL, for example, 10 μL to 100 μL, in the amount of the fine particle dispersion per kg body weight of the subject.

The drug contained in the external preparation for used in drug delivery into brain may be any drug desired to be delivered into the brain. The drug may be an organic compound or an inorganic compound and may be a protein, a peptide, an amino acid, a nucleic acid, or the like. The drug may be selected from the drugs described above. Examples of the drug include, but are not limited to, therapeutic drugs for brain or central nervous system diseases such as Alzheimer's disease, Parkinson's disease, cerebrovascular disorder, and brain tumor, antipsychotic drugs, and anesthetics.

EXAMPLES

Hereinafter, the present invention will be described further specifically with reference to the following Examples. However, the technical scope of the present invention is not limited to these Examples.

[Example 1] Synthesis of
Mono-O-(5,9,13-Trimethyltetradec-4-Enoyl)Glycerol

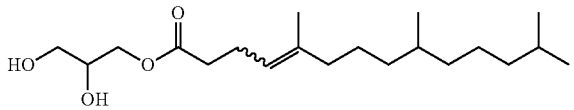 [SMILES: CC(=CCCC(=O)OCC(O)CO)CCCC(C)CCCC(C)C]

1.0 g (3.5 mmol) of methyl 5,9,13-trimethyltetradec-4-enoate (methyl tetrahydrofarnesylacetate) was slowly added dropwise to a solution of 0.65 g (7.1 mmol) of glycerol and 0.59 g (4.3 mmol) of potassium carbonate in dry N,N-dimethylformamide (3.5 mL) at 80° C. After the reaction mixture was stirred at 100° C. for 18 hours, 1 M hydrochloric acid was added to the reaction solution, followed by extraction with ether. The extract was washed with saturated sodium bicarbonate aqueous solution and saturated brine, successively, and dried over anhydrous sodium sulfate. After filtration, the filtrate was concentrated. The resulting residue was purified by silica gel column chromatography (ethyl acetate/hexane mixture) to obtain the title compound as a colorless transparent liquid.

$^1$H-NMR and viscosity of the obtained compound were measured. The results were as follows:

$^1$H-NMR spectrum (300 MHz, CDCl$_3$, TMS) δ: 0.80-0.90 (m, 9H), 1.00-1.70 (m, 15H), 1.97 (td, J=7.8, 17.0 Hz, 2H), 2.13 (t, J=6.1 Hz, 1H, OH), 2.25-2.45 (m, 4H), 2.55 (d, J=5.2 Hz, 1H, OH), 3.50-4.00 (m, 3H), 4.10-4.25 (m, 2H), 5.08 (t, J=6.7 Hz, 1H)

Viscosity: 0.48 Pa·s (at shear velocity of 92 1/s)

Mono-O-(5,9,13-trimethyltetradec-4-enoyl)glycerol synthesized is also referred to as C17MGE, or C17 glycerin ester.

[Example 2] Synthesis of
Mono-O-(5,9,13-Trimethyltetradecanoyl)Glycerol

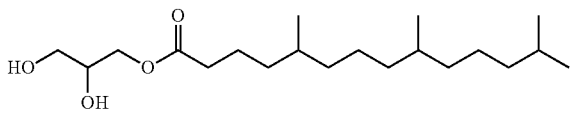 [SMILES: CC(C)CCCC(C)CCCC(C)CCCC(=O)OCC(O)CO]

70 g (0.53 mol) of 2,2-dimethyl-1,3-dioxolane-4-methanol and 36.7 g (266 mmol) of potassium carbonate were added to 50.3 g (177 mmol) of methyl 5,9,13-trimethyltetradecanoate, followed by stirring at 85° C. for 3 hours under reduced pressure of 200 to 250 mmHg. In this reaction, the methanol produced was distilled off. After the resulting reaction solution was subjected to vacuum concentration (from 50 to 210° C., from 1.4 to 0.38 kPa), the resulting residue was purified by silica gel column chromatography (hexane/ethyl acetate) to obtain 43.0 g of (2,2-dimethyl-1,3-dioxolane-4-yl)methyl 5,9,13-trimethyltetradecanoate (63% yield).

3 M hydrochloric acid (85 mL) was added to a solution of 32.7 g (85.0 mmol) of (2,2-dimethyl-1,3-dioxolane-4-yl) methyl 5,9,13-trimethyltetradecanoate in tetrahydrofuran (340 mL) at room temperature, followed by stirring at the same temperature for 5 hours. The reaction solution was added to a mixture of ethyl acetate (300 mL) and saturated sodium bicarbonate aqueous solution (400 mL), followed by separation. The separated organic layer was washed with saturated brine, and dried over magnesium sulfate. After filtration, the filtrate was concentrated, and the resulting residue was purified by silica gel column chromatography (hexane/ethyl acetate) to obtain 28.7 g of the title compound (98% yield) as a colorless transparent liquid. $^1$H-NMR of the obtained compound was measured. The results were as follows:

$^1$H-NMR spectrum (270 MHz, CDCl$_3$, TMS) δ: 0.7-0.9 (m, 12H), 0.95-1.45 (m, 16H), 1.45-1.75 (m, 3H), 2.34 (t, J=7.4 Hz, 2H), 3.60 (dd, J=5.8, 11.5 Hz, 1H), 3.70 (dd, J=4.0, 11.5 Hz, 1H), 3.94 (m, 1H), 4.15 (dd, J=5.9, 11.7 Hz, 1H), 4.21 (dd, J=4.7, 11.7 Hz, 1H)

Mono-O-(5,9,13-trimethyltetradecanoyl)glycerol synthesized is also referred to as saturated C17 glycerin ester.

[Example 3] Synthesis of Mono-O-(5,9,13-Trimethyltetradeca-4,8,12-Trienoyl)Glycerol

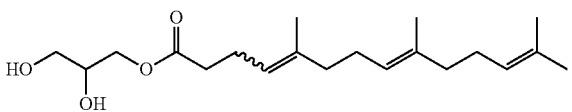 [SMILES: CC(C)=CCC/C(C)=C/CCC(C)=CCCC(=O)OCC(O)CO]

Under reduced pressure of 200 to 250 mmHg, 13.9 g (50.0 mmol) of methyl 5,9,13-trimethyltetradeca-4,8,12-trienoate (methyl farnesylacetate) was slowly added dropwise at 85° C. to a solution of 9.2 g (0.10 mol) of glycerol and 0.28 g (2.0 mmol) of potassium carbonate in dry N,N-dimethylformamide (20 mL), followed by stirring at the same temperature for 3 hours. In this reaction, the methanol produced was distilled off. The resulting reaction solution was diluted with a mixed solvent of ethyl acetate/hexane (1:1, 150 mL), washed with water, saturated sodium bicarbonate aqueous solution, and saturated brine (twice), and dried over magnesium sulfate. After filtration, the filtrate was concentrated, and the resulting residue was purified by silica gel column chromatography (hexane/ethyl acetate=100:0 to 0:100) to obtain 8.22 g of the title compound (49% yield) as a colorless transparent liquid. $^1$H-NMR and viscosity of the obtained compound were measured. The results were as follows:

$^1$H-NMR spectrum (270 MHz, CDCl$_3$, TMS) δ: 1.5-1.8 (m, 12H), 1.9-2.1 (m, 8H), 2.1 (brs, 1H, OH), 2.25-2.45 (m, 4H), 2.56 (brs, 1H, OH), 3.59 (dd, J=5.6, 11.2 Hz, 1H), 3.68 (dd, J=3.6, 11.2 Hz, 1H), 3.92 (m, 1H), 4.14 (dd, J=6.0, 11.6 Hz, 1H), 4.21 (dd, J=4.8, 11.6 Hz, 1H), 5.02-5.16 (m, 3H)

Viscosity: 0.26 Pa·s (at shear velocity of 92 1/s)

Mono-O-(5,9,13-trimethyltetradeca-4,8,12-trienoyl)glycerol synthesized is also referred to as glyceryl farnesylacetate.

[Example 4] Synthesis of Mono-O-(5,9,13,17-Tetramethyloctadec-4-Enoyl)Glycerol

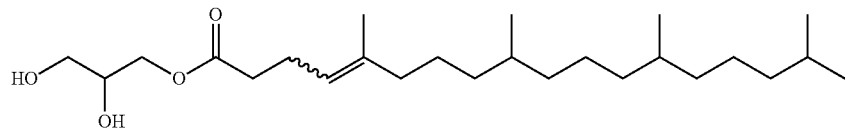 [SMILES: CC(=CCCC(=O)OCC(O)CO)CCCC(C)CCCC(C)CCCC(C)C]

Under reduced pressure of 60 to 70 mmHg and nitrogen gas stream, 28.2 g (80.0 mmol) of methyl 5,9,13,17-tetramethyloctadec-4-enoate was slowly added dropwise at 80° C. to a solution of 23.5 g (255 mmol) of glycerol and 0.55 g (4.0 mmol) of potassium carbonate in dry N,N-dimethylformamide (48 mL), followed by stirring at the same temperature for 3 hours. The resulting reaction solution was diluted with a mixed solvent of ethyl acetate/hexane (1:1, 200 mL), washed with water, saturated sodium bicarbonate aqueous solution, and saturated brine (twice), and dried over magnesium sulfate. After filtration, the filtrate was concentrated, and the resulting residue was purified by silica gel column chromatography (hexane/ethyl acetate=100:0 to 30:70) to obtain 13.3 g of the title compound (400/% yield) as a pale yellow transparent liquid. $^1$H-NMR of the obtained compound was measured. The results were as follows:

$^1$H-NMR spectrum (300 MHz, CDCl$_3$, TMS) δ: 0.80-0.95 (m, 12H), 1.00-1.70 (m, 22H), 1.85-2.15 (m, 2H), 2.15-2.55 (m, 4H), 3.53-3.78 (m, 3H), 3.80-4.00 (m, 1H), 4.10-4.25 (m, 2H), 5.08 (dd, J=6.9 Hz, J=6.9 Hz, 1H)

Mono-O-(5,9,13,17-tetramethyloctadec-4-enoyl)glycerol synthesized is also referred to as C22MGE, or C22 glycerin ester.

[Example 5] Synthesis of Mono-O-(5,9,13,17-Tetramethyloctadecanoyl)Glycerol

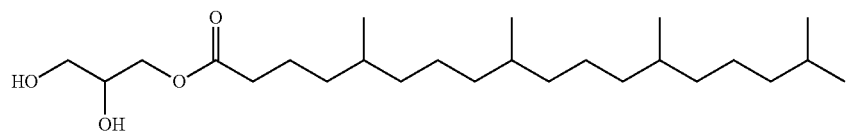 [SMILES: CC(C)CCCC(C)CCCC(C)CCCC(C)CCCC(=O)OCC(O)CO]

Under a nitrogen atmosphere, 2.5 g of 5% palladium carbon was added to a solution of 20.6 g (50.0 mmol) of mono-O-(5,9,13,17-tetramethyloctadec-4-enoyl)glycerol in ethyl acetate (62 mL). After nitrogen in the system was replaced with hydrogen, the reaction mixture was stirred at room temperature for 42 hours under an atmospheric pressure hydrogen atmosphere. After hydrogen in the system was replaced with nitrogen, the 5% palladium carbon was filtered off. The filtrate was purified by silica gel column chromatography (ethyl acetate) to obtain 20.2 g of the title compound (98% yield) as a colorless transparent liquid. $^1$H-NMR of the obtained compound was measured. The results were as follows:

$^1$H-NMR spectrum (300 MHz, CDCl$_3$, TMS) δ: 0.7-0.9 (m, 15H), 0.95-1.75 (m, 26H), 2.13 (t, J=6.0 Hz, OH), 2.34 (t, J=7.7 Hz, 2H), 2.56 (d, J=5.1 Hz, OH), 3.55-3.75 (m, 2H), 3.94 (m, 1H), 4.15 (dd, J=6.0, 11.7 Hz, 1H), 4.20 (dd, J=4.7, 11.7 Hz, 1H)

Mono-O-(5,9,13,17-tetramethyloctadecanoyl)glycerol synthesized is also referred to as saturated C22 glycerin ester.

[Example 6] Synthesis of Mono-O-(5,9,13,17-Tetramethyloctadeca-4,8,12,16-Tetraenoyl)Glycerol (1) Synthesis of Methyl 5,9,13,17-Tetramethyloctadeca-4,8,12,16-Tetraenoate (i.e., Methyl Geranylgeranylacetate)

Under a nitrogen atmosphere, a solution of 53 mL (0.42 mol) of trimethyl orthoacetate and 5.0 mL (40 mmol) of n-hexanoic acid was added dropwise at 135° C. over 8 hours to a solution of 58.1 g (200 mmol) of 3,7,11,15-tetramethylhexadeca-1,6,10,14-tetraen-3-ol (i.e., geranyl linalool) and 19 mL (0.15 mol) of trimethyl orthoacetate. After the reaction mixture was stirred for 6 hours at the same temperature, a solution of 5.3 mL (42 mmol) of trimethyl orthoacetate and 0.5 mL (4 mmol) of n-hexanoic acid was further added dropwise, and the mixture was further stirred for 2 hours at the same temperature. The resulting reaction solution was diluted with a mixed solvent of ethyl acetate/hexane (3:1, 300 mL), washed with saturated sodium bicarbonate aqueous solution (twice), and saturated brine, and dried over magnesium sulfate. After filtration, the filtrate was concentrated to obtain 67.24 g of methyl 5,9,13,17-tetramethyloctadeca-4,8,12,16-tetraenoate (i.e., methyl geranylgeranylacetate) as a crude liquid product. The crude product was directly used for the next reaction.

(2) Synthesis of Mono-O-(5,9,13,17-Tetramethyloctadeca-4,8,12,16-Tetraenoyl)Glycerol

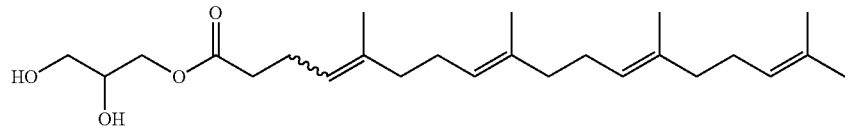 [SMILES: CC(C)=CCC/C(C)=C/CC/C(C)=C/CCC(C)=CCCC(=O)OCC(O)CO]

Under reduced pressure of 200 to 250 mmHg, 13.9 g (40.0 mmol) of methyl 5,9,13,17-tetramethyloctadeca-4,8,12,16-tetraenoate (i.e., methyl geranylgeranylacetate) was slowly added dropwise at 85° C. to a solution of 7.4 g (80 mmol) of glycerol and 5.5 g (40 mmol) of potassium carbonate in dry N,N-dimethylformamide (16 mL), followed by stirring at the same temperature for 6 hours. In this reaction, the methanol produced was distilled off. The resulting reaction solution was diluted with a mixed solvent of ethyl acetate/hexane (1:1, 200 mL), washed with water, saturated sodium bicarbonate aqueous solution, and saturated brine (twice), and dried over magnesium sulfate. After filtration, the filtrate was concentrated, and the resulting residue was purified by silica gel column chromatography (hexane/ethyl acetate=100:0 to 0:100) to obtain 5.44 g of the title compound (33% yield) as a transparent liquid. $^1$H-NMR and viscosity of the obtained compound were measured. The results were as follows:

¹H-NMR spectrum (270 MHz, CDCl₃, TMS) δ: 1.55-1.72 (m, 15H), 1.9-2.2 (m, 13H), 2.27-2.45 (m, 4H), 2.53 (brs, 1H, OH), 3.59 (dd, J=5.4, 11.4 Hz, 1H), 3.68 (dd, J=3, 11.4 Hz, 1H), 3.92 (m, 1H), 4.15 (dd, J=6.0, 11.6 Hz, 1H), 4.21 (dd, J=4.8, 11.6 Hz, 1H), 5.05-5.15 (m, 4H)

Viscosity: 0.37 Pa·s (at shear velocity of 92 1/s)

Mono-O-(5,9,13,17-tetramethyloctadeca-4,8,12,16-tetraenoyl)glycerol synthesized is also referred to as glyceryl geranylgeranylacetate.

[Example 7] Preparation of Liquid Crystal Precursor Formulation 1. Reagent

Rhodamine B (RB) and triamcinolone acetonide (TA) were purchased from Wako Pure Chemical Industries, Ltd. (Osaka, Japan), and hydroxypropylcellulose (HPC) was purchased from Nippon Soda Co., Ltd. (Tokyo, Japan). Table 1 shows the structural formula and physicochemical parameters of TA. The hydrophobicity index C log P was calculated using Chem Draw Ultra 10.0® (PerkinElmer Informatics, Cambridge, MA, U.S.A.).

TABLE 1

| Structural formula | Molecular weight (M.W.) | ClogP | pK$_a$ |
|---|---|---|---|
| (triamcinolone acetonide structure) | 434.5 | 0.73 | 13.37 |

HPC is known to have a viscosity increased depending on an average number of substituted hydroxyl groups (hydroxypropoxy groups) per cellulose unit (degree of substitution). HPC having a degree of substitution of 0.2 to 0.4% is called low substituted HPC, and HPC having a degree of substitution of 53.4 to 77.5% is called highly substituted HPC. HPC of five grades, low-substituted SSL, SL, and L and highly substituted M and H, were used. The viscosities (at 20° C., 2% aqueous solution) of these 5 types of HPC are 2 to 2.9 mpa·s for SSL, 3 to 5.9 mpa·s for SL, 6 to 10 mpa·s for L, 150 to 400 mpa·s for M, and 1000 to 4000 mpa·s for H.

2. Preparation of Liquid Crystal Precursor Formulation—(1)

Formulations containing RB or TA as a drug were prepared as follows.

First, HPC was added by small portions to a vial containing ethanol. Then, the vial was placed in a hot bath set to 60° C., and stirred overnight so that the HPC in the vial was completely dissolved to obtain an HPC-containing ethanol solution.

C17MGE and the HPC-containing ethanol solution thus obtained were mixed at a weight ratio of 7:3 and thoroughly stirred for 1 hour. Also, C17MGE and ethanol were added to a vial and mixed, and thoroughly stirred to prepare an HPC-free solution.

To the solutions thus prepared, RB was added to a final concentration of 0.001% to prepare RB-containing formulation Nos. 1 to 6, and TA was added to a final concentration of 0.1% to prepare TA-containing formulation Nos. 7 to 12. These formulations were also able to be prepared by adding the drug to the HPC-containing ethanol solution or ethanol in advance and then mixing C17MGE therewith.

Further, the drug and HPC were added to C17MGE and the mixture was stirred, in the absence of ethanol, to prepare formulation Nos. 13 to 18 containing no ethanol, but containing C17MGE.

Formulation Nos. 1 to 18 thus prepared were liquid crystal precursor formulations containing no water.

For comparative controls, water, instead of C17MGE, was mixed and stirred with ethanol, the drug, and HPC to prepare formulation Nos. 19 to 23 containing no C17MGE. Also, aqueous TA solution No. 24 was prepared.

Table 2 shows the compositional ratios (weight ratios) of formulation Nos. 1 to 24 prepared.

TABLE 2

| Formulation No. | 1 | 2 | 3 | 4 | 5 | 6 |
|---|---|---|---|---|---|---|
| Code Name | ME | ME-SSL | ME-SL | ME-L | ME-M | ME-H |
| C17MGE | 70 | 70 | 70 | 70 | 70 | 70 |
| HPC - SSL | | 1 | | | | |
| SL | | | 1 | | | |
| L | | | | 1 | | |
| M | | | | | 1 | |
| H | | | | | | 1 |
| Ethanol | 29.999 | 28.999 | 28.999 | 28.999 | 28.999 | 28.999 |
| Water | | | | | | |
| Rhodamine B (RB) | 0.001 | 0.001 | 0.001 | 0.001 | 0.001 | 0.001 |
| Triamcinolone acetonide (TA) | | | | | | |
| Total | 100.00 | 100.00 | 100.00 | 100.00 | 100.00 | 100.00 |

| Formulation No. | 7 | 8 | 9 | 10 | 11 | 12 |
|---|---|---|---|---|---|---|
| Code Name | ME | ME-SSL | ME-SL | ME-L | ME-M | ME-H |
| C17MGE | 70 | 70 | 70 | 70 | 70 | 70 |
| HPC - SSL | | 1 | | | | |
| SL | | | 1 | | | |
| L | | | | 1 | | |
| M | | | | | 1 | |

TABLE 2-continued

| | | | | | | |
|---|---|---|---|---|---|---|
| H | | | | | | 1 |
| Ethanol | 29.9 | 28.9 | 28.9 | 28.9 | 28.9 | 28.9 |
| Water | | | | | | |
| Rhodamine B (RB) | | | | | | |
| Triamcinolone acetonide (TA) | 0.1 | 0.1 | 0.1 | 0.1 | 0.1 | 0.1 |
| Total | 100.00 | 100.00 | 100.00 | 100.00 | 100.00 | 100.00 |

| Formulation No. | 13 | 14 | 15 | 16 | 17 | 18 |
|---|---|---|---|---|---|---|
| Code Name | M-SSL | M-SL | M-L | M-M | M-H | M-SSL |
| C17MGE | 99 | 99 | 99 | 99 | 99 | 98.9 |
| HPC - SSL | 1 | | | | | 1 |
| SL | | 1 | | | | |
| L | | | 1 | | | |
| M | | | | 1 | | |
| H | | | | | 1 | |
| Ethanol | | | | | | |
| Water | | | | | | |
| Rhodamine B (RB) | 0.001 | 0.001 | 0.001 | 0.001 | 0.001 | |
| Triamcinolone acetonide (TA) | | | | | | 0.1 |
| Total | 100.00 | 100.00 | 100.00 | 100.00 | 100.00 | 100.00 |

| Formulation No. | 19 | 20 | 21 | 22 | 23 | 24 |
|---|---|---|---|---|---|---|
| Code Name | E-SSL | E-SL | E-L | E-M | E-H | TA aq |
| C17MGE | | | | | | |
| HPC - SSL | 1 | | | | | |
| SL | | 1 | | | | |
| L | | | 1 | | | |
| M | | | | 1 | | |
| H | | | | | 1 | |
| Ethanol | 28.999 | 28.999 | 28.999 | 28.999 | 28.999 | |
| Water | 70 | 70 | 70 | 70 | 70 | 99.9 |
| Rhodamine B (RB) | 0.001 | 0.001 | 0.001 | 0.001 | 0.001 | |
| Triamcinolone acetonide (TA) | | | | | | 0.1 |
| Total | 100.00 | 100.00 | 100.00 | 100.00 | 100.00 | 100.00 |

3. Preparation of Liquid Crystal Precursor Formulation—(2)

Formulation Nos. 25 to 36 containing RB or TA were prepared by the same procedures as in the preceding section 2. according to the compositional ratios (weight ratios) of Table 3 using glyceryl monooleate (GMO) instead of C17MGE of the preceding section 2. Also, the drug and HPC were added to GMO and the mixture was heated and stirred, in the absence of ethanol, to prepare formulation Nos. 37 and 38 containing no ethanol, but containing GMO.

TABLE 3

| Formulation No. | 25 | 26 | 27 | 28 | 29 | 30 | 31 |
|---|---|---|---|---|---|---|---|
| Code Name | GE | GE-SSL | GE-SL | GE-L | GE-M | GE-H | GE |
| GMO | 70 | 70 | 70 | 70 | 70 | 70 | 70 |
| HPC - SSL | | 1 | | | | | |
| SL | | | 1 | | | | |
| L | | | | 1 | | | |
| M | | | | | 1 | | |
| H | | | | | | 1 | |
| Ethanol | 29.999 | 28.999 | 28.999 | 28.999 | 28.999 | 28.999 | 29.9 |
| Water | | | | | | | |
| Rhodamine B (RB) | 0.001 | 0.001 | 0.001 | 0.001 | 0.001 | 0.001 | |
| Triamcinolone acetonide (TA) | | | | | | | 0.1 |
| Total | 100.00 | 100.00 | 100.00 | 100.00 | 100.00 | 100.00 | 100.00 |

| Formulation No. | 32 | 33 | 34 | 35 | 36 | 37 | 38 |
|---|---|---|---|---|---|---|---|
| Code Name | GE-SSL | GE-SL | GE-L | GE-M | GE-H | G-SSL | G-SSL |
| GMO | 70 | 70 | 70 | 70 | 70 | 99 | 98.9 |
| HPC - SSL | 1 | | | | | 1 | 1 |
| SL | | 1 | | | | | |
| L | | | 1 | | | | |
| M | | | | 1 | | | |
| H | | | | | 1 | | |

TABLE 3-continued

| | | | | | | | |
|---|---|---|---|---|---|---|---|
| Ethanol | 28.9 | 28.9 | 28.9 | 28.9 | 28.9 | | |
| Water | | | | | | | |
| Rhodamine B (RB) | | | | | | 0.001 | |
| Triamcinolone acetonide (TA) | 0.1 | 0.1 | 0.1 | 0.1 | 0.1 | | 0.1 |
| Total | 100.00 | 100.00 | 100.00 | 100.00 | 100.00 | 100.00 | 100.00 |

4. Preparation of Liquid Crystal Precursor Formulation—(3)

RB- or TA-containing formulation Nos. 39 to 49 and 79 to 81 were prepared by the same procedures as in the preceding section 2. according to the compositional ratios (weight ratios) of Table 4 using oil (squalene) plus C117MGE; C22MGE; or oil (IPM or tocopherol) plus C22MGE.

TABLE 4

| Formulation No. | 39 | 40 | 41 | 42 | 43 | 44 |
|---|---|---|---|---|---|---|
| Code Name | MSE | MSE-SSL | MSE-SL | MSE-L | MSE-M | MSE-H |
| C17MGE | 70 | 69 | 69 | 69 | 69 | 69 |
| C22MGE | | | | | | |
| Squalene | 7 | 7 | 7 | 7 | 7 | 7 |
| Isopropyl myristate (IPM) | | | | | | |
| Tocopherol | | | | | | |
| HPC - SSL | | 1 | | | | |
| SL | | | 1 | | | |
| L | | | | 1 | | |
| M | | | | | 1 | |
| H | | | | | | 1 |
| Ethanol | 22.999 | 22.999 | 22.999 | 22.999 | 22.999 | 22.999 |
| Propylene glycol | | | | | | |
| Rhodamine B (RB) | 0.001 | 0.001 | 0.001 | 0.001 | 0.001 | 0.001 |
| Triamcinolone acetonide (TA) | | | | | | |
| Total | 100.00 | 100.00 | 100.00 | 100.00 | 100.00 | 100.00 |

| Formulation No. | 45 | 46 | 47 | 48 | 49 | 79 | 80 | 81 |
|---|---|---|---|---|---|---|---|---|
| Code Name | | | | | | | | |
| C17MGE | | | | | | | | |
| C22MGE | 85 | 85 | 76.5 | 63.75 | 55.25 | 85 | 85 | 63.75 |
| Squalene | | | | | | | | |
| Isopropyl myristate (IPM) | | | 8.5 | 21.25 | | | | 21.25 |
| Tocopherol | | | | | 29.75 | | | |
| HPC - SSL | | 1 | 1 | 1 | 1 | | 1 | 1 |
| SL | | | | | | | | |
| L | | | | | | | | |
| M | | | | | | | | |
| H | | | | | | | | |
| Ethanol | 10 | 10 | 10 | 10 | 10 | 10 | 10 | 10 |
| Propylene glycol | 4.999 | 3.999 | 3.999 | 3.999 | 3.999 | 4.9 | 3.9 | 3.9 |
| Rhodamine B (RB) | 0.001 | 0.001 | 9.001 | 0.001 | 0.091 | | | |
| Triamcinolone acetonide (TA) | | | | | | 0.1 | 0.1 | 0.1 |
| Total | 100.00 | 100.00 | 100.00 | 100.00 | 100.0 | 100.00 | 100.00 | 100.00 |

[Example 8] Characteristics Test of Formulation

1. Spraying Test

Formulation Nos. 1 to 5, 13, 19 to 23, and 46 prepared in Example 7 were each placed in a 5 mL spray vial (No. 2, Maruemu Corp., Japan) and sprayed vertically downward once from a distance of 3 cm to Kimwipe moistened with water. The spray vial used can spray 60 μL of purified water by one manual push. The diameter of an area in which the formulation was sprayed on the Kimwipe (spraying area) was measured. Spraying, if attained, having a spraying area with a diameter of 1 cm or more was determined as mist spraying, and spraying having a spraying area with a diameter of less than 1 cm was determined as stream spraying. The case where the formulation was not sprayed from the nozzle of the spray vial was determined as failed spraying.

As a result, all the formulations were able to be sprayed using the spray vial described above. Formulation Nos. 1, 19, and 20 were mist-sprayed, and formulation Nos. 2 to 5, 13, 21 to 23, and 46 were stream-sprayed.

2. Liquid Crystal Structure Formation Test

Using the same 5 mL spray vial as that of the spraying test, formulation Nos. 1 to 5, 19, 25, and 26 prepared in Example 2 were each sprayed vertically downward once to 150 μL of purified water added dropwise into Glass Bottom Dish (Matsunami Glass Ind., Ltd., Japan), from a distance of 15 cm from the bottom of the dish. In order to determine the presence or absence of liquid crystal formation, the formulation in contact with water in the dish was observed using digital microscope VHX-5000 (Keyence Corp., Japan) on a polarizing microscope mode.

FIGS. 1A-1H show results of observation under a polarizing microscope. A polarization image showing a liquid crystal structure was observed in all of formulation Nos. 1 to 5, 25, and 26 containing C17MGE or GMO (FIGS. 1A to 1E, 1G, and 1H). On the other hand, a polarization image showing a liquid crystal structure was not observed in formulation No. 19 containing HPC, but containing no C17MGE (FIG. 1F). These results show that the formulations containing C17MGE formed a liquid crystal structure in water to which it was sprayed. A clearer polarization image was observed in the formulations containing HPC with a lower degree of substitution.

The time required for liquid crystal formation (emergence of a polarization image) after spraying was compared between C17MGE and GMO. As a result, the time was within 5 seconds for C17MGE formulation No. 1 and within 10 seconds for GMO formulation No. 25 under conditions containing no HPC, and was within 20 seconds for C17MGE formulation No. 2 and within 90 seconds for GMO formulation No. 26 under conditions containing HPC of the grade SSL. Thus, the formulations containing C17MGE (Nos. 1 and 2) had a significantly higher rate of formation of liquid crystals. Although a formulation containing C17MGE or GMO is fixed to a mucosal surface quickly after spraying, the formulation containing C17MGE, as compared with the formulation containing GMO, tends to be fixed to a mucosal surface more quickly after spraying. It is considered that the formulation containing C17MGE is more likely to produce an active ingredient release or absorption promoting effect.

3. Small-Angle X-Ray Scattering Diffraction

In the liquid crystal structure formation test conducted using formulation Nos. 1 to 3, 13, and 45 to 49 containing C17MGE or C22MGE, and formulation Nos. 25 to 27 and 37 containing GMO, the formulations sprayed to water became gel materials. These gel materials were subjected to small-angle X-ray scattering diffractometry using a small-angle X-ray scattering (SAXS) apparatus (manufactured by Rigaku Corp., Nano-Viewer) to determine a non-lamellar liquid crystal structure.

At least 3 scattering peaks were observed in the small-angle X-ray scattering diffraction of the gel material containing each of formulation Nos. 1, 13, 37, and 45 to 47 (FIGS. 2A, 2D, and FIGS. 3A to 3D). The peak value ratio indicated the ratio of 1:$\sqrt{3}$:2 peculiar to reverse hexagonal liquid crystals. Accordingly, these formulations were found to form reverse hexagonal liquid crystals.

At least 6 scattering peaks were observed in the small-angle X-ray scattering diffraction of the gel material containing each of formulation Nos. 2, 3, and 25 to 27 (FIGS. 2B, 2C, and 2E to 2G). The peak value ratio indicated the ratio of $\sqrt{2}$:$\sqrt{3}$:$\sqrt{4}$:$\sqrt{8}$ peculiar to cubic liquid crystals belonging to the crystallographic space group Pn3m, and the ratio of 1:$\sqrt{3}$:2 peculiar to reverse hexagonal liquid crystals. Accordingly, these formulations, when used, were found to form mixtures of cubic liquid crystals belonging to the crystallographic space group Pn3m, and reverse hexagonal liquid crystals.

At least 8 scattering peaks were observed in the small-angle X-ray scattering diffraction of the gel material containing formulation No. 48 or 49 (FIGS. 3E and 3F). The peak value ratio indicated the ratio of $\sqrt{3}$:$\sqrt{8}$:$\sqrt{11}$:$\sqrt{12}$:$\sqrt{16}$:$\sqrt{19}$:$\sqrt{24}$:$\sqrt{27}$ peculiar to reverse cubic liquid crystals belonging to the crystallographic space group Fd3m. Accordingly, these formulations were found to form reverse cubic liquid crystals belonging to the crystallographic space group Fd3m.

[Example 9] Formulation Retention Test on Mucosa

A three-drug mixed anesthetic (0.15 mg/kg medetomidine hydrochloride, 2 mg/kg midazolam, and 2.5 mg/kg butorphanol tartrate) was intraperitoneally administered to each of male WBN/ILA-Ht hairless rats (body weight: 200 to 250 g, 8 weeks old), and the back skin was excised. The horny cell layer (stratum corneum) was removed from this excised rat back skin (3 cm×3 cm) by tape stripping treatment, and the obtained horny cell layer-stripped skin (epidermis-exposed skin) was used as a mucosa model.

Using a spray vial, formulation Nos. 1 to 6, 13 to 17, 19 to 23, 25 to 28, 30, 39 to 41, 45, and 46 prepared in Example 7 were each sprayed vertically downward once from a distance of 3 cm to the mucosa model fixed to a plate covered with aluminum foil. Immediately after spraying, the adhered area of the formulation on the mucosa model (herein, post-spraying immediate area) was measured. 15 seconds after spraying, water of 37° C. was continuously flowed at a flow rate of 200 mL/min for 1 hour onto the mucosa model inclined with an angle of 45° from the horizon. Then, the adhered area of the formulation on the mucosa model herein, post-water-flow-test area) was measured. The measurement of the post-spraying immediate area and the post-water-flow-test area employed digital microscope VHX-5000 (Keyence Corp., Japan) having a stereomicroscope mode equipped with manual XY measurement system VH-M100.

The rate of decrease in adhered area of formulation after the water flow test was calculated according to the following expression.

Rate of decrease (%)=(Post-water-flow-test area−Post-spraying immediate area)/Post-spraying immediate area×100

When this rate of decrease (%) is <−50%, it was determined that a formulation sample was detached from the mucosa model.

The water flow test was conducted three or more times for each formulation, and the formulation retaining property of each formulation was determined by classification into 4 groups according to the following criteria:

s: No sample was detached.

a: The number of detached samples was 40% or less of the number of all samples.

b: The number of detached samples was more than 40% and less than 70% of the number of all samples.

c: The number of detached samples was 70% or more of the number of all samples.

For comparison, the same water flow test was conducted except that one tablet of commercially available oral mucoadhesive formulation Aftach® (Teijin Pharma Ltd., Japan) or 60 mg of oral mucosal ointment formulation Kenalog® (Bristol-Myers Squibb Company, USA) was attached or applied, instead of the formulations prepared in Example 7, to the mucosa model. The results are shown in Table 5.

TABLE 5

| Formulation No./Code Name | Evaluation |
|---|---|
| No. 1/ME | b |
| No. 2/ME-SSL | s |
| No. 3/ME-SL | a |
| No. 4/ME-L | s |
| No. 5/ME-M | s |
| No. 6/ME-H | a |
| No. 13/M-SSL | s |
| No. 14/M-SL | a |
| No. 15/M-L | s |
| No. 16/M-M | s |
| No. 17/M-H | s |
| No. 19/E-SSL | c |
| No. 20/E-SL | c |
| No. 21/E-L | c |
| No. 22/E-M | c |
| No. 23/E-H | c |
| No. 25/GE | b |
| No. 26/GE-SSL | a |
| No. 27/GE-SL | c |
| No. 28/GE-L | b |
| No. 30/GE-H | b |
| No. 39/MSE | a |
| No. 40/MSE-SSL | a |
| No. 41/MSE-SL | a |
| No. 45 | a |
| No. 46 | s |
| Aftach ® | a |
| Kenalog ® | b |

As shown in Table 5, the formulations containing C17MGE or C22MGE were well retained even after the 1-hour water flow test and thus exhibited a high mucoadhesive property. Particularly, the formulations containing HPC, and C17MGE or C22MGE exhibited an exceedingly high mucoadhesive property (retaining property), and had a higher mucoadhesive property than that of the commercially available formulations. All samples of an ethanol solution containing HPC without the use of a liquid crystal-forming lipid were detached in the water flow test.

[Example 10] Formulation Retention Test on Skin

A water flow test was conducted in the same way as in Example 9 except that the excised rat back skin before tape stripping treatment was used as a skin model instead of the mucosa model (horny cell layer-stripped skin) using formulation Nos. 2 and 46.

As a result, both formulation Nos. 2 and 46 were temporarily detached from the skin after the start of the water flow test, whereas the detached gels were reattached to the skin and fixed. It is considered that the contact of the whole formulation with water promoted its reattachment to the skin surface. This result indicates that the formulation of the present invention is easy to detach from the skin with a small water content (oily surface) before forming liquid crystals to exert a bioadhesive property and however, can exert a high bioadhesive property on the skin with a sufficient water content.

Figure 4:
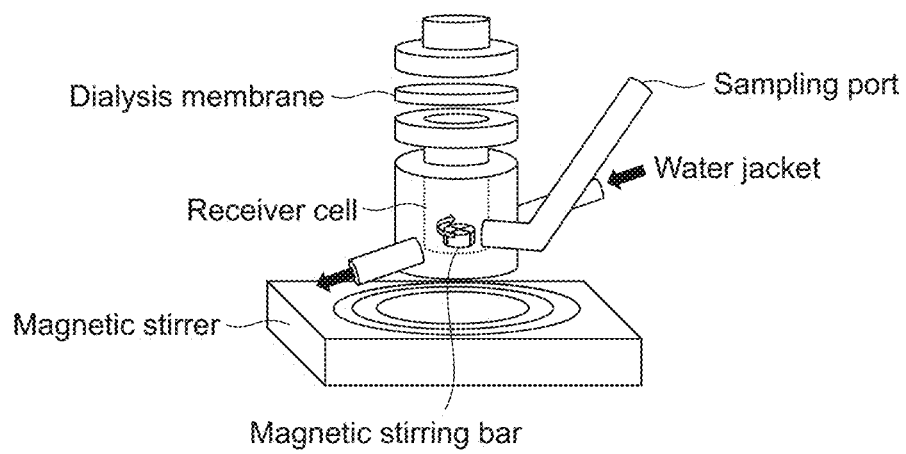
FIG. 4 is a schematic diagram of the structure of a vertical diffusion cell.

[Example 11] In Vitro Releasing Property Test 6.0 mL of a 20% aqueous ethanol solution was added to the receiver cell of the vertical diffusion cell (cell capacity: 6.0 mL, effective diffusion area: 1.77 cm$^2$; Kobayashi Glass Co., Ltd.) shown in FIG. 4, and a dialysis membrane (Cellulose Tube 24/32, Wako Pure Chemical Industries, Ltd., Japan) was set up therein. After 200 µL of artificial saliva Salivate® (Teijin Pharma Ltd., Japan) was added onto the dialysis membrane (at the donor cell side), each formulation was applied thereon to start a test on the in vitro releasing property of the formulation.

The formulations used were formulation Nos. 7 to 12, 18, 24, 31 to 36, 38, 79, 80, and 81 (200 mg each) prepared in Example 7, Kenalog® ointment formulation (200 mg), and one tablet of Aftach® formulation, which contained 0.2 mg of TA as an active ingredient. The Kenalog® ointment formulation was applied after the artificial saliva on the dialysis membrane was wiped off, in accordance with the instructions for use.

In order to measure the amount of TA released from the formulation, the aqueous solution in the receiver cell was sampled by 500 µL each over time and replenished with the same amount of a 20% aqueous ethanol solution during each sampling. The inside of the cell was kept at 37° C., and the inside of the receiver cell was constantly stirred with a magnetic stirrer. During the test, the vertical diffusion cell was placed in an environment kept under high humidity with a humidity of 90% or more using a humidifier.

Acetonitrile was added at a ratio of 1:1 (v/v) to each sample solution collected over time, and the mixture was stirred and then centrifuged (21,500×g, 5 min, 4° C.) to recover a supernatant. The supernatant was assayed by high-performance liquid chromatography (HPLC) to determine a TA concentration. The HPLC system and conditions used in this measurement are shown in Tables 6 and 7.

TABLE 6

| HPLC System (Shimadzu Corp., Kyoto, Japan) | |
|---|---|
| System Controller | SCL-10A |
| Pump | LC-10AD |
| Autosampler | SIL-10A |
| Column oven | CTO-10AC |
| UV detector | SPD-10AV |
| Analytical software | LC solution |
| Degassing apparatus | DGU-12A3 |

TABLE 7

| HPLC Measurement Conditions | |
|---|---|
| Column | Inertsil ® ODS-3 (5 µm, 4.6 × 150 mm) |
| Mobile phase | Acetonitrile:water = 35:65 |
| Flow rate | 1.0 mL/min |
| Wavelength | 240 nm |
| Injection volume | 20 µL |
| Column temperature | 40° C. |

Table 8 shows a cumulative amount of TA released per unit effective release area at 4 hours after formulation application (µg/cm$^2$, an average value from the test conducted three or more times) based on the effective diffusion area (1.77 cm$^2$) of the cell, calculated from the measured TA concentration, and a relative amount of TA released as compared with the Kenalog® ointment formulation.

TABLE 8

| Formulation No./Code Name | Cumulative amount of TA released/effective release area (µg/cm$^2$) | Relative amount released (fold) |
|---|---|---|
| No. 7/ME | 6.22 | 0.5 |
| No. 8/ME-SSL | 11.8 | 0.9 |
| No. 9/ME-SL | 9.76 | 0.7 |

TABLE 8-continued

| Formulation No./ Code Name | Cumulative amount of TA released/effective release area ($\mu g/cm^2$) | Relative amount released (fold) |
|---|---|---|
| No. 10/ME-L | 11.6 | 0.9 |
| No. 11/ME-M | 13.2 | 1.0 |
| No. 12/ME-H | 18.0 | 1.3 |
| No. 18/M-SSL | 15.8 | 1.2 |
| No. 31/GE | 17.3 | 1.3 |
| No. 32/GE-SSL | 17.8 | 1.3 |
| No. 33/GE-SL | 15.0 | 1.1 |
| No. 34/GE-L | 10.7 | 0.8 |
| No. 35/GE-M | 9.51 | 0.7 |
| No. 36/GE-H | 18.8 | 1.4 |
| No. 38/G-SSL | 14.4 | 1.1 |
| No. 79 | 9.62 | 0.7 |
| No. 80 | 10.4 | 0.8 |
| No. 81 | 10.9 | 0.8 |
| No. 24/TA aq | 8.86 | 0.7 |
| Aftach® | 10.3 | 0.8 |
| Kenalog® | 13.6 | 1 |

The formulations containing C17MGE, GMO, or C22MGE exhibited almost the same level of a TA releasing property as that of the commercially available Kenalog® ointment formulation. Among the formulations containing C17MGE, the formulations containing HPC (Nos. 8 to 12 and 18) tended to have a higher TA releasing property than that of the formulation containing no HPC (No. 7).

[Example 12] In Vitro Test on Permeability Through Mucosa 6.0 mL of phosphate buffered saline (PBS) of pH 6.75 was added to the receiver cell of the same vertical diffusion cell as in Example 11 (cell capacity: 6.0 mL, effective diffusion area: 1.77 $cm^2$) (FIG. 4), and hamster oral mucosa (Syrian, male, 8 weeks old, Sankyo Labo Service Corp.) was set up therein instead of the dialysis membrane used in Example 11. After 200 μL of artificial saliva Salivate® (Teijin Pharma Ltd., Japan) was added onto the oral mucosa (at the donor cell side), each formulation was applied thereto to start measurement.

The formulations used were formulation Nos. 7, 8, 24, 31 to 33, 38, and 80 (200 mg each) prepared in Example 7, Kenalog® ointment formulation (200 mg), and one tablet of Aftach® formulation, which contained 0.2 mg of TA as an active ingredient. The Kenalog® ointment formulation was applied after the artificial saliva on the oral mucosa was wiped off, in accordance with the instructions for use.

In order to measure the amount of TA permeated through the mucosa from the formulation, the aqueous solution in the receiver cell was sampled by 500 μL each over time and replenished with the same amount of PBS during each sampling The inside of the cell was kept at 37° C., and the inside of the receiver cell was constantly stirred with a magnetic stirrer. The test was conducted while the vertical diffusion cell was placed in an environment kept under high humidity with a humidity of 90% or more using a humidifier.

Acetonitrile was added at a ratio of 1:1 (v/v) to each sample solution collected over time, and the mixture was stirred and then centrifuged (21,500×g, 5 min, 4° C.) to recover a supernatant. The supernatant was assayed by high-performance liquid chromatography (HPLC) to determine a TA concentration. The HPLC system and conditions used in this measurement are shown in Tables 6 and 7.

Figure 5:
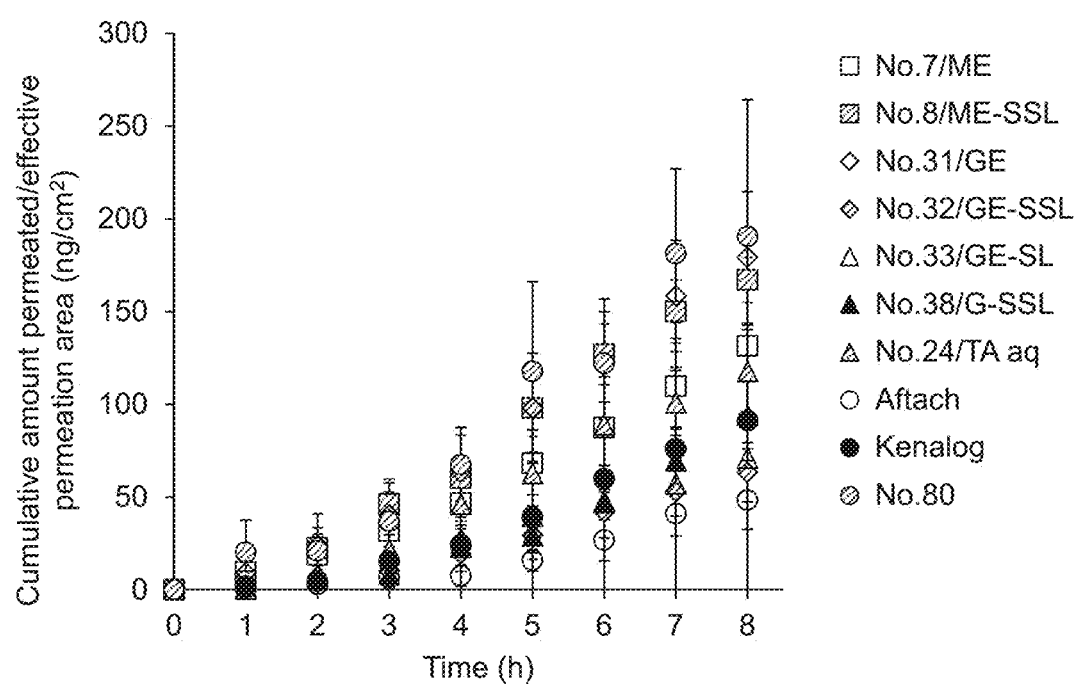
FIG. 5 is a diagram showing FL-Na permeation behavior through the skin from a liquid crystal precursor formulation.

FIG. 5 shows TA permeation behavior through the mucosa from each evaluation formulation. The ordinate of the graph shows an average cumulative amount of TA permeated through the mucosa (an average value from the test conducted three or more times) per unit effective permeation area (sg/$cm^2$) based on the effective diffusion area (1.77 $cm^2$) of the cell, calculated from the measured TA concentration.

Table 9 shows the cumulative amount of TA permeated through the mucosa per unit effective permeation area at 4 hours and 8 hours after formulation application, and a relative amount of TA permeated as compared with the Kenalog® ointment formulation.

TABLE 9

| | 4 hours later | | 8 hours later | |
|---|---|---|---|---|
| Formulation No./Code Name | Cumulative amount of TA permeated/ effective permeation area ($\mu g/cm^2$) | Relative amount permeated (fold) | Cumulative amount of TA permeated/ effective permeation area ($\mu g/cm^2$) | Relative amount permeated (fold) |
| No. 7/ME | 46.9 | 1.9 | 131 | 1.4 |
| No. 8/ME-SSL | 68.2 | 2.5 | 167 | 1.8 |
| No. 31/GE | 63.4 | 2.6 | 179 | 2.0 |
| No. 32/GE-SSL | 19.5 | 0.8 | 63.4 | 0.7 |
| No. 33/GE-SL | 27.4 | 1.1 | 71.0 | 0.8 |
| No. 38/G-SSL | 23.0 | 1.0 | 94.1 | 1.0 |
| No. 24/TA aq | 46.2 | 1.9 | 118 | 1.3 |
| No. 80 | 67.4 | 2.8 | 191 | 2.1 |
| Aftach® | 7.46 | 0.3 | 48.3 | 0.5 |
| Kenalog® | 24.1 | 1 | 91.2 | 1 |

All of formulation Nos. 7, 8, 31 to 33, 38, and 80 exhibited high permeability through mucosa. Particularly, formulation Nos. 8 and 80 containing C17MGE, or C22MGE and HPC exhibited much higher permeability through mucosa than that of the commercially available mucosal application formulations (Aftach® and Kenalog®). This showed that the former formulations largely enhance transmucosal absorption of an active ingredient.

Regarding formulation Nos. 8 and 80, the relative amount of TA permeated after 4 hours was larger than the relative amount of TA permeated after 8 hours, which indicated that the formulations were able to deliver the drug more effectively in a shorter time.

This result demonstrated that a formulation comprising the liquid crystal-forming lipid of the present invention and a water soluble polymer such as HPC not only has a high mucoadhesive property or skin adhesive property but can bring about high drug permeability through mucosa and markedly enhance transmucosal absorption of drug.

[Example 13] Preparation of Spray Formulation

The liquid crystal-forming lipid C17MGE and Pluronic F-127 were mixed for 5 minutes with a vortex mixer. Then, an aqueous fluorescein sodium (FL-Na) solution with a concentration of 790 μg/g was added thereto, and the mixture was homogenized (8000 rpm, 5 min) using a high-speed homogenizer (Polytron PT-3100, Kinematica AG, Switzerland) to prepare a liquid crystal gel (formulation No. 58). The composition of formulation No. 58 had a ratio of liquid crystal-forming lipid:Pluronic F-127:aqueous FL-Na solution of 1:0.1:1 (weight ratio). Formulation No. 58 had an FL-Na concentration of 376 μg/g.

Ethanol was added to formulation No. 58 at a ratio of formulation No. 58:ethanol of 1:0.5 or 1:1 (weight ratio), mixed for 5 minutes with a vortex mixer, and the resulting solution was filled into a manual 5 mL spray vial (No. 2, Maruemu Corp., Japan) to prepare pump spray formulation Nos. 50 and 51.

Formulation No. 50 or 51 (solution) was added to an aerosol container (Daizo Corp., Japan), and a valve for liquefied petroleum gas (LPG) filling was attached to the container, into which the propellant LPG was then filled to prepare aerosol formulation Nos. 52 and 53. The composition of formulation No. 52 has a ratio of formulation No. 50:LPG of 1.5:4 (weight ratio). The composition of formulation No. 53 has a ratio of formulation No. 51:LPG of 1:2 (weight ratio).

Spray formulation Nos. 54 to 57 were prepared according to the same composition and the same method as in formulation Nos. 50 to 53 except that C22MGE was used instead of C17MGE.

FL-Na concentrations in formulation Nos. 50 to 57 were set so as to have 376 sg/g, which was the same as the FL-Na concentration of formulation No. 58 when ethanol and LPG were completely volatilized after spraying.

For comparative controls, formulation No. 59 containing an aqueous FL-Na solution and ethanol mixed at a weight ratio of 1:1 (FL-Na concentration of 376 µg/g), and formulation No. 60 which was a 1 mm aqueous FL-Na solution (FL-Na concentration of 376 µg/g) were prepared.

Table 10 shows the compositional ratios (weight ratios) of formulation Nos. 50 to 60.

exhibited approximations and was 0.723 g/sec for formulation No. 52, 0.868 g/sec for formulation No. 53, 0.726 g/sec for formulation No. 56, and 0.711 g/sec for formulation No. 57.

All of formulation Nos. 52, 53, 56, and 57 were sprayed in the form of a very fine mist. Ethanol was thereby volatilized instantly. Each sprayed formulation was fixed on the glass surface without running down even when the formulation was sprayed for 1 second and the glass surface was inclined at 45 degrees after 60 seconds.

On the other hand, in the case of spraying 0.19 g, 0.29 g, 0.19 g, and 0.24 g of pump spray formulation Nos. 50, 51, 54, and 55, respectively, containing no LPG, all of these 4 types of formulations sprayed ran down on the glass surface by inclining the glass surface at 45 degrees after 60 seconds.

The aerosol formulation of the present invention did not run down from an application site even immediately after spraying, demonstrating that the formulation can be applied exceedingly effectively.

2. Measurement of Particle Size Distribution

The spray formulation of the present invention can form nanosized fine particles immediately after spraying.

Spray formulation Nos. 50 to 57 were each sprayed into a beaker for 1 second. The obtained composition was diluted about 1000-fold with distilled water to prepare a measurement sample. A particle size distribution, and a zeta potential indicating a particle surface charge were measured by the dynamic light scattering method using Zetasizer Nano-ZS (manufactured by Malvern Panalytical Ltd.).

Table 11 shows the average particle size (nm) (Z-Average), PdI (polydispersity index), and the zeta potential (mV) obtained as average values from triplicate measurements. All the formulations were found to become emulsions in a favorable state.

TABLE 10

| Formulation No. | 50 | 51 | 52 | 53 | 54 | 55 |
|---|---|---|---|---|---|---|
| Code Name | C17-NE33 | C17-NE50 | C17-NE33-L | C17-NE59-L | C22-NE33 | C22-NE50 |
| C17MGE | 31.75 | 23.81 | 8.66 | 7.94 | | |
| C22MGE | | | | | 31.75 | 23.81 |
| Aqueous FL-Na solution | 31.75 | 23.81 | 8.66 | 7.94 | 31.75 | 23.81 |
| Pluronic F127 | 3.17 | 2.38 | 0.87 | 0.79 | 3.17 | 2.38 |
| Ethanol | 33.33 | 50.00 | 9.09 | 16.67 | 33.33 | 50.00 |
| LPG | | | 72.73 | 66.67 | | |
| Total | 100 | 100 | 100 | 100 | 100 | 100 |
| FL-Na concentration (μg/g) | 248 | 186 | 67.7 | 62.1 | 248 | 186 |

| Formulation No. | 56 | 57 | 58 | 59 | 60 |
|---|---|---|---|---|---|
| Code Name | C22-NE33-L | C22-NE50-L | N | E50 | FL-Na aq |
| C17MGE | | | 47.62 | | |
| C22MGE | 8.66 | 7.94 | | | |
| Aqueous FL-Na solution | 8.66 | 7.94 | 47.62 | 50 | 100 |
| Pluronic F127 | 0.87 | 0.79 | 4.76 | | |
| Ethanol | 9.09 | 16.67 | | 50 | |
| LPG | 72.73 | 66.67 | | | |
| Total | 100 | 100 | 100 | 100 | 100 |
| FL-Na concentration (μ/g) | 67.7 | 62.1 | 376 | 376 | 376 |

[Example 14] Characteristics Test of Spray Formulation

1. Spraying Test

Aerosol formulation Nos. 52, 53, 56, and 57 prepared in Example 13 were each shaken 5 times immediately before spraying and then sprayed vertically downward to a glass surface from a distance of 10 cm.

A spray output per spraying time was calculated as to these aerosol formulations at 1-second intervals from 1 to 5 seconds. As a result, the spray output per second (g/sec)

TABLE 11

| Formulation | Average particle size (nm) | PdI | Zeta potential (mV) |
|---|---|---|---|
| No. 50 | 200.1 | 0.234 | −15.5 |
| No. 51 | 174.7 | 0.152 | −36.7 |
| No. 52 | 184.1 | 0.199 | −22.4 |
| No. 53 | 183.4 | 0.193 | −34.2 |
| No. 54 | 174.7 | 0.102 | −25.7 |
| No. 55 | 166.4 | 0.091 | −21.2 |
| No. 56 | 175.5 | 0.106 | −25.5 |
| No. 57 | 180.2 | 0.120 | −29.8 |

3. Small-Angle X-Ray Diffraction

Aerosol formulation Nos. 52, 53, 56, and 57 were each sprayed into a centrifugal tube for 3 seconds. Then, a composition obtained by adding 5 mL of purified water thereto was enclosed in a marked tube and subjected to small-angle X-ray scattering diffractometry using a small-angle X-ray scattering (SAXS) apparatus (manufactured by Rigaku Corp., Nano-Viewer) to determine a non-lamellar liquid crystal structure.

Figure 6A:
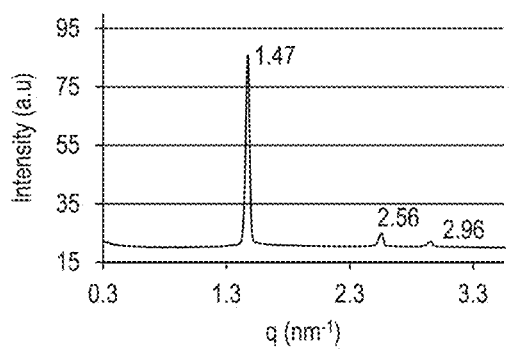
FIGS. 6A, 6B, 6C, 6D and 6E are diagrams showing results of small-angle X-ray diffraction.
Figure 6B:
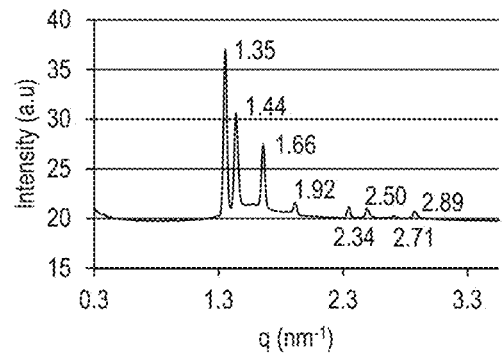
Figure 6C:
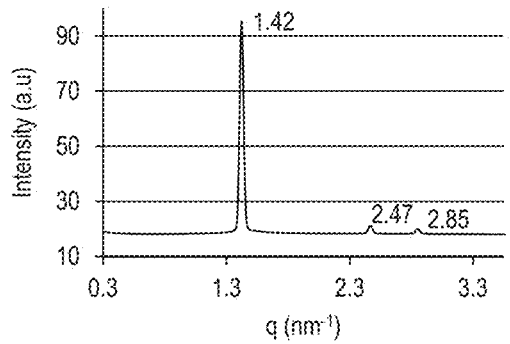
Figure 6D:
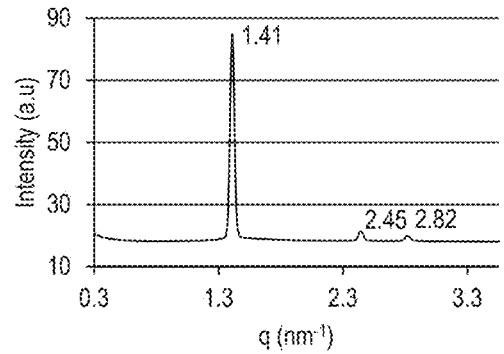

At least 3 scattering peaks were observed in the small-angle X-ray scattering diffraction of the composition obtained by spraying formulation No. 52, 56, or 57 (FIGS. 6A, 6C, and 6D). The peak value ratio indicated the ratio of 1:√3:2 peculiar to reverse hexagonal liquid crystals. Accordingly, these samples were found to form reverse hexagonal liquid crystals.

At least 8 scattering peaks were observed in the small-angle X-ray scattering diffraction of the composition obtained by spraying formulation No. 53 (FIG. 6B). The peak value ratio indicated the ratio of √2:√3:√4:√8 peculiar to cubic liquid crystals belonging to the crystallographic space group Pn3m, and the ratio of 1:√3:2 peculiar to reverse hexagonal liquid crystals. Accordingly, these samples were found to form mixtures of cubic liquid crystals belonging to the crystallographic space group Pn3m, and reverse hexagonal liquid crystals.

Figure 6E:
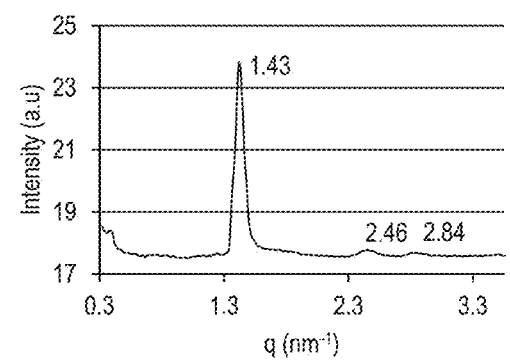

Also, formulation No. 56 was sprayed into a petri dish for 1 second and then left for about 3 minutes. The obtained white sample was embedded directly in a pinhole slit and similarly subjected to small-angle X-ray scattering diffractometry to determine a non-lamellar liquid crystal structure. As a result, at least 3 scattering peaks were observed. The peak value ratio indicated the ratio of 1:√3.2 peculiar to reverse hexagonal liquid crystals (FIG. 6E). Accordingly, this sample was found to form reverse hexagonal liquid crystals.

These aerosol formulations were shown to be able to form a non-lamellar liquid crystal structure and thus found to form a non-lamellar liquid crystal structure regardless of whether or not to further add water after spraying.

[Example 15] In Vitro Test on Permeability Through Skin

A three-drug mixed anesthetic (0.15 mg/kg medetomidine hydrochloride, 2 mg/kg midazolam, and 2.5 mg/kg butorphanol tartrate) was intraperitoneally administered to each of male WBN/ILA-Ht hairless rats (body weight of 200 to 250 g, 8 weeks old), and the abdominal skin area was shaved. Then, a total of 4 pieces (2 cm×2 cm each) on the right and left sides flanking the median line were excised from the abdominal skin. Subcutaneous fat and blood on the dermal side were carefully removed from each piece with scissors to prepare a rat abdominal skin.

6.0 mL of a phosphate buffer (PB) of pH 7.4 was added to the receiver cell of the same vertical diffusion cell as in Example 11 (cell capacity of 6.0 mL, effective diffusion area of 1.77 cm$^2$) (FIG. 4), and the rat abdominal skin was set up therein, instead of the dialysis membrane used in Example 11. After the horny cell layer (at the donor cell side) was hydrated for 1 hour by the addition of 1.0 mL of PB, each formulation was applied thereon to start measurement.

The formulations used were formulation Nos. 50 to 53, and 56 to 60 prepared in Example 13. The amounts applied of the formulations were 0.218 g of formulation No. 50 (containing 54 μg of FL-Na), 0.290 g of formulation No. 51 (containing 54 μg of FL-Na), 0.723 g of formulation No. 52 (containing 49 μg of FL-Na) by spraying for 1 second, 0.868 g of formulation No. 53 (containing 54 μg of FL-Na) by spraying for 1 second, 0.726 g of formulation No. 56 (containing 49 μg of FL-Na) by spraying for 1 second, 0.711 g of formulation No. 57 (containing 44 μg of FL-Na) by spraying for 1 second, 0.145 g of formulation No. 58 (containing 54 μg of FL-Na), 1 mL of formulation No. 59 (containing 376 μg of FL-Na), and 1 mL of formulation No. 60 (containing 376 μg of FL-Na).

In order to measure the amount of FL-Na permeated through the skin from the formulation, the aqueous solution in the receiver cell was sampled by 500 μL each over time and replenished with the same amount of PB during each sampling. The inside of the cell was kept at 32° C., and the inside of the receiver cell was constantly stirred with a magnetic stirrer.

Each sample solution collected over time was centrifuged (21,500×g, 5 min, 4° C.). Then, the resulting supernatant was assayed with a fluorescence spectrophotometer (RF-5300PC; Shimadzu Corp., Japan) (excitation wavelength of 485 nm, fluorescence wavelength of 535 nm) to determine an FL-Na concentration of the sample solution.

Figure 7:
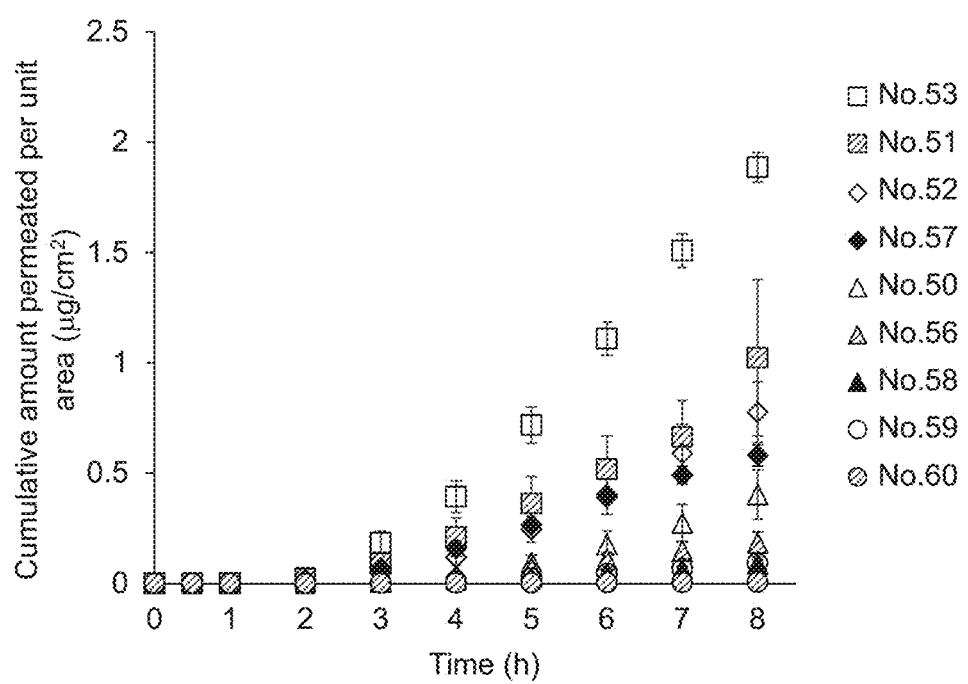
FIG. 7 is a diagram showing FL-Na permeation behavior through the skin from a spray formulation. Each value is indicated by mean±standard error (S.E.).

FIG. 7 shows FL-Na permeation behavior through the skin from each formulation. The ordinate of the graph shows an average cumulative amount of FL-Na permeated through the skin (an average value from the test conducted three or four times) per unit effective permeation area (μg/cm$^2$) based on the effective diffusion area (1.77 cm$^2$) of the cell, calculated from the measured FL-Na concentration.

Table 12 shows the cumulative amount of FL-Na permeated through the skin per unit effective permeation area at 4 hours and 8 hours after formulation application, and a relative amount of FL-Na permeated as compared with formulation No. 60 (control).

TABLE 12

| | 4 hours later | | 8 hours later | |
|---|---|---|---|---|
| Formulation No./Code Name | Cumulative amount of FL-Na permeated/ effective permeation area (μg/cm$^2$) | Relative amount permeated (fold) | Cumulative amount of FL-Na permeated/ effective permeation area (μg/cm$^2$) | Relative amount permeated (fold) |
| No. 50/C17-NE33 | 0.0310 | 27 | 0.403 | 71 |
| No. 51/C17-NE50 | 0.210 | 184 | 1.02 | 179 |
| No. 52/C17-NE33-L | 0.118 | 104 | 0.775 | 136 |
| No. 53/C17-NE50-L | 0.393 | 345 | 1.89 | 332 |
| No. 56/C22-NE33-L | 0.0376 | 33 | 0.183 | 32 |
| No. 57/C22-NE50-L | 0.157 | 138 | 0.580 | 102 |
| No. 58/N | 0.0156 | 14 | 0.0885 | 16 |
| No. 59/E50 | 0.00976 | 9 | 0.0910 | 16 |
| No. 60/FL-Na Aq | 0.00114 | 1 | 0.00569 | 1 |

Spray formulation Nos. 50 to 53, 56, and 57 exhibited much higher permeability through the skin than that of the aqueous FL-Na solution (formulation No. 60), the liquid crystal gel (formulation No. 58), and the 50% aqueous ethanol solution (formulation No. 59). The cumulative amounts of FL-Na permeated through the skin at 4 hours after application of pump spray formulation Nos. 50 and 51 exhibited high values of 27 times and 184 times, respectively, the amount of formulation No. 60. The cumulative amounts of FL-Na permeated through the skin at 4 hours after application of aerosol formulation Nos. 52, 53, 56, and 57 exhibited higher values of 104 times, 345 times, 33 times, and 138 times, respectively, the amount of formulation No. 60. The cumulative amounts of FL-Na permeated through the skin at 8 hours after application also exhibited high values in a similar manner.

Also considering that aerosol formulation Nos. 52, 53, 56, and 57 did not run down from an application site even immediately after spraying and these formulations can be applied more effectively than pump spray formulation No. 50 or 51 containing no LPG as shown in Table 14, these results showed that the formulations can be used as exceedingly useful formulations promoting permeation through the skin.

[Example 16] Preparation of Tape Formulation

The liquid crystal-forming lipid C17MGE, phytantriol (PHY, Tokyo Chemical Industry Co., Ltd., Japan), or C22MGE, and an aqueous FL-Na solution containing FL-Na dissolved in a phosphate buffer (PB) of pH 7.4 were filled at a weight ratio of 1:1, 2:1, or 3:1 into a gas tight syringe (MS-GAN025, Ito Seisakusho Co., Ltd., Japan) and homogenously mixed to obtain a liquid crystal gel. The FL-Na concentration of the aqueous FL-Na solution was set such that the final FL-Na concentration in an adhesive layer as mentioned later was 10 mm. PHY is semisolid at ordinary temperatures and was therefore used after being melted with a hot stirrer (100° C., 30 min).

Figure 8:
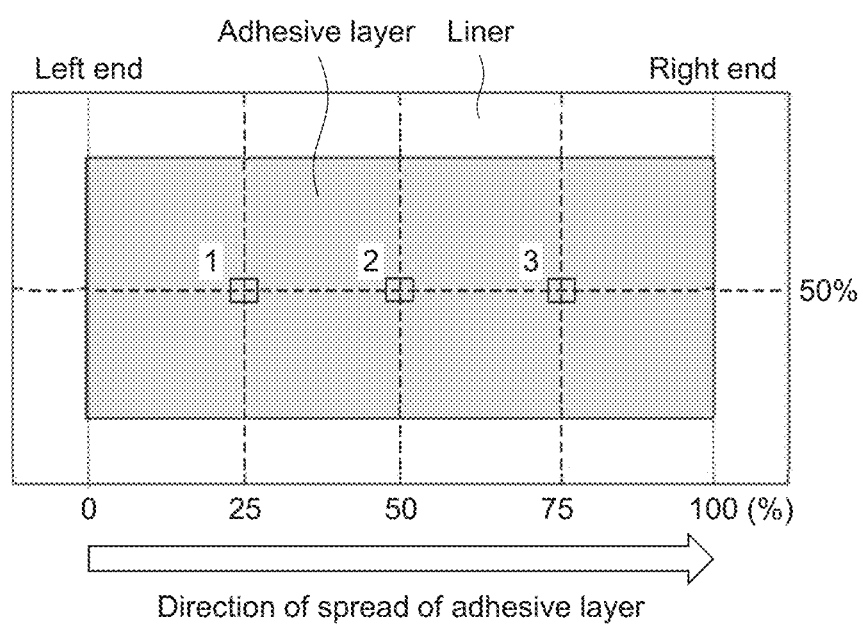
FIG. 8 is a schematic diagram showing the spread of an adhesive layer on a liner. The arrow depicts the direction of spread of the adhesive layer.
Figure 9A:
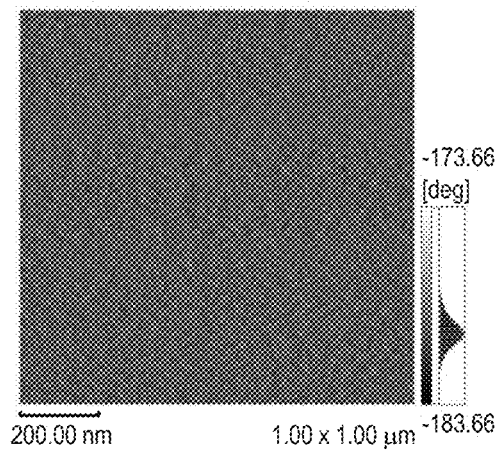
FIGS. 9A, 9B, 9C, and 9D show photographs showing phase images of adhesive layer surfaces of tape formulations.
Figure 9B:
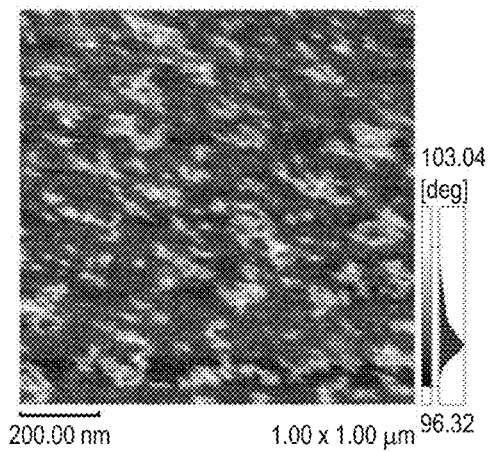
Figure 9C:
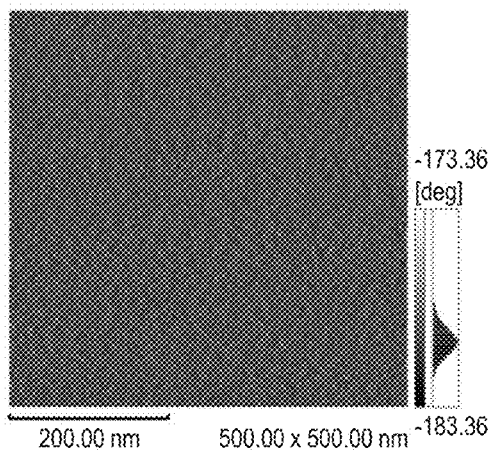
Figure 9D:
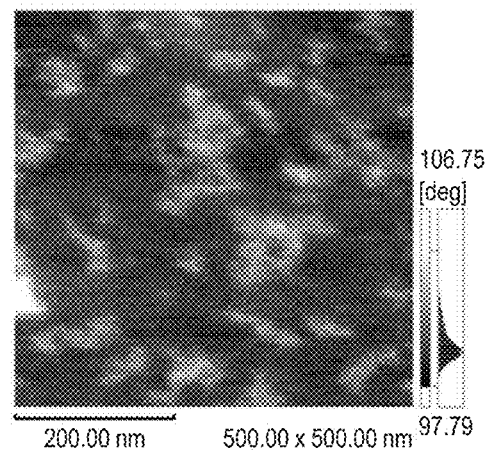

Acrylic adhesive DURO-TAK® (387-2516, Henkel AG & Co. KGaA, Germany) was added to the liquid crystal gel such that the weight ratio of the adhesive to the whole adhesive layer was 80%, followed by mixing using a magnetic stirrer (500 rpm, 5 min). This mixture was placed on the left end (at position of 0%) of a silicone-coated polyethylene terephthalate (PET) film liner (Filmbyna® 75E-0010 BD, Fujimori Kogyo Co., Ltd., Japan), and spread from the left end (at position of 0%) toward the right end (at position of 100%) using No. 510 Baker Type Film Applicator (Yasuda Seiki Company, Japan) set to a coating thickness of 1 mil (25.4 µm) (FIG. 8). The spread adhesive layer was dried for 30 minutes in a chamber with a temperature of 20±2° C. and a humidity of 20±5% and further dried for 30 minutes in an incubator with a temperature of 32° C. and a humidity of 20±2%. A 75 µm thick PET film support (Filmbyna®, Fujimori Kogyo Co., Ltd., Japan) was pressure-bonded to the thus dried adhesive layer using SN-Engraving Rubber Roller No. 3 (Taniguchi Shoyudo Co., Ltd., Japan) to prepare tape formulations (formulation Nos. 61 to 69).

Table 13 shows the final compositional ratios (weight ratios) of the adhesive layers of formulation Nos. 61 to 69.

TABLE 13

| Formulation No. | 61 | 62 | 63 | 64 | 65 | 66 |
|---|---|---|---|---|---|---|
| Code Name | T-D80M10 | T-D80M13 | T-D80M15 | T-D80P10 | T-D80P13 | T-D80P15 |
| C17MGE | 10 | 13.35 | 15 | | | |
| PHY | | | | 10 | 13.35 | 15 |
| C22MGE | | | | | | |
| DURO-TAK | 80 | 80 | 80 | 80 | 80 | 80 |
| FL-Na solution | 10 | 6.65 | 5 | 10 | 6.65 | 5 |
| Total | 100 | 100 | 100 | 100 | 100 | 100 |

| Formulation No. | 67 | 68 | 69 |
|---|---|---|---|
| Code Name | | | |
| C17MGE | | | |
| PHY | | | |
| C22MGE | 10 | 13.35 | 15 |
| DURO-TAK | 80 | 80 | 80 |
| Aqueous FL-Na solution | 10 | 6.65 | 5 |
| Total | 100 | 100 | 100 |

Tape formulation Nos. 70 to 72 containing the liquid crystal-forming lipid (C17MGE) and the acrylic adhesive (pressure sensitive adhesive) DURO-TAK® with a weight ratio of 90%, 70%, or 20%, and tape formulation No. 73 containing no liquid crystal-forming lipid and containing the acrylic adhesive DURO-TAK® at a weight ratio of 90% were also prepared according to the compositional ratios (weight ratios) shown in Table 14 in the same way as above.

TABLE 14

| Formulation No. | 70 | 71 | 72 | 73 |
|---|---|---|---|---|
| Code Name | T-D90M5 | T-D70M15 | T-D20M40 | T-D90M0 |
| C17MGE | 5 | 15 | 40 | |
| PHY | | | | |
| C22MGE | | | | |
| DURO-TAK | 90 | 70 | 20 | 90 |
| Aqueous FL-Na solution | 5 | 15 | 40 | 10 |
| Total | 100 | 100 | 100 | 100 |

[Example 17] Characteristics Test of Tape Formulation

1. Image Analysis

Tape formulation Nos. 61 to 73 after drying of the adhesive layer and before pressure bonding of a PET film support in Example 16 were subjected to image analysis by normal photography and under a fluorescence microscope.

Images of the normal photography were obtained by photographing the whole of each tape formulation from 20 cm above using a digital camera (D5300, Nikon Corp., Japan).

Images of the fluorescence microscope were obtained by photographing 3 sites, i.e., at the positions of 25% (site 1 in FIG. 8), 50% (site 2 in FIG. 8), and 75% (site 3 in FIG. 8) from the center of the left end of each tape formulation, using a fluorescence microscope (BZ-X700, Keyence Corp., Japan). Photography conditions for the fluorescence microscope involved objective lens CFI Plan Apo λ 2×, fluorescence filter GFP (OP-87763 BZ-X filter), an excitation wavelength of 470/40 nm, an absorption wavelength of 525/50 nm, a dichroic mirror wavelength of 495 nm, and a gain of +6 dB. The exposure time was set to $1/175$ s for the formulations containing the liquid crystal-forming lipid and $1/5$ s for the formulation containing no liquid crystal-forming lipid.

All the adhesive layers of tape formulation Nos. 61 to 70 containing DURO-TAK® at a weight ratio of 80 or 90% were uniformly spread. On the other hand, the adhesive layer of tape formulation No. 71 containing DURO-TAK® at a weight ratio of 70% was slightly inferior in uniformity to formulation Nos. 61 to 70. Any of the adhesive layers of tape formulation No. 72 containing DURO-TAK® at a weight ratio of 20%, and tape formulation No. 73 containing no liquid crystal-forming lipid and containing DURO-TAK® at a weight ratio of 90% were not uniformly spread.

These results showed that a uniform tape formulation can be prepared by the addition of DURO-TAK® at a weight ratio equal to or more than a given level (desirably 70% or more, more desirably 80% or more) and the liquid crystal-forming lipid of the present invention.

2. Thickness of Adhesive Layer

The thickness of the whole tape formulation was measured using a hand clipper (Thickness Gauge, Teclock Corp., Japan). The thicknesses of the support (20 μm) and the liner (80 μm) were subtracted from the measured value to determine the thickness of the adhesive layer of the tape formulation.

All the thicknesses of the adhesive layer at 3 sites, i.e., at the positions of 25% (site 1 in FIG. 8), 50 (site 2 in FIG. 8), and 75% (site 3 in FIG. 8) from the center of the left end (FIG. 8) of formulation No. 63, 66, or 69, were 15±5 μm (average values from 6 measurements).

Accordingly, the adhesive layers of these tape formulations were found to have a uniform thickness.

3. Phase Image Analysis

The shape of the tape formulation was observed at 1 μm×1 μm and 0.5 μm×0.5 μm observation fields of view under a scanning probe microscope (SPM-9700HT, Shimadzu Corp., Japan), followed by phase observation.

As a result of observing the shapes of formulation Nos. 63 and 73, smooth surface shapes were observed for both. As a result of observing the phases of these formulations, no phase image was observed in formulation No. 73 whereas characteristic phase images were observed in formulation No. 63, as shown in FIGS. 9A-9D.

The results revealed that: the physical properties of an adhesive layer surface differ depending on the presence or absence of the liquid crystal-forming lipid contained; and a tape formulation containing the liquid crystal-forming lipid and DURO-TAK® has surface characteristics typical of a structure having any regularity.

Figure 10:
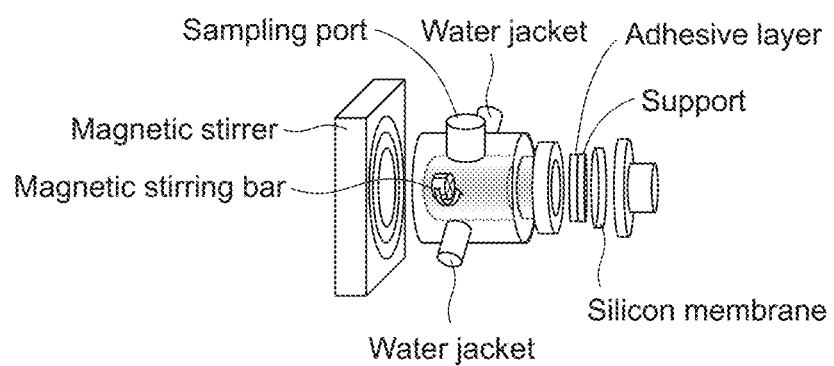
FIG. 10 is a schematic diagram of the structure of a horizontal diffusion cell.

[Example 18] In Vitro Releasing Property Test 3.0 mL of PB was added to the receiver cell of the horizontal diffusion cell (cell capacity of 3.0 mL, effective diffusion area of 0.95 cm$^2$; Kobayashi Glass Co., Ltd.) shown in FIG. 10, and each formulation was applied thereto at the donor cell side, followed by starting a test on the in vitro releasing property of the formulation. The formulations used were formulation Nos. 61 to 69 and 73.

In order to measure the amount of FL-Na released from the formulation, the aqueous solution in the receiver cell was sampled by 500 μL each over time and replenished with the same amount of PB during each sampling. The inside of the cell was kept at 32° C., and the inside of the receiver cell was constantly stirred with a magnetic stirrer.

Each sample solution collected over time was centrifuged (21,500×g, 5 min, 4° C.). Then, the resulting supernatant was assayed with a fluorescence spectrophotometer (RF-5300PC; Shimadzu Corp., Japan) (excitation wavelength of 485 nm, fluorescence wavelength of 535 nm) to determine an FL-Na concentration of the sample solution.

Figure 11:
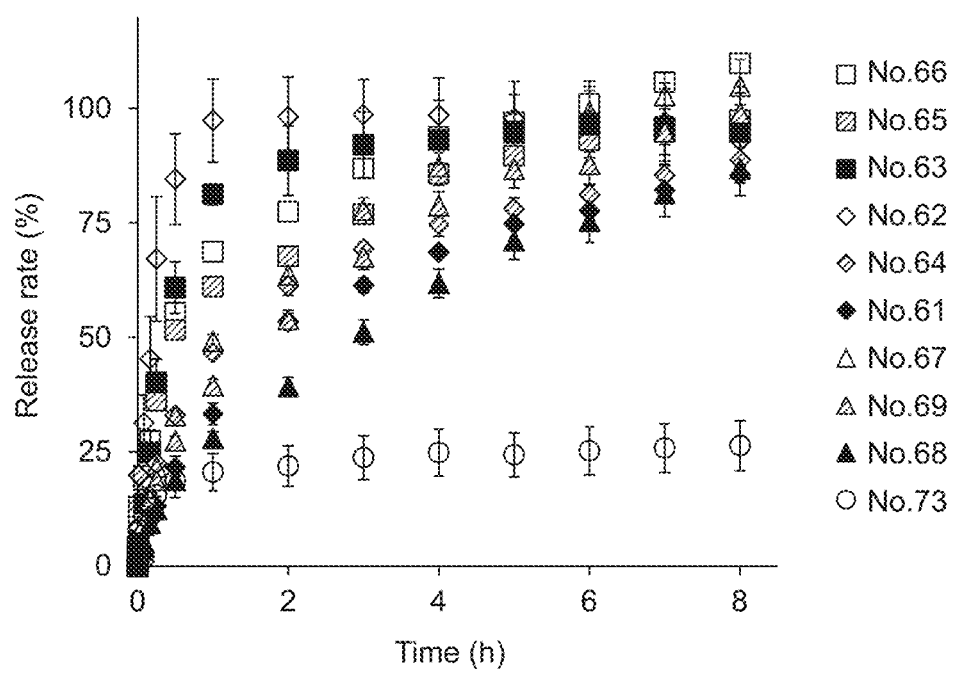
FIG. 11 is a diagram showing FL-Na release behavior from a tape formulation.

FIG. 11 shows FL-Na release behavior from each formulation. The ordinate of the graph shows an average cumulative FL-Na release rate (%) (an average value from the test conducted three or four times) based on the extraction test, calculated from the measured FL-Na concentration.

Table 15 shows a cumulative FL-Na release rate (%) at 1 hour and 4 hours after formulation application. The cumulative FL-Na release rate (%) was calculated according to the following expression.

$$\text{Cumulative FL-Na release rate (\%)} = \text{Cumulative amount of FL-Na released/Amount of FL-Na applied} \times 100$$

TABLE 15

| Formulation No./ Code Name | 1 hour later Cumulative FL-Na release rate (%) | 4 hours later Cumulative FL-Na release rate (%) |
|---|---|---|
| No. 61/T-D80M10 | 33.3 | 68.6 |
| No. 62/T-D80M13 | 97.3 | 98.5 |
| No. 63/T-D80M15 | 81.2 | 93.1 |
| No. 64/T-D80P10 | 46.6 | 74.6 |
| No. 65/T-D80P13 | 61.0 | 85.7 |
| No. 66/T-D80P15 | 68.7 | 93.7 |
| No. 67 | 49.1 | 87.3 |
| No. 68 | 27.9 | 61.8 |
| No. 69 | 39.4 | 78.7 |
| No. 73 | 20.5 | 24.8 |

All of formulation Nos. 61 to 69 released FL-Na over time and rapidly. Particularly, formulation Nos. 62, 63, 65, and 66 exhibited a higher cumulative release rate from 1 hour after application, and achieved a release rate close to 100% 4 hours after application. In particular, Nos. 62 and 63 exhibited a release rate that already reached close to 10% 1 hour after application, and thus released FL-Na exceedingly rapidly.

On the other hand, tape formulation No. 73 containing no liquid crystal-forming lipid gradually released FL-Na, and no FL-Na release was seen after the release rate reached about 25% 4 hours after application. This result showed that an enclosed drug cannot be efficiently released in the absence of the liquid crystal-forming lipid.

[Example 19] In Vitro Test on Permeability Through Skin

An in vitro test on permeability through the skin was conducted by applying each of formulation Nos. 61 to 69 as a formulation onto the horny cell layer (at the donor cell side) of rat abdominal skin set up in the vertical diffusion cell (FIG. 4), according to the method described in Example 15. 10 mm aqueous FL-Na solution No. 74 containing FL-Na dissolved in PB was used as a comparative control.

Figure 12:
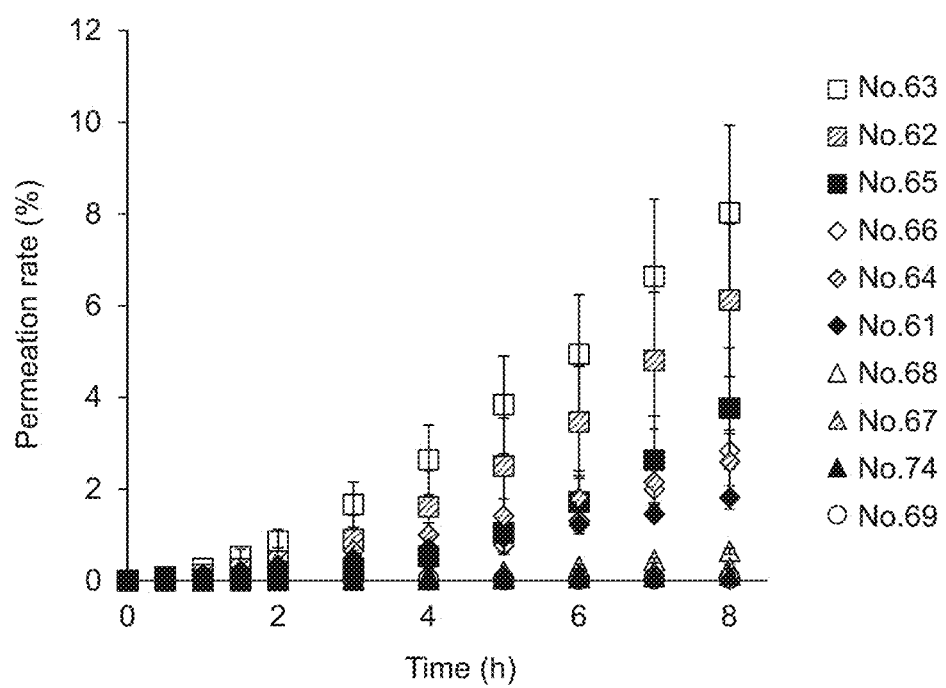
FIG. 12 is a diagram showing FL-Na permeation behavior through the skin from a tape formulation.

FIG. 12 shows FL-Na permeation behavior through the skin from each formulation. The ordinate of the graph shows an average cumulative rate of FL-Na permeation through the skin (%) (an average value from the test conducted three or four times) based on the extraction test, calculated from the measured FL-Na concentration.

Table 16 shows a cumulative rate of FL-Na permeation through the skin (%) at 1 hour and 4 hours after formulation application. The cumulative rate of FL-Na release (%) was calculated according to the following expression.

Cumulative rate of FL-Na release (%)=Cumulative amount of FL-Na permeated/Amount of FL-Na applied×100

TABLE 16

| | 1 hour later | | 4 hours later | |
| --- | --- | --- | --- | --- |
| Formulation No./Code Name | Cumulative rate of FL-Na permeation through skin (%) | Relative amount permeated (fold) | Cumulative rate of FL-Na permeation through skin (%) | Relative amount permeated (fold) |
| No. 61/T-D80M10 | 0.133 | 204 | 0.698 | 24 |
| No. 62/T-D80M13 | 0.135 | 207 | 1.61 | 56 |
| No. 63/T-D80M15 | 0.263 | 404 | 2.64 | 91 |
| No. 64/T-D80P10 | 0.102 | 157 | 0.997 | 34 |
| No. 65/T-D80P13 | 0.0234 | 36 | 0.531 | 18 |
| No. 66/T-D80P15 | 0.0280 | 43 | 0.393 | 14 |
| No. 67 | 0.0118 | 18 | 0.0662 | 2 |
| No. 68 | 0.00611 | 9 | 0.111 | 4 |
| No. 69 | 0.0105 | 16 | 0.0195 | 0.7 |
| No. 74/FL-Na Aq | 0.000651 | 1 | 0.0290 | 1 |

All of tape formulation Nos. 61 to 69 exhibited a markedly increased permeability through the skin as compared with aqueous FL-Na solution No. 74. Formulation Nos. 61 to 63 containing C17MGE exhibited very high permeability through the skin even as compared with tape formulation Nos. 64 to 66 containing PHY. Considering that in Example 18, the in vitro releasing property did not largely differ between the tape formulations containing C17MGE or C22MGE and the tape formulations containing PHY, the high permeability through the skin exhibited by the tape formulations containing C17MGE or C22MGE was a surprising result. Formulation Nos. 62 and 63 exhibited an increased permeability through the skin more than expected from the content percentage of the liquid crystal-forming lipid, as compared with formulation No. 61, 4 hours or later after application (FIG. 12).

[Example 20] Preparation of Emulsion

The liquid crystal-forming lipid C17MGE or glyceryl monooleate (GMO, Rikemal XO-100, NOF Corp.), the drug tranilast (Tokyo Chemical Industry Co., Ltd., Japan), and ethanol (only for No. 76) were mixed according to the content ratios (weight ratios) shown in Table 17, and then dissolved in a hot water bath of 80° C. To the obtained lipid-mixed solution, an aqueous solution containing Pluronic® F127 (Unilube® 70DP-950B, NOF Corp., or Aldrich P2443) dissolved in purified water was added, followed by stirring with a scoopula or a vortex mixer to prepare a suspension. This suspension was further ultrasonicated for 5 minutes at an amplitude of 20% using an ultrasonic homogenizer (Sonics Vibra-Cell VCX-750, manufactured by Sonics & Materials, Inc.) to prepare white emulsion Nos. 75 to 77 containing fine particles. These emulsions were each prepared in an amount of 10 g. Tranilast, known as an antiallergic agent, was also examined for a therapeutic effect on neurological diseases (US 2011/0112187 A1).

In the emulsions containing the lipid at 200%, C17MGE was successfully dispersed with Pluronic® F127 in an amount of 1% whereas GMO was not able to be dispersed. Hence, GMO was dispersed with Pluronic® F127 in an amount of 5% (No. 77). Formulation No. 78 was prepared as a comparative control by adding tranilast at 0.5% to physiological saline (Table 17).

TABLE 17

| Formulation No. | 75 | 76 | 77 | 78 |
| --- | --- | --- | --- | --- |
| Code Name | TLMGE | TLMGE + EtOH | TLGMO | TLNSS |
| C17MGE | 20 | 20 | | |
| GMO | | | 20 | |
| Tranilast | 0.5 | 0.5 | 0.5 | 0.5 |
| Pluronic F127 | 1 | 1 | 5 | |
| Ethanol | | 10 | | |
| Purified water | 78.5 | 68.5 | 74.5 | |
| Physiological saline | | | | 99.5 |
| Total | 100 | 100 | 100 | 100 |

[Example 21] Physical Property Evaluation of Emulsion

The particle size distributions and small-angle X-ray scattering diffraction of emulsion Nos. 75 to 77 prepared in Example 20, and the viscosities and tranilast enclosure efficiency of emulsion Nos. 75 and 76 were measured.

The particle size distribution was measured by the dynamic light scattering method using Zetasizer Nano-ZS (manufactured by Malvern Panalytical Ltd.). Measurement samples were prepared by diluting each emulsion 1000-fold with distilled water. Table 18 shows the average particle size (nm) (Z-Average), PdI (polydispersity index), and the zeta potential (mV) obtained as average values from triplicate measurements as to each measurement sample.

Each emulsion was stable without visible aggregates throughout the experiment. This was supported by moderate average particle sizes, PdI, and zeta potentials.

The small-angle X-ray scattering diffraction was measured on each emulsion enclosed in a marked tube, using a small-angle X-ray scattering (SAXS) apparatus (manufactured by Rigaku Corp., Nano-Viewer).

Figure 13A:
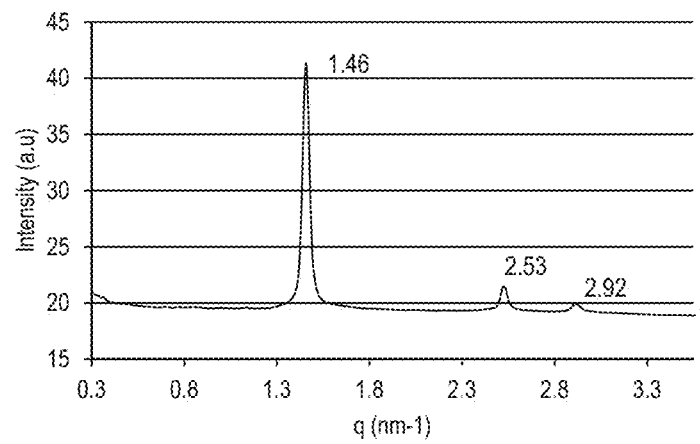
FIGS. 13A, 13B and 13C are diagrams showing results of small-angle X-ray diffraction.

At least 3 scattering peaks were observed in the small-angle X-ray scattering diffraction of emulsion No. 75 (FIG. 13A). The peak value ratio indicated the ratio of $1:\sqrt{3}:2$ peculiar to reverse hexagonal liquid crystals. Accordingly, this emulsion was found to be a liquid crystal emulsion containing fine particles of reverse hexagonal liquid crystals dispersed in an aqueous phase (hexasome).

Figure 13B:
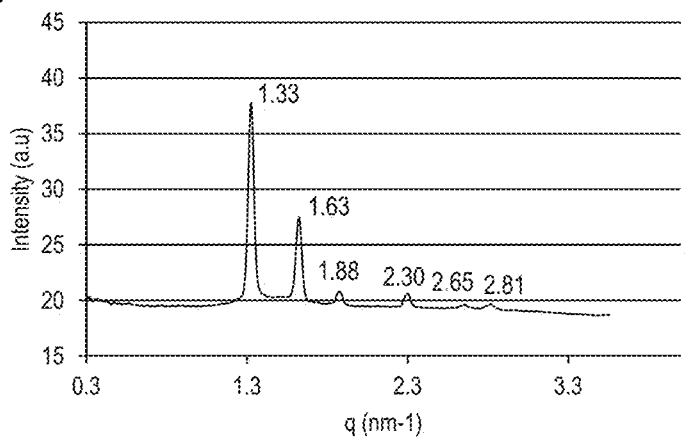

At least 4 scattering peaks were observed in the small-angle X-ray scattering diffraction of emulsion No. 76 (FIG. 13B). The peak value ratio indicated the ratio of $\sqrt{2}:\sqrt{3}:\sqrt{29}$ $4:\sqrt{8}$ peculiar to cubic liquid crystals belonging to the crystallographic space group Pn3m. Accordingly, this emulsion was found to be a liquid crystal emulsion containing fine particles of cubic liquid crystals belonging to the crystallographic space group Pn3m, dispersed in an aqueous phase (cubosome).

Figure 13C:
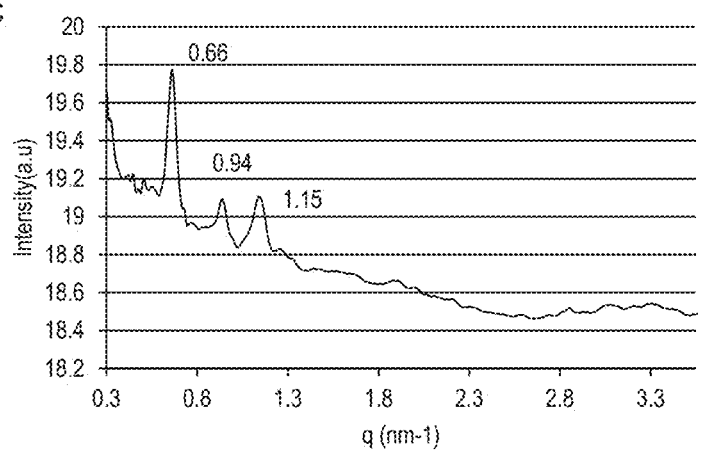

At least 3 scattering peaks were observed in the small-angle X-ray scattering diffraction of emulsion No. 77 (FIG. 13C). The peak value ratio indicated the ratio of $\sqrt{2}:\sqrt{4}:\sqrt{6}$ peculiar to cubic liquid crystals belonging to the crystallographic space group Im3m. Accordingly, this emulsion was found to be a liquid crystal emulsion containing fine particles of cubic liquid crystals belonging to the crystallographic space group Im3m, dispersed in an aqueous phase (cubosome).

A viscometer (RE215H; cone rotor 0.80°×R24, Toki Sangyo Co., Ltd.) was used for measuring the viscosity. Table 18 shows the viscosity (mPa·s) of each emulsion measured at a temperature of 25° C. and a rotational speed of 50 rpm. All the viscosities thus measured fell within a range that permitted spraying.

In order to calculate the enclosure efficiency, each emulsion was centrifuged (21,500×g, 15 min, 4° C.). Then, the resulting supernatant was isolated and diluted 10-fold with acetonitrile, and tranilast was quantified by use of liquid chromatography-tandem mass spectrometry (LC-MS/MS). The enclosure efficiency was calculated according to the following expression.

$$\% \, EE = \frac{TL_{total} - TL_{free}}{TL_{total}} * 100$$

In the expression, % EE, $TL_{total}$, and $TL_{free}$ denote enclosure efficiency, a total tranilast concentration in the emulsion, and a tranilast concentration in the supernatant, respectively.

As shown in Table 18, all the emulsions had high enclosure efficiency and exhibited high ability to incorporate tranilast into the liquid crystal structure within the fine particles.

TABLE 18

| Formulation No./Code Name | Average particle size (nm) | PdI | Zeta potential (mV) | Viscosity (mPa · s) | Enclosure efficiency (%) |
|---|---|---|---|---|---|
| No. 75/TLMGE | 326 | 0.39 | −25.5 | 3.5 | 92.0 |
| No. 76/TLMGE + EtOH | 259 | 0.29 | −22.4 | 7.2 | 89.8 |
| No. 77/TLGMO | 179 | 0.13 | −15.5 | — | — |

[Example 22] In Vitro Releasing Property Test 6.0 mL of phosphate buffered saline (PBS; pH 7.4) was added to the receiver cell of the vertical diffusion cell (cell capacity of 6.0 mL, effective diffusion area of 1.77 cm$^2$; Kobayashi Glass Co., Ltd.) shown in FIG. 4, and a dialysis membrane (cutoff molecular weight=12,000 to 14,000 Da, Sanko Junyaku Co., Ltd., Japan) hydrated in advance was set up therein. Each formulation was applied on the dialysis membrane (at the donor cell side) to start a test on the in vitro releasing property of the formulation. The formulations used were 1 mL each of emulsion formulation Nos. 75 and 76, and comparative control formulation No. 78.

In order to measure the amount of tranilast released from the formulation, the aqueous solution in the receiver cell was sampled by 500 μL each over time and replenished with the same amount of PBS during each sampling. The inside of the cell was kept at 32° C., and the inside of the receiver cell was constantly stirred with a magnetic stirrer.

Acetonitrile was added at a ratio of 1:1 (v/v) to each sample solution collected over time, and the mixture was stirred and then centrifuged (21,500×g, 5 min, 4° C.) to recover a supernatant. 10 μL of the supernatant was injected to an LC/MS/MS system to quantify tranilast.

The LC/MS/MS system used in this measurement was made up of a system controller (CBM-20A, Shimadzu Corp.), a pump (LC-20AD, Shimadzu Corp.), an autosampler (SIL-20ACHT, Shimadzu Corp.), a column oven (CTO-20A, Shimadzu Corp.), a mass spectrometer (4000QTRAP, AB Sciex Pte. Ltd.), and analytical software (Analyst® version 1.4.2, Shimadzu Corp.).

LC/MS/MS measurement conditions were as follows. A column (Shodex ODP2HPG-2A 2.0 mm×10 mm, Showa Denko K.K.) was kept at 40° C. The mobile phase used was acetonitrile:5 mm aqueous ammonium acetate solution containing 0.05% formic acid of 80:20. The flow rate was kept at 0.2 mL/min. Mass spectrometric quantification was carried out on a multiple reaction monitoring (MRM) mode, and transition ions from m/z 328.0 to m/z 191.2 were monitored at a collision energy of 36 eV.

Figure 14:
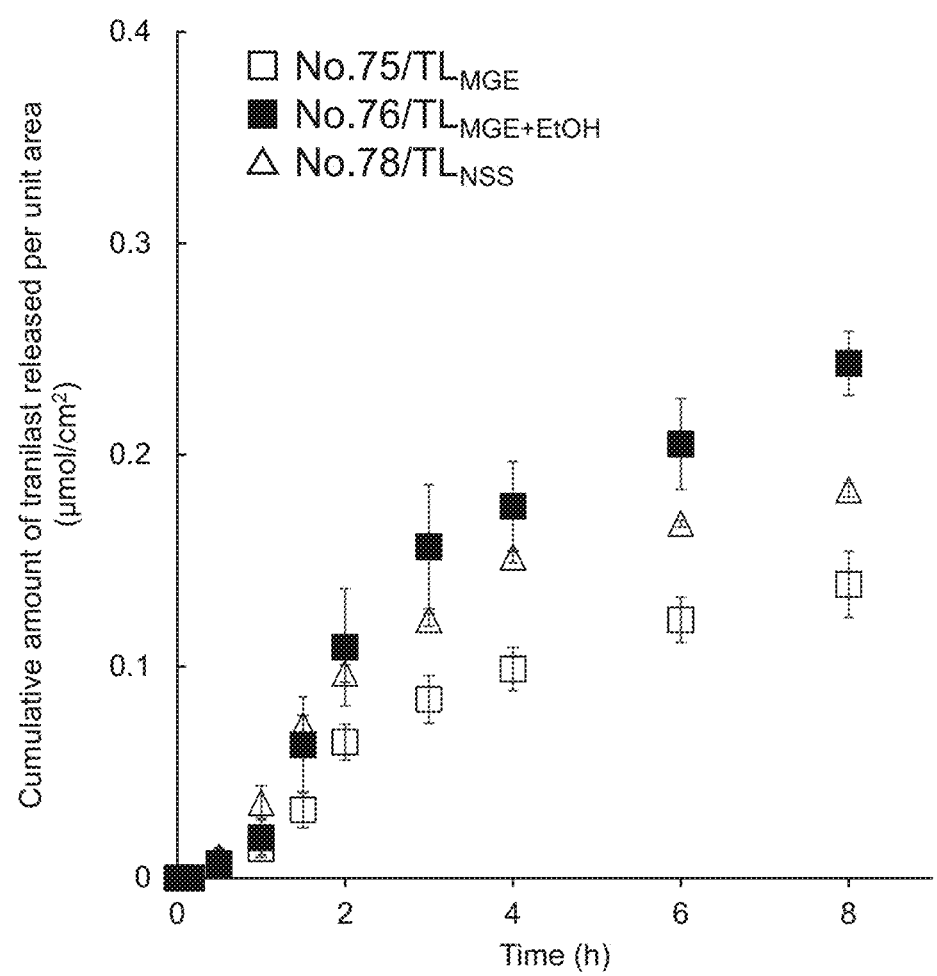
FIG. 14 is a diagram showing tranilast release behavior from each formulation for 8 hours after application. Each value is indicated by mean±standard error (S.E.). The open square depicts formulation No. 75, the filled square depicts formulation No. 76, and the open triangle depicts formulation No. 78.

FIG. 14 shows tranilast release behavior from each formulation for 8 hours after application. The ordinate of the graph shows an average cumulative amount of tranilast released (an average value from the test conducted four times) (μmol/cm$^2$).

The tranilast release behavior from each formulation well correlated with the equation of Higuchi (Higuchi T., J. Pharm. Sci., 52, 1145-1148 (1963)). A tranilast releasing speed (μmol/cm/h$^{0.5}$) calculated from FIG. 14 was as high as 0.17 for formulation No. 76 and was 0.05 for both of Nos. 75 and 78. A cumulative rate of tranilast release (%) at 8 hours after formulation application calculated from FIG. 14 was 1.82, 3.67, and 2.35 for Nos. 75, 76, and 78, respectively. Formulation Nos. 75 and 76 having tranilast enclosed in the liquid crystal structure exhibited a solid releasing property.

[Example 23] Pharmacokinetic Evaluation by Intranasal Administration

Pharmacokinetic evaluation was carried out using Sprague-Dawley rats (male, 7 weeks old, body weight of 230 g±10 g) by intranasal administration of formulation Nos. 75 to 78. First, a three-drug mixed anesthetic (0.375 mg/kg medetomidine hydrochloride, 2.5 mg/kg butorphanol tartrate, and 2 mg/kg midazolam) was intraperitoneally administered to each rat for systemic anesthesia. The tip of a micropipette was inserted by 0.5 cm to the nasal cavity of the rat kept in the supine position, and 10 μL of each formulation was added dropwise thereto to perform intranasal administration.

At predetermined time points (0.17, 0.5, 1, 2, 4, and 8 hours after administration), about 200 μL of blood was collected from the cervical vein of the rat, transferred directly to a heparin-supplemented tube, and immediately centrifuged (21,500×g, 10 min, 4° C.) to obtain plasma. During each blood collection, the same amount of physiological saline as the blood collected was injected to the rat from the tail vein. For some rats, after blood was collected 2, 4, or 8 hours after administration, a three-drug mixed anesthetic was intraperitoneally administered thereto for systemic anesthesia, and then cardiopulmonary perfusion was performed with cold PBS, and the whole brain of the rat was excised. The excised whole brain was dissected into specific regions (olfactory bulb, cortex, brain stem, cerebellum, midbrain, and hippocampus) on ice. The spinal cord was also collected from the sacrificed rats. The collected brain samples were weighed and subsequently cut using scissors. 0.5 mL of acetonitrile was added to each sample, and homogenized at 12,000 rpm at 4° C. for 5 minutes using a homogenizer (Polytron PT1200E, Kinematica AG, Switzerland). The resulting brain homogenate was centrifuged (21,500×g, 5 min, 4° C.) to recover a supernatant. The plasma and the supernatants obtained from the brain homogenate were kept at −30° C. until analysis.

Acetonitrile was added at a ratio of 1:1 (v/v) to 50 µL of the plasma or the supernatant obtained from the brain homogenate, and the mixture was stirred and then centrifuged (21,500×g, 5 min, 4° C.) to recover a supernatant. According to the same method as in Example 22, 10 µL of the obtained supernatant was injected to an LC/MS/MS system to quantify tranilast therein.

Figure 15:
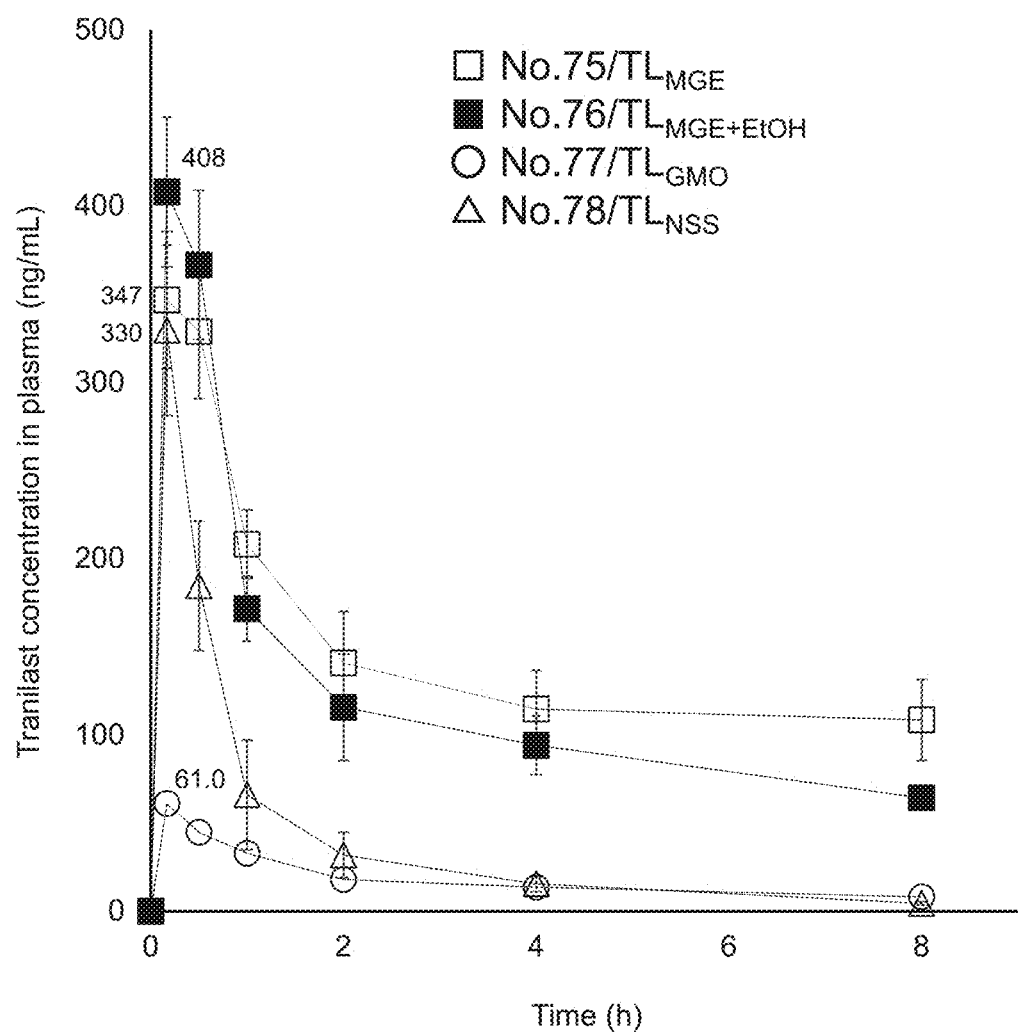
FIG. 15 is a diagram showing changes in tranilast concentration in plasma for 8 hours after intranasal administration. Each value is indicated by mean±standard error (S.E.). The open square depicts formulation No. 75, the filled square depicts formulation No. 76, the open circle depicts formulation No. 77, and the open triangle depicts formulation No. 78.
Figure 16:
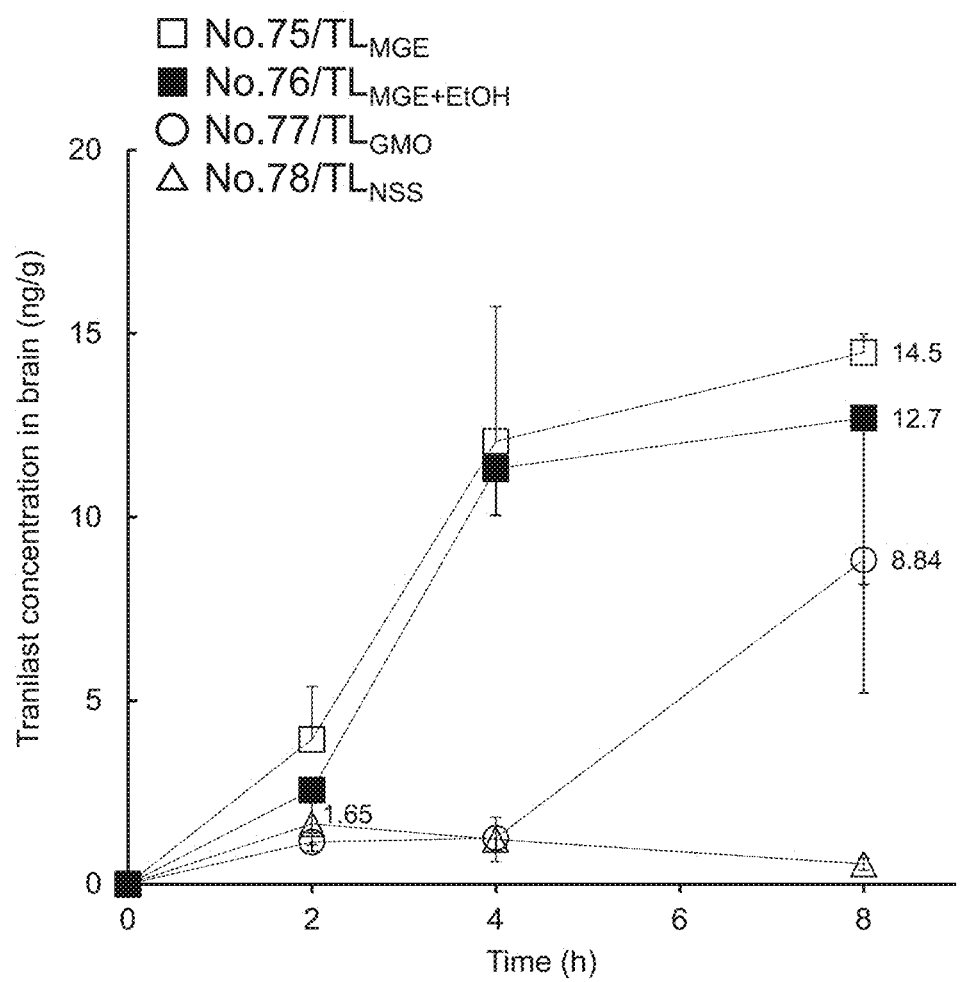
FIG. 16 is a diagram showing changes in tranilast concentration in the brain for 8 hours after intranasal administration. Each value is indicated by mean±standard error (S.E.). The open square depicts formulation No. 75, the filled square depicts formulation No. 76, the open circle depicts formulation No. 77, and the open triangle depicts formulation No. 78.
Figure 17A:
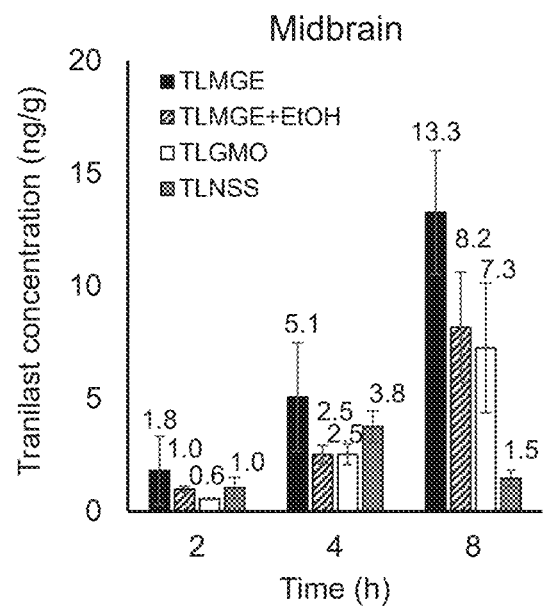
FIGS. 17A, 17B, 17C and 17D are diagrams showing tranilast concentrations in different regions in the brain at 2, 4, and 8 hours after intranasal administration.
Figure 17B:
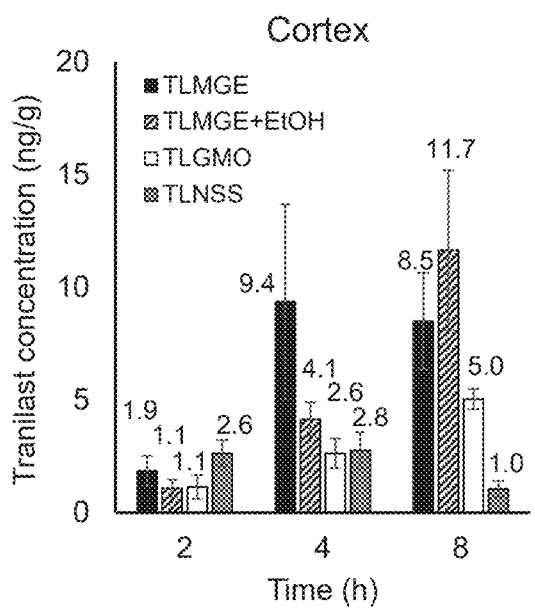
Figure 17C:
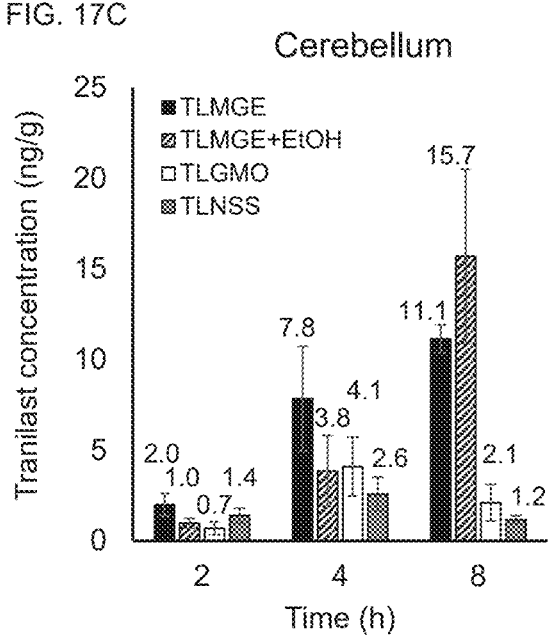
Figure 17D:
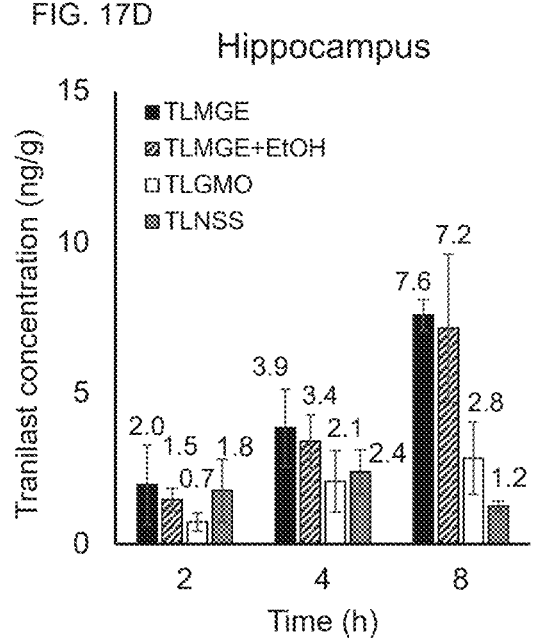
Figure 18A:
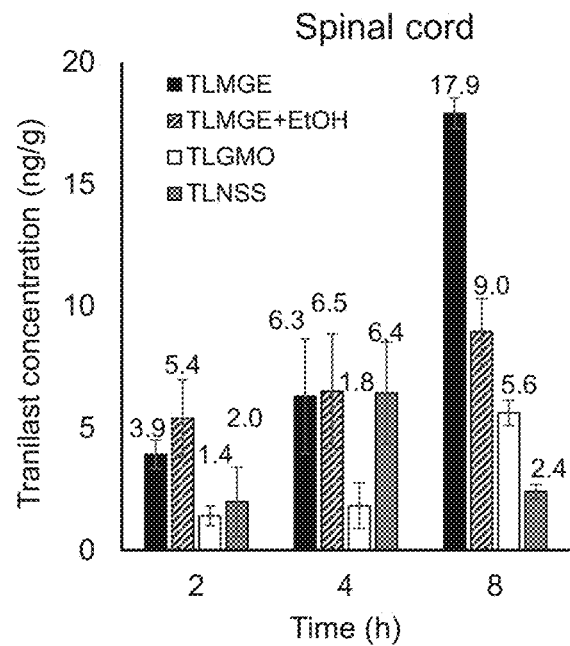
FIGS. 18A and 18B are diagrams showing tranilast concentrations in different regions in the brain at 2, 4, and 8 hours after intranasal administration.
Figure 18B:
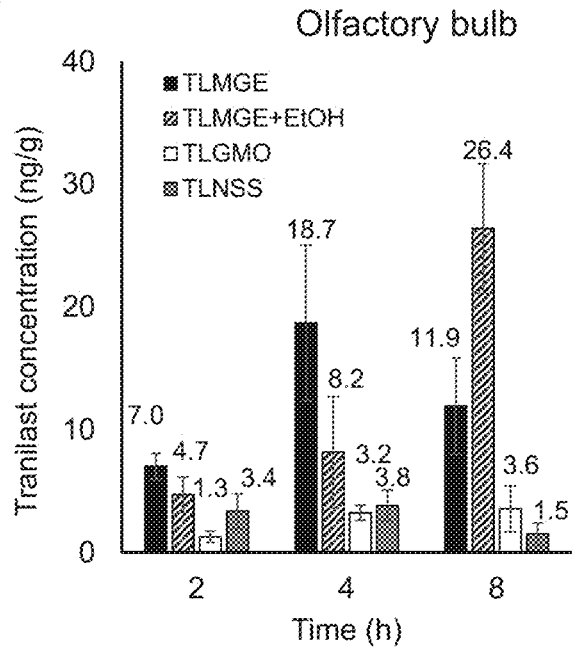

FIGS. 15 and 16 show changes in tranilast concentration in the plasma and in the brain for 8 hours after intranasal administration of each formulation. The ordinate of the graph shows an average tranilast concentration (an average value from the test conducted three to five times) (ng/mL or ng/g).

On the basis of the results shown in FIGS. 15 and 16, the time to maximum concentration (Tmax), the maximum concentration (Cmax), and the area under drug concentration-time curve ($AUC_{0-8}$) were determined as pharmacokinetic parameters of tranilast in the plasma and in the brain for 8 hours after intranasal administration of each formulation. Their values are shown in

TABLE 19

| Formulation No./Code Name | Site | $T_{max}$ (h) | $C_{max}$ (ng/mL or ng/g)* | $AUC_{0-8}$ (ng · h/mL or ng · h/g)** |
|---|---|---|---|---|
| No. 75/TLMGE | Plasma | 0.17 | 347 | 1150 |
|  | Brain | 8 | 14.5 | 69.6 |
| No. 76/TLMGE + EtOH | Plasma | 0.17 | 408 | 966 |
|  | Brain | 8 | 12.7 | 62.2 |
| No. 77/TLGMO | Plasma | 0.17 | 61.0 | 142 |
|  | Brain | 8 | 8.84 | 22.7 |
| NO. 78/TLNSS | Plasma | 0.17 | 330 | 311 |
|  | Brain | 2 | 1.65 | 4.43 |

*ng/mL for plasma, ng/g for brain
**ng · h/mL for plasma, ng · h/g for brain

Tmax for the plasma was 0.17 hours (at the time of the initial blood collection) after intranasal administration for all of emulsion Nos. 75 to 77 and comparative control formulation No. 78, indicating rapid systemic absorbability. Tmax for the brain was 2 hours (at the time of the initial blood collection) after intranasal administration for comparative control formulation No. 78 and, by contrast, was 8 hours or later after intranasal administration for both of emulsion Nos. 75 to 77.

In the plasma, Cmax did not largely differ between emulsion Nos. 75 and 76 containing C17MGE and comparative control formulation No. 78 whereas $AUC_{0-8}$ for Nos. 75 and 76 was 3 or more times higher than that for No. 78. In the brain, Cmax for Nos. 75 and 76 was about 8 times higher than that for No. 78, and $AUC_{0-8}$ for Nos. 75 and 76 was about 15 times higher than that for No. 78. On the other hand, emulsion No. 77 containing GMO had both Cmax and $AUC_{0-8}$ in the brain about 5 times higher than those for comparative control formulation No. 78, though both Cmax and $AUC_{0-8}$ in the plasma for No. 77 fell below the values of No. 78.

As described above, a high concentration of tranilast was detected both in the plasma and in the brain as to emulsion Nos. 75 and 76 containing C17MGE, and was larger than the concentration exhibited by emulsion No. 77 containing GMO. Particularly, it is notable that the tranilast concentration in the brain was markedly increased for emulsion Nos. 75 and 76 compared with No. 78. This result revealed that an emulsion containing C17MGE is excellent in drug delivery into the brain by intranasal administration.

FIGS. 17A-17D and 18A-18B show tranilast concentrations in different regions in the brain at 2, 4, and 8 hours after intranasal administration of each formulation. The ordinate of the graph shows an average tranilast concentration (an average value from the test conducted three to five times) (ng/g).

All of emulsion Nos. 75 to 77 and comparative control formulation No. 78 exhibited the incorporation of tranilast from 2 hours after initial excising, in all the brain regions. The tranilast concentrations from these formulations in the olfactory bulb among all the brain regions and in the spinal cord were generally higher than those in the other brain regions (FIGS. 17A-17D and 18A-18B). The olfactory bulb is adjacent to the nasal cavity, and the spinal cord is the entrance of a systemic route into the brain. Therefore, this result indicated that the transfer of tranilast into brain proceeds via both the olfactory route and the systemic route.

The tranilast concentrations from emulsion Nos. 75 and 76 containing C17MGE in all the brain regions are generally higher than those from emulsion No. 77 containing GMO and comparative control formulation No. 78 over 8 hours after intranasal administration, and were markedly high at 8 hours after intranasal administration (FIGS. 17A-17D and 18A-18B). This indicated that a higher concentration of tranilast accumulated throughout the brain regions over a long time as to emulsion Nos. 75 and 76 compared with emulsion No. 77 and comparative control formulation No. 78.

INDUSTRIAL APPLICABILITY

The present invention can provide an external preparation excellent in drug absorbability by living bodies.

All publications, patents and patent applications cited herein are incorporated herein by reference in their entirety.

The invention claimed is:

1. A method for administering a drug to a subject, comprising applying an external preparation non-orally to a living body mucosal surface of the subject to allow the drug in the external preparation to be released and permeate through mucosa,
   wherein the external preparation comprises a non-lamellar liquid crystal-forming lipid and a drug,
   wherein the non-lamellar liquid crystal-forming lipid is an amphipathic compound represented by the following general formula (I) or a salt thereof:

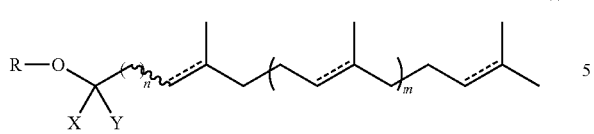

(I)

wherein X and Y each denote a hydrogen atom or together denote an oxygen atom, n denotes an integer from 0 to 2, m denotes the integer 1 or 2, the designation ═══ denotes a single bond or double bond, and R denotes a hydrophilic group having two or more hydroxyl groups, and wherein the external preparation further comprises hydroxypropylcellulose, and the external preparation comprises no aqueous medium or comprises an aqueous medium in an amount insufficient for forming liquid crystals by the non-lamellar liquid crystal-forming lipid, and is a liquid crystal precursor formulation in which the non-lamellar liquid crystal-forming lipid forms no liquid crystal in the external preparation.

2. The method according to claim 1, wherein R in the formula (I) denotes a hydrophilic group generated by removal of one hydroxy group from any compound selected from the group consisting of glycerol, erythritol, pentaerythritol, diglycerol, glyceric acid, triglycerol, xylose, sorbitol, ascorbic acid, glucose, galactose, mannose, dipentaerythritol, maltose, mannitol, and xylitol.

3. The method according to claim 1, wherein the non-lamellar liquid crystal-forming lipid is mono-O-(5,9,13,17-tetramethyloctadec-4-enoyl)glycerol.

4. The method according to claim 1, wherein the non-lamellar liquid crystal-forming lipid is mono-O-(5,9,13-trimethyltetradec-4-enoyl)glycerol.

5. A method for administering a drug to a subject, comprising by intranasal administration, applying an external preparation to a living body mucosal surface of the subject to allow the drug in the external preparation to be released and permeate through mucosa, thereby delivering the drug into brain,
wherein the external preparation comprises a non-lamellar lipid crystal-forming lipid and a drug,
wherein the non-lamellar liquid crystal-forming lipid is an amphipathic compound represented by the following general formula (I) or a salt thereof:

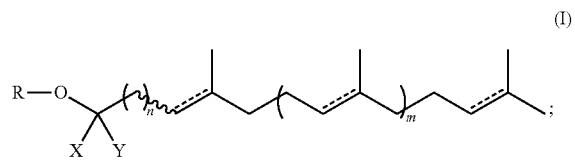

(I)

wherein X and Y each denote a hydrogen atom or together denote an oxygen atom, n denotes an integer from 0 to 2, m denotes the integer 1 or 2, the designation ═══ denotes a single bond or double bond, and R denotes a hydrophilic group having two or more hydroxyl groups, and wherein the external preparation further comprises a surfactant and water, and is an emulsion containing fine particles comprising the non-lamellar liquid crystal-forming lipid and the drug.

6. The method according to claim 1, wherein the external preparation further comprises an oil.

7. The method according to claim 5, wherein the external preparation further comprises an oil.

8. The method according to claim 1, wherein the external preparation further comprises ethanol.

9. The method according to claim 5, wherein the external preparation further comprises ethanol.

10. The method according to claim 5, wherein the non-lamellar liquid crystal-forming lipid is mono-O-(5,9,13,17-tetramethyloctadec-4-enoyl)glycerol.

11. The method according to claim 5, wherein the non-lamellar liquid crystal-forming lipid is mono-O-(5,9,13-trimethyltetradec-4-enoyl)glycerol.

* * * * *